US012662520B2

(12) United States Patent
Eryilmaz et al.

(10) Patent No.: US 12,662,520 B2
(45) Date of Patent: Jun. 23, 2026

(54) MASKED IL-2 CYTOKINES AND METHODS OF USE THEREOF

(71) Applicant: Xilio Development, Inc., Waltham, MA (US)

(72) Inventors: Ertan Eryilmaz, Waltham, MA (US); Carl Uli Bialucha, Waltham, MA (US); Dheeraj Tomar, Waltham, MA (US)

(73) Assignee: Xilio Development, Inc., Waltham, MA (US)

( * ) Notice: Subject to any disclaimer, the term of this patent is extended or adjusted under 35 U.S.C. 154(b) by 0 days.

(21) Appl. No.: 19/314,420

(22) Filed: Aug. 29, 2025

(65) Prior Publication Data

US 2026/0008831 A1      Jan. 8, 2026

Related U.S. Application Data

(63) Continuation of application No. PCT/US2025/011140, filed on Jan. 10, 2025.

(60) Provisional application No. 63/689,277, filed on Aug. 30, 2024, provisional application No. 63/619,623, filed on Jan. 10, 2024.

(51) Int. Cl.

| | |
|---|---|
| C07K 14/55 | (2006.01) |
| A61P 35/00 | (2006.01) |
| C07K 16/24 | (2006.01) |
| C07K 16/28 | (2006.01) |
| A61K 38/00 | (2006.01) |
| A61K 39/00 | (2006.01) |

(52) U.S. Cl.
CPC ............. C07K 14/55 (2013.01); A61P 35/00 (2018.01); C07K 16/246 (2013.01); C07K 16/2818 (2013.01); A61K 38/00 (2013.01); A61K 2039/505 (2013.01); C07K 2317/52 (2013.01); C07K 2317/565 (2013.01); C07K 2317/569 (2013.01); C07K 2317/76 (2013.01); C07K 2317/92 (2013.01); C07K 2319/30 (2013.01); C07K 2319/50 (2013.01); C07K 2319/70 (2013.01)

(58) Field of Classification Search
CPC .. C07K 14/55; C07K 16/246; C07K 2317/52; C07K 2317/565
See application file for complete search history.

(56) References Cited

U.S. PATENT DOCUMENTS

| | | |
|---|---|---|
| RE30,985 E | 6/1982 | Cartaya |
| 4,419,446 A | 12/1983 | Howley et al. |
| 4,560,655 A | 12/1985 | Baker |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 4,965,199 A | 10/1990 | Capon et al. |
| 5,122,464 A | 6/1992 | Wilson et al. |
| 5,122,469 A | 6/1992 | Mather et al. |
| 5,208,020 A | 5/1993 | Chari et al. |
| 5,264,365 A | 11/1993 | Georgiou et al. |
| 5,416,064 A | 5/1995 | Chari et al. |
| 5,508,192 A | 4/1996 | Georgiou et al. |
| 5,571,894 A | 11/1996 | Wels et al. |
| 5,587,458 A | 12/1996 | King et al. |
| 5,624,821 A | 4/1997 | Winter et al. |
| 5,635,483 A | 6/1997 | Pettit et al. |
| 5,639,635 A | 6/1997 | Joly et al. |
| 5,641,870 A | 6/1997 | Rinderknecht et al. |
| 5,648,237 A | 7/1997 | Carter |
| 5,648,260 A | 7/1997 | Winter et al. |
| 5,650,150 A | 7/1997 | Gillies |
| 5,712,374 A | 1/1998 | Kuntsmann et al. |
| 5,714,586 A | 2/1998 | Kunstmann et al. |
| 5,739,116 A | 4/1998 | Hamann et al. |
| 5,739,277 A | 4/1998 | Presta et al. |
| 5,767,285 A | 6/1998 | Hamann et al. |
| 5,770,701 A | 6/1998 | Mcgahren et al. |
| 5,770,710 A | 6/1998 | Mcgahren et al. |
| 5,773,001 A | 6/1998 | Hamann et al. |

(Continued)

FOREIGN PATENT DOCUMENTS

| | | |
|---|---|---|
| AU | 2012202125 A1 | 5/2012 |
| CA | 3112989 A1 | 4/2020 |

(Continued)

OTHER PUBLICATIONS

International Search Report for PCT/US2019/053588 dated Jan. 23, 2020 (4 pages).
International Search Report for PCT/US2021/025100 dated Sep. 24, 2021 (6 pages).
International Search Report for PCT/US2021/025103 dated Aug. 18, 2021 (7 pages).
International Search Report for PCT/US2021/025107 dated Jul. 21, 2021 (4 pages).
International Search Report for PCT/US2021/072603 dated May 24, 2022 (5 pages).
International Search Report for PCT/US2022/076395 dated Feb. 10, 2023 (8 pages).

(Continued)

*Primary Examiner* — Gyan Chandra
(74) *Attorney, Agent, or Firm* — Proskauer Rose LLP

(57)          ABSTRACT

The present invention provides, among other things, a masked cytokine comprising an interleukin 2 (IL-2) polypeptide, a VHH masking moiety, an anti-PD1 targeting moiety, and an engineered Fc domain comprising a tumor-associated protease cleavage site. In such masked cytokine, the IL-2 polypeptide is engineered to be activatable by a protease at a target site, such as in a tumor microenvironment. The VHH masking moiety blocks, occludes, inhibits (e.g., decreases) or otherwise prevents (e g masks) the activity or binding of the cytokine to its cognate receptor or protein. Upon proteolytic cleavage of the cleavage site in the Fc domain, the IL-2 polypeptide becomes activated, which renders it capable of binding to its cognate receptor or protein with increased affinity.

6 Claims, 26 Drawing Sheets

Specification includes a Sequence Listing.

(56) References Cited

U.S. PATENT DOCUMENTS

| | | | |
|---|---|---|---|
| 5,780,588 | A | 7/1998 | Pettit et al. |
| 5,834,597 | A | 11/1998 | Tso et al. |
| 5,869,046 | A | 2/1999 | Presta et al. |
| 5,877,296 | A | 3/1999 | Hamann et al. |
| 5,891,693 | A | 4/1999 | Bebbington et al. |
| 5,939,598 | A | 8/1999 | Kucherlapati et al. |
| 6,027,888 | A | 2/2000 | Georgiou et al. |
| 6,075,181 | A | 6/2000 | Kucherlapati et al. |
| 6,083,715 | A | 7/2000 | Georgiou et al. |
| 6,114,598 | A | 9/2000 | Kucherlapati et al. |
| 6,150,584 | A | 11/2000 | Kucherlapati et al. |
| 6,162,963 | A | 12/2000 | Kucherlapati et al. |
| 6,165,745 | A | 12/2000 | Ward et al. |
| 6,194,551 | B1 | 2/2001 | Idusogie et al. |
| 6,248,516 | B1 | 6/2001 | Winter et al. |
| 6,593,132 | B1 | 7/2003 | Borgford |
| 6,602,684 | B1 | 8/2003 | Umana et al. |
| 6,630,579 | B2 | 10/2003 | Chari et al. |
| 6,821,505 | B2 | 11/2004 | Ward |
| 6,942,853 | B2 | 9/2005 | Chernajovsky et al. |
| 7,498,298 | B2 | 3/2009 | Doronina et al. |
| 8,399,219 | B2 | 3/2013 | Stagliano et al. |
| 8,507,222 | B2 | 8/2013 | Wong et al. |
| 9,206,243 | B2 | 12/2015 | Len et al. |
| 9,428,573 | B2 | 8/2016 | Wong et al. |
| 9,975,937 | B2 | 5/2018 | Pavlakis et al. |
| 10,106,621 | B2 | 10/2018 | Cobbold et al. |
| 10,150,805 | B2 | 12/2018 | Wong et al. |
| 10,184,009 | B2 | 1/2019 | Ast et al. |
| 10,206,980 | B2 | 2/2019 | Qu et al. |
| 10,350,270 | B2 | 7/2019 | Mccauley |
| 10,358,477 | B2 | 7/2019 | Jacques et al. |
| 10,501,543 | B2 | 12/2019 | Bernett et al. |
| 10,604,576 | B2 | 3/2020 | Campbell et al. |
| 10,906,952 | B2 | 2/2021 | Gundram et al. |
| 11,053,294 | B2 | 7/2021 | Karow et al. |
| 11,059,876 | B2 | 7/2021 | Yeung et al. |
| 11,352,403 | B2 | 6/2022 | Winston et al. |
| 11,357,826 | B2 | 6/2022 | Xu et al. |
| 11,358,999 | B2 | 6/2022 | Bernett et al. |
| 11,453,710 | B2 | 9/2022 | Winston et al. |
| 11,492,383 | B2 | 11/2022 | Gillies |
| 11,542,312 | B2 | 1/2023 | Merchant et al. |
| 11,597,753 | B2 | 3/2023 | Yue et al. |
| 11,634,467 | B2 | 4/2023 | Li et al. |
| 11,642,417 | B2 | 5/2023 | Mulligan et al. |
| 11,673,931 | B2 | 6/2023 | Lowe et al. |
| 11,739,132 | B2 | 8/2023 | Winston et al. |
| 11,866,476 | B2 | 1/2024 | Karow et al. |
| 11,981,716 | B2 | 5/2024 | Winston et al. |
| 12,036,266 | B2 | 7/2024 | Winston et al. |
| 12,060,424 | B2 | 8/2024 | Yang et al. |
| 2002/0164328 | A1 | 11/2002 | Shinkawa et al. |
| 2003/0115614 | A1 | 6/2003 | Kanda et al. |
| 2003/0157108 | A1 | 8/2003 | Presta |
| 2003/0190311 | A1 | 10/2003 | Dall et al. |
| 2004/0053829 | A1 | 3/2004 | Pfizenmaier et al. |
| 2004/0093621 | A1 | 5/2004 | Shitara et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0132140 | A1 | 7/2004 | Satoh et al. |
| 2005/0014934 | A1 | 1/2005 | Hinton et al. |
| 2005/0123546 | A1 | 6/2005 | Umana et al. |
| 2006/0236411 | A1 | 10/2006 | Dreher et al. |
| 2007/0048282 | A1 | 3/2007 | Rosen et al. |
| 2007/0269422 | A1 | 11/2007 | Beirnaert et al. |
| 2008/0311655 | A1 | 12/2008 | Gillies et al. |
| 2010/0068175 | A1 | 3/2010 | Gillies et al. |
| 2013/0089516 | A1 | 4/2013 | Frelinger et al. |
| 2014/0053829 | A1 | 2/2014 | Lee |
| 2014/0294823 | A1 | 10/2014 | Moore et al. |
| 2014/0302037 | A1 | 10/2014 | Borges et al. |
| 2014/0308285 | A1 | 10/2014 | Yan et al. |
| 2015/0110857 | A1 | 4/2015 | Derosa et al. |
| 2015/0139984 | A1 | 5/2015 | Brezski et al. |
| 2016/0152686 | A1 | 6/2016 | Camphausen et al. |
| 2016/0194665 | A1 | 7/2016 | Collingwood et al. |
| 2016/0200645 | A1 | 7/2016 | Henri et al. |
| 2017/0020963 | A1 | 1/2017 | Qu et al. |
| 2017/0240608 | A1 | 8/2017 | Stagliano et al. |
| 2018/0118833 | A1 | 5/2018 | Hofer et al. |
| 2019/0263877 | A1 | 8/2019 | Yeung et al. |
| 2019/0367576 | A1 | 12/2019 | Winston et al. |
| 2019/0391152 | A1 | 12/2019 | Abrignani et al. |
| 2020/0207846 | A1 | 7/2020 | Igawa et al. |
| 2020/0283489 | A1 | 9/2020 | Winston et al. |
| 2020/0308242 | A1 | 10/2020 | Lowe et al. |
| 2020/0392235 | A1 | 12/2020 | Lu et al. |
| 2020/0399338 | A1 | 12/2020 | Caffaro et al. |
| 2021/0024631 | A1 | 1/2021 | Kley et al. |
| 2021/0061871 | A1 | 3/2021 | Niazi et al. |
| 2021/0115102 | A1 | 4/2021 | Winston et al. |
| 2021/0130430 | A1 | 5/2021 | Winston et al. |
| 2021/0139553 | A1 | 5/2021 | Li et al. |
| 2021/0187027 | A1 | 6/2021 | Wu et al. |
| 2021/0188934 | A1 | 6/2021 | Wu et al. |
| 2021/0196796 | A1 | 7/2021 | Penaflor-aspuria et al. |
| 2021/0221864 | A1 | 7/2021 | Williams et al. |
| 2021/0238308 | A1 | 8/2021 | Ikawa et al. |
| 2021/0260163 | A1 | 8/2021 | Yu et al. |
| 2021/0355208 | A1 | 11/2021 | Moore et al. |
| 2022/0002370 | A1 | 1/2022 | Karow et al. |
| 2022/0025050 | A1 | 1/2022 | Poirier et al. |
| 2022/0047714 | A1 | 2/2022 | Mulligan et al. |
| 2022/0089667 | A1 | 3/2022 | Timmer et al. |
| 2022/0170028 | A1 | 6/2022 | Li et al. |
| 2022/0227837 | A1 | 7/2022 | Li |
| 2022/0306735 | A1 | 9/2022 | Dekosky et al. |
| 2022/0363782 | A1 | 11/2022 | Davis et al. |
| 2022/0402989 | A1 | 12/2022 | Wu et al. |
| 2023/0028959 | A1 | 1/2023 | Karow et al. |
| 2023/0030037 | A1 | 2/2023 | Karow et al. |
| 2023/0072822 | A1 | 3/2023 | Rozenfeld et al. |
| 2023/0107363 | A1 | 4/2023 | De Jong et al. |
| 2023/0124669 | A1 | 4/2023 | Luo et al. |
| 2023/0144608 | A1 | 5/2023 | Tomar et al. |
| 2023/0235006 | A1 | 7/2023 | Karow et al. |
| 2024/0270806 | A1 | 8/2024 | Chichili et al. |

FOREIGN PATENT DOCUMENTS

| | | |
|---|---|---|
| CN | 103002913 A | 3/2013 |
| CN | 105229031 A | 1/2016 |
| CN | 108218993 A | 6/2018 |
| CN | 113248610 A | 8/2021 |
| EA | 202190874 A1 | 8/2021 |
| EP | 0425235 B1 | 9/1996 |
| EP | 2639241 A2 | 9/2013 |
| EP | 3093295 B1 | 5/2020 |
| EP | 3740501 A1 | 11/2020 |
| EP | 3762406 A2 | 1/2021 |
| EP | 3773674 A1 | 2/2021 |
| EP | 3792277 A1 | 3/2021 |
| EP | 3810171 A1 | 4/2021 |
| EP | 4110404 A1 | 1/2023 |
| EP | 3490585 B1 | 5/2023 |
| EP | 4172216 A1 | 5/2023 |
| JP | S63203626 A | 8/1988 |
| JP | 2003507012 A | 2/2003 |
| JP | 2004508828 A | 3/2004 |
| JP | 2015530984 A | 10/2015 |
| JP | 2021530243 A | 11/2021 |
| JP | 7479383 B2 | 5/2024 |
| KR | 20030048041 A | 6/2003 |
| SA | 521421574 | 4/2022 |
| WO | 8700195 A1 | 1/1987 |
| WO | 9003430 A1 | 4/1990 |
| WO | 9101743 A1 | 2/1991 |
| WO | 9208495 A1 | 5/1992 |
| WO | 9308829 A1 | 5/1993 |
| WO | 9316185 A2 | 8/1993 |
| WO | 9411026 A2 | 5/1994 |
| WO | 9429351 A2 | 12/1994 |

(56) References Cited

FOREIGN PATENT DOCUMENTS

| | | | |
|---|---|---|---|
| WO | 9627011 | A1 | 9/1996 |
| WO | 9730087 | A1 | 8/1997 |
| WO | 9858964 | A1 | 12/1998 |
| WO | 9922764 | A1 | 5/1999 |
| WO | 9927011 | A2 | 6/1999 |
| WO | 9951642 | A1 | 10/1999 |
| WO | 0042072 | A2 | 7/2000 |
| WO | 0061739 | A1 | 10/2000 |
| WO | 0110912 | A1 | 2/2001 |
| WO | 0129246 | A1 | 4/2001 |
| WO | 0179271 | A1 | 10/2001 |
| WO | 0220715 | A2 | 3/2002 |
| WO | 0222833 | A1 | 3/2002 |
| WO | 0243478 | A2 | 6/2002 |
| WO | 02076489 | A1 | 10/2002 |
| WO | 03011878 | A2 | 2/2003 |
| WO | 03059934 | A2 | 7/2003 |
| WO | 03084570 | A1 | 10/2003 |
| WO | 03085119 | A1 | 10/2003 |
| WO | 2004041865 | A2 | 5/2004 |
| WO | 2004056312 | A2 | 7/2004 |
| WO | 2005035586 | A1 | 4/2005 |
| WO | 2005035778 | A1 | 4/2005 |
| WO | 2005053742 | A1 | 6/2005 |
| WO | 2006106905 | A1 | 10/2006 |
| WO | 2006133148 | A2 | 12/2006 |
| WO | 2011100786 | A1 | 8/2011 |
| WO | 2011124718 | A1 | 10/2011 |
| WO | 2012059486 | A1 | 5/2012 |
| WO | 2012107417 | A1 | 8/2012 |
| WO | 2014023752 | A1 | 2/2014 |
| WO | 2014142955 | A1 | 9/2014 |
| WO | 2016154675 | A1 | 10/2016 |
| WO | 2016200645 | A1 | 12/2016 |
| WO | 2017127514 | A1 | 7/2017 |
| WO | 2017165464 | | 9/2017 |
| WO | 2018071918 | A1 | 4/2018 |
| WO | 2018085555 | A1 | 5/2018 |
| WO | 2018151868 | A2 | 8/2018 |
| WO | 2018170336 | A1 | 9/2018 |
| WO | 2018184964 | A1 | 10/2018 |
| WO | 2018184965 | A1 | 10/2018 |
| WO | 2019129053 | A1 | 7/2019 |
| WO | 2019143669 | A1 | 7/2019 |
| WO | 2019166946 | A1 | 9/2019 |
| WO | 2019173832 | A2 | 9/2019 |
| WO | 2019191295 | A1 | 10/2019 |
| WO | 2019191519 | A1 | 10/2019 |
| WO | 2019209965 | A2 | 10/2019 |
| WO | 2019214757 | A1 | 11/2019 |
| WO | 2019222294 | A1 | 11/2019 |
| WO | 2019222295 | A1 | 11/2019 |
| WO | 2019222296 | A1 | 11/2019 |
| WO | 2019246379 | A1 | 12/2019 |
| WO | 2019246392 | A1 | 12/2019 |
| WO | 2020023702 | A1 | 1/2020 |
| WO | 2020041758 | A1 | 2/2020 |
| WO | 2020047299 | A1 | 3/2020 |
| WO | 2020069398 | A1 | 4/2020 |
| WO | 2020086758 | A1 | 4/2020 |
| WO | 2020088459 | A1 | 5/2020 |
| WO | 2020123980 | A1 | 6/2020 |
| WO | 2020146221 | A1 | 7/2020 |
| WO | 2020232305 | A1 | 11/2020 |
| WO | 2020242884 | A1 | 12/2020 |
| WO | 2020247843 | A2 | 12/2020 |
| WO | 2020252264 | A1 | 12/2020 |
| WO | 2020259536 | A1 | 12/2020 |
| WO | 2021001289 | A1 | 1/2021 |
| WO | 2021016599 | A1 | 1/2021 |
| WO | 2021016640 | A1 | 1/2021 |
| WO | 2021030483 | A1 | 2/2021 |
| WO | 2021030633 | A1 | 2/2021 |
| WO | 2021035188 | A1 | 2/2021 |
| WO | 2021054867 | A1 | 3/2021 |
| WO | 2021062406 | A1 | 4/2021 |
| WO | 2021092719 | A1 | 5/2021 |
| WO | 2021097376 | A1 | 5/2021 |
| WO | 2021119429 | A1 | 6/2021 |
| WO | 2021119516 | A1 | 6/2021 |
| WO | 2021127487 | A2 | 6/2021 |
| WO | 2021127495 | A1 | 6/2021 |
| WO | 2021142471 | A1 | 7/2021 |
| WO | 2021142476 | A1 | 7/2021 |
| WO | 2021146455 | A1 | 7/2021 |
| WO | 2021149697 | A1 | 7/2021 |
| WO | 2021150936 | A1 | 7/2021 |
| WO | 2021174034 | A1 | 9/2021 |
| WO | 2021185362 | A1 | 9/2021 |
| WO | 2021189139 | A1 | 9/2021 |
| WO | 2021202673 | A2 | 10/2021 |
| WO | 2021202675 | A1 | 10/2021 |
| WO | 2021202678 | A1 | 10/2021 |
| WO | 2021216916 | A1 | 10/2021 |
| WO | 2021222762 | A2 | 11/2021 |
| WO | 2021258213 | A1 | 12/2021 |
| WO | 2022050401 | A2 | 3/2022 |
| WO | 2022087149 | A2 | 4/2022 |
| WO | 2022115865 | A2 | 6/2022 |
| WO | 2022155263 | A2 | 7/2022 |
| WO | 2022156773 | A1 | 7/2022 |
| WO | 2022167689 | A1 | 8/2022 |
| WO | 2022178103 | A1 | 8/2022 |
| WO | 2022192898 | A2 | 9/2022 |
| WO | 2022212614 | A1 | 10/2022 |
| WO | 2022221746 | A1 | 10/2022 |
| WO | 2022262496 | A1 | 12/2022 |
| WO | 2023004368 | A1 | 1/2023 |
| WO | 2023279085 | A1 | 1/2023 |
| WO | 2023281479 | A1 | 1/2023 |
| WO | 2023281481 | A1 | 1/2023 |
| WO | 2023023065 | A1 | 2/2023 |
| WO | 2023044321 | A1 | 3/2023 |
| WO | 2023045977 | A1 | 3/2023 |
| WO | 2023050006 | A1 | 4/2023 |
| WO | 2023060242 | A1 | 4/2023 |
| WO | 2023061005 | A1 | 4/2023 |
| WO | 2023141555 | A2 | 7/2023 |
| WO | 2023164288 | A2 | 8/2023 |
| WO | 2023170475 | A2 | 9/2023 |
| WO | 2023220647 | A1 | 11/2023 |
| WO | 2023222886 | A1 | 11/2023 |
| WO | 2024014808 | A1 | 1/2024 |
| WO | 2024015960 | A1 | 1/2024 |
| WO | 2024026449 | A2 | 2/2024 |
| WO | 2024030843 | A1 | 2/2024 |
| WO | 2024030845 | A1 | 2/2024 |
| WO | 2024030847 | A1 | 2/2024 |
| WO | 2024030850 | A1 | 2/2024 |
| WO | 2024030858 | A1 | 2/2024 |
| WO | 2024039973 | A2 | 2/2024 |
| WO | 2024054424 | A1 | 3/2024 |
| WO | 2024068705 | A1 | 4/2024 |
| WO | 2024119193 | A2 | 6/2024 |
| WO | 2024150172 | A1 | 7/2024 |
| WO | 2024150174 | A1 | 7/2024 |
| WO | 2024150175 | A1 | 7/2024 |

OTHER PUBLICATIONS

International Search Report for PCT/US2023/014128 dated Aug. 21, 2023 (11 pages).

International Search Report for PCT/US2023/070206 dated Oct. 18, 2023 (7 pages).

International Search Report for PCT/US2024/044441 dated Dec. 12, 2024 (5 pages).

International Search Report for PCT/US2024/044733 dated Dec. 16, 2024 (7 pages).

International Search Report for PCT/US2025/011140 dated May 19, 2025 (5 pages).

"Anti-IL2 antibody heavy chain, Seq ID 87", Database Geneseq, Oct. 26, 2023 (2 pages).

"Anti-PD-1 antibody light chain, Seq ID 32.", Database Geneseq, Dec. 27, 2018 (2 pages).

(56)　　References Cited

OTHER PUBLICATIONS

"Diguanylate cyclase", The Wayback Machine, https://web.archive.org/web/20171107063802/https://enzyme.expasy.org/EC/2.7.7.65, 2017, accessed Jul. 24, 2024 (2 pages).

"Diguanylate cyclase [Parafrankia sp. BMG5.11]", from https://ncbi.nlm.nih.gov/protein/TCJ40027.1?report=genbank&log$=protalign&blast_rank=6&RID=A7PHCH8P013, 2019 (3 pages).

"Proteolytically cleavable peptide linker", from https://web.expasy.org/cgi-bin/peptide_cutter/peptidecutter.pl, accessed 2024 (2 pages).

"Remington: The Science and Practice of Pharmacy", Gennaro (Ed.), 20th Edition, 2000, Lippincott Williams & Wilkins, Philadelphia, PA (4 pages).

"Transposase—Lyngbya aestuarii BL J", UniProt, retrieved Jan. 12, 2022 from URL: https://www.uniprot.org/uniprotkb/U7QND7/entry (4 pages).

Adams, et al., "Targeting cytokines to inflammation sites", Nature Biotechnology, vol. 21, No. 11, Nov. 2003, pp. 1314-1320, DOI: 10.1038/nbt888 (7 pages).

Arie, Jean-Phillippe, et al., "Chaperone function of FkpA, a heat shock prolyl isomerase, in the periplasm of Escherichia coli", Molecular Microbiology, vol. 39, No. 1, 2001, pp. 199-210 (12 pages).

Atwell, Shane, et al., "Stable Heterodimers from Remodeling the Domain Interface of a Homodimer using a Phage Display Library", Journal of Molecular Biology, vol. 270, 1997, pp. 26-35 (10 pages).

Bachmann, Barbara J., "Derivations and Genotypes of Some Mutant Derivatives of Escherichia coli K-12", Escherichia coli and Salmonella typhimurium: Cellular and Molecular Biology, vol. 2, Section G, No. 72, 1987, pp. 1190-1219 (32 pages).

Barnes, David, et al., "Methods for Growth of Cultured Cells in Serum-Free Medium", Analytical Biochemistry, vol. 102, 1980, pp. 255-270 (16 pages).

Bass, Steven, et al., "Hormone Phage: An Enrichment Method for Variant Proteins with Altered Binding Properties", Proteins: Structure, Function, and Genetics, vol. 8, 1990, pp. 309-314 (6 pages).

Berge, et al., "Pharmaceutical Salts", Journal of Pharmaceutical Sciences, vol. 66, No. 1, Jan. 1977, pp. 1-19, DOI: 10.1002/jps.2600660104 (20 pages).

Bernett, et al., "Potency-reduced IL 15/IL 15Rα heterodimeric Fc-fusions display enhanced in vivo activity through increase exposure", Poster, Xencor, AACR, Abstract #5565, 2018 (1 page).

Berry, Helen K., et al., "Valine, Isoleucine, and Leucine: A Treatment for Phenylketonuria", AJDC, vol. 144, May 1990, pp. 539-543 (5 pages).

Boerner, Paula, et al., "Production of Antigen-Specific Human Monoclonal Antibodies from In Vitro-Primed Human Splenocytes", The Journal of Immunology, vol. 147, No. 1, Jul. 1, 1991, pp. 86-95 (10 pages).

Bothmann, Hendrick, et al., "Improving Expression of scFv Fragments by Coexpression of Periplasmic Chaperones", Antibody Engineering, Springer Lab Manuals, 2001, pp. 307-317, DOI: 10.1007/978-3-662-04605-0_23, (12 pages).

Bothmann, Hendrick, et al., "The Periplasmic Escherichia coli Peptidylprolyl cis,trans-Isomerase FkpA", The Journal of Biological Chemistry, vol. 275, No. 22, Jun. 2, 2000, pp. 17100-17105 (7 pages).

Brennan, Maureen, et al., "Preparation of Bispecific Antibodies by Chemical Recombinant of Monoclonal Immunoglobulin G1 Fragments", Science, vol. 229, Jul. 5, 1985, pp. 81-83 (3 pages).

Brodeur, Bernard R., et al., "Mouse-Human Myeloma Partners for the Production of Heterohybridomas", Monoclonal Antibody Production Techniques and Applications, Ch. 4, 1987, pp. 51-63 (13 pages).

Caescu, Cristina I., et al., "Active site determinants of substrate recognition by the metalloproteinases TACE and ADAM10", Biochem J., vol. 242, No. 1, Nov. 15, 2010, pp. 79-88, DOI: 10.1042/BJ20090549, Author Manuscript (21 pages).

Cameron, Mark J., et al., "Cytokines, Chemokines and Their Receptors", Madame Curie Bioscience Database [Internet], Austin (TX): Landes Bioscience; 2000-2013 (25 pages).

Carter, Paul, "Bispecific human IgG by design", Journal of Immunological Methods, vol. 248, 2001, pp. 7-15, DOI: 10.1016/S0022-1759(00)00339-2 (9 pages).

Carter, Paul, et al., "High Level Escherichia coli Expression and Production of a Bivalent Humanized Antibody Fragment", Bio/Technology, vol. 10, Feb. 1992, pp. 163-167 (5 pages).

Chapman, Andrew P., et al., "Therapeutic antibody fragments with prolonged in vivo half-lives", Nature Biotechnology, vol. 17, Aug. 1999, pp. 780-783 (4 pages).

Chari, Ravi V.J., et al., "Immunoconjugates Containing Novel Matyansinoids: Promising Anticancer Drugs", Cancer Research, vol. 52, Jan. 1, 1992, pp. 127-131 (5 pages).

Chen, Jun, et al., "Chaperone Activity of DsbC", The Journal of Biological Chemistry, vol. 274, No. 28, Jul. 9, 1999, pp. 19601-19605 (6 pages).

Chen, Xiaoying, et al., "Fusion Protein Linkers: Property, Design and Functionality", Advanced Drug Delivery Reviews, vol. 65, No. 10, Oct. 15, 2013, pp. 1357-1369, DOI: 10.1016/j.addr.2012.09.039, Author Manuscript (32 pages).

Choe, Weonu, et al., "Fc-Binding Ligands of Immunoglobulin G: An Overview of High Affinity Proteins and Peptides", Materials, vol. 9, No. 994, 2016, pp. 1-17, DOI: 10.3390/ma9120994 (17 pages).

Cunningham, Brian C., et al., "High-Resolution Epitope Mapping of hGH-Receptor Interactions by Alanine-Scanning Mutagenesis", Science, vol. 244, Jun. 1989, pp. 1081-1085 (5 pages).

Damodaran, Vinod Babu, et al., "Protein PEGylation: An overview of chemistry and process considerations", European Pharmaceutical Review, Issue 3, Feb. 2010, pp. 18-26 (10 pages).

Davies, David R., et al., "Antibody-Antigen Complexes", Ann. Rev. Biochem., vol. 59, 1990, pp. 439-473 (35 pages).

Dennis, Mark S., et al., "Albumin Binding as a General Strategy for Improving the Pharmacokinetics of Proteins", The Journal of Biological Chemistry, vol. 277, No. 38, Sep. 20, 2002, pp. 35035-35043, DOI: 10.1074/jbc.M2058524200 (10 pages).

Dubowchik, Gene M., et al., "Doxorubicin Immunoconjugates Containing Bivalent, Lysosomally-Cleavable Dipeptide Linkages", Bioorganic & Medicinal Chemistry Letters, vol. 12, 2002, pp. 1529-1532, DOI: 10.1016/S0960-894X(02)00194-4 (4 pages).

Duncan, Alexander R., et al., "The binding site for C1q on IgG", Nature, vol. 332, Apr. 23, 1988, pp. 738-740 (3 pages).

Eryilmaz, Ertan, et al., "XTX501, a tumor-activated PD1/IL2 bispecific molecule, designed to overcome IL-2 receptor-mediated clearance, improve tolerability and stimulate antigen-experienced CD8+ T cells in the tumor microenvironment of murine models", Poster No. 719, Xilio Therapeutics, Apr. 2, 2024 (1 page).

Firan, Mihail, et al., "The MHC class I-related receptor, FcRn, plays an essential role in the maternofetal transfer of gamma-globulin in humans", International Immunology, vol. 13, No. 8, 2001, pp. 993-1002 (10 pages).

Fishwild, Dianne M., et al., "High-avidity human IgGk monoclonal antibodies from a novel strain of minilocus transgenic mice", Nature Biotechnology, vol. 14, Jul. 1996, pp. 845-851 (7 pages).

Goodman, Joel W., et al., "Immunoglobulin Proteins", Basic & Clinical Immunology, 8th Ed., 1994, Ed. Daniel Stites, Appleton & Lange, Norwalk, CT, pp. 71 and Ch. 6 (26 pages).

Graham, F. L., et al., "Characteristics of a Human Cell Line Transformed by DNA from Human Adenovirus Type 5", J. Gen. Virol., vol. 36, 1977, pp. 59-74 (14 pages).

Gunasekaran, Kannan, et al., "Enhancing Antibody Fc Heterodimer Formation through Electrostatic Steering Effects", The Journal of Biological Chemistry, vol. 285, No. 25, Jun. 18, 2010, pp. 19637-19464 (10 pages).

Guss, Bengt, et al., "Structure of the IgG-binding regions of streptococcal protein G", The EMBO Journal, vol. 5, No. 7, 1986, pp. 1567-1575 (9 pages).

Guyer, Ruth L., et al., "Immunoglobulin Binding by Mouse Intestinal Epithelial Cell Receptors", The Journal of Immunology, vol. 117, No. 2, Aug. 1976, pp. 587-593 (7 pages).

Ha, Ji-Hee, et al., "Immunoglobulin Fc Heterodimer Platform Technology: From Design to Applications in Therapeutic Antibodies and Proteins", Frontiers in Immunology, vol. 7, Article No. 394, Oct. 6, 2016, DOI: 10.3389/fimmu.2016.00394, (16 pages).

(56) References Cited

OTHER PUBLICATIONS

Ham, Richard G., et al., "Media and Growth Requirements", Methods in Enzymology, vol. LVIII, 1979, pp. 44-93 (50 pages).

Hara, Hiroshi, et al., "Overproduction of Penicillin-Binding Protein 7 Suppresses Thermosensitive Growth Defect at Low Osmolarity due to an spr Mutation of *Escherichia coli*", Microbial Drug Resistance, vol. 2, No. 1, 1996, pp. 63-72 (10 pages).

Hinman, Lois M., et al., "Preparation and Characterization of Monoclonal Antibody Conjugates of the Calicheamicins: A Novel and Potent Family of Antitumor Antibiotics", Cancer Research, vol. 53, Jul. 15, 1993, pp. 3336-3342 (7 pages).

Hsu, Eric J., et al., "A cytokine receptor-masked IL2 prodrug selectively activates tumor-infiltrating lymphocytes for potent anti-tumor therapy", Nature Communications, vol. 12, 2021, pp. 2768, DOI: 10.1038/s41467-021-22980-w (13 pages).

Hudson, Peter J., et al., "Engineered antibodies", Nature Medicine, vol. 9, No. 1, Jan. 2003, pp. 129-134 (6 pages).

Idusogie, Esohe E., et al., "Mapping of the C1q Binding Site on Rituxan, a Chimeric Antibody with a Human IgG1 Fc", The Journal of Immunology, vol. 164, 2000, pp. 4178-4184, DOI: 10.4049/jimmunol.164.8.4178 (8 pages).

Imai-Nishiya, Harue, et al., "Double knockdown of alpha 1,6-fucosyltransferase (FUT8) and GDP-mannose 4,6-dehydratase (GMD) in antibody-producing cells: a new strategy for generating fully non-fucosylated therapeutic antibodies with enhanced ADCC", BMC Biotechnology, vol. 7, No. 84, Nov. 2007, pp. 1-13, DOI: 10.1186/1472-6750/7/84 (13 pages).

Jazayeri, Jalal A., et al., "Fc-Based Cytokines: Prospects for Engineering Superior Therapeutics", Biodrugs, vol. 22, No. 1, 2008, pp. 11-26, DOI: 10.2165/00063030-200822010-00002 (16 pages).

Jefferis, Roy, et al., "Human immunoglobulin allotypes", mAbs, vol. 1, No. 4, 2009, pp. 332-338, DOI: 10.4161/mabs.1.4.9122 (8 pages).

Jeffrey, Scott C., et al., "Dipeptide-based highly potent doxorubicin antibody conjugates", Bioorganic & Medicinal Chemistry Letters, vol. 16, 2006, pp. 358-362, DOI: 10.1016/j.bmcl.2005.09.081 (5 pages).

Jones, Peter T., et al., "Replacing the complementarity-determining regions in a human antibody with those from a mouse", Nature, vol. 321, May 29, 1986, pp. 522-525 (4 pages).

Kim, Jin-Kyoo, et al., "Localization of the site of the murine IgG1 molecule that is involved in binding to the murine intestinal Fc receptor", European Journal of Immunology, vol. 24, No. 10, 1994, pp. 2429-2434, DOI: 10.1002/eji.1830241025 (7 pages).

King, H. Dalton, et al., "Monoclonal Antibody Conjugates of Doxorubicin Prepared with Branched Peptide Linkers: Inhibition of Aggregation by Methoxytriethyleneglycol Chains", J. Med. Chem., vol. 45, 2002, pp. 4336-4343, DOI: 10.1021/jm020149g (8 pages).

Klein, Christian, et al., "Progress in overcoming the chain association issue in bispecific heterodimeric IgG antibodies", mAbs, vol. 4, No. 6, Nov. 2012, pp. 653-663, DOI: 10.4161/mabs.21379 (11 pages).

Kontermann, Roland E., et al., "Bispecific antibodies", Drug Discovery Today, vol. 20, No. 7, Jul. 2015, pp. 838-847, DOI: 10.1016/j.drudis.2015.02.008 (12 pages).

Kozbor, Danuta, et al., "A Human Hybrid Myeloma for Production of Human Monoclonal Antibodies", The Journal of Immunology, vol. 133, No. 6, Dec. 1984, pp. 3001-3005 (5 pages).

Kratz, F., et al., "Prodrugs of Anthracyclines in Cancer Chemotherapy", Current Medical Chemistry, vol. 13, 2006, pp. 477-523 (47 pages).

Krieg, Carsten, et al., "Improved IL-2 immunotherapy by selective stimulation of IL-2 receptors on lymphocytes and endothelial cells", Proceedings of the National Academy of Sciences, vol. 107, No. 26, Jun. 29, 2010, pp. 11906-11911, DOI: 10.1073/pnas.1002569107 (7 pages).

Kuen, Martin Matthias, "Antibody masked cytokines as new approach in targeted tumor therapy", Doctoral Dissertation, Aug. 2015 (126 pages).

Lehninger, Albert L., "Biochemistry: The molecular basis of cell structure and function", Second Edition, Ch. 4, 1975, Worth Publishers, New York, pp. 73-75 (4 pages).

Lindmark, Roger, et al., "Binding of Immunoglobulins to Protein A and Immunoglobulin Levels in Mammalian Sera", Journal of Immunological Methods, vol. 62, 1983, pp. 1-13 (13 pages).

Lode, Holger N., et al., "Targeted Therapy with a Novel Enediyene Antibiotic Calicheamicin ΘI1, Effectively Suppresses Growth and Dissemination of Liver Metastases in a Syngeneic Model of Murine Neuroblastoma", Cancer Research, vol. 58, Jul. 15, 1998, pp. 2925-2928 (4 pages).

Lonberg, Nils, et al., "Antigen-specific human antibodies from mice comprising four distinct genetic modifications", Nature, vol. 368, Apr. 28, 1994, pp. 856-859 (5 pages).

Mather, Jennie P., et al., "Culture of Testicular Cells in Hormone-Supplemented Serum-Free Medium", Annals New York Academy of Sciences, vol. 383, 1982, pp. 44-68 (25 pages).

Mather, Jennie P., "Establishment and Characterization of Two Distinct Mouse Testicular Epithelial Cell Lines", Biology of Reproduction, vol. 23, 1980, pp. 243-252 (10 pages).

Merchant, A. Margaret, et al., "An efficient route to human bispecific IgG", Nature Biotechnology, vol. 16, No. 7, Jul. 1998, pp. 677-681 (5 pages).

Milstein, C., et al., "Hybrid hybridomas and their use in immunohistochemistry", Nature, vol. 305, Oct. 6, 1983, pp. 537-540 (4 pages).

Moore, Gregory L., et al., "A novel bispecific antibody format enables simultaneous bivalent and monovalent co-engagement of distinct target antigens", mAbs, vol. 3, No. 6, Nov. 2011, pp. 546-557, DOI: 10.4161/mabs.3.6.18123 (12 pages).

Mori, Katsuhiro, et al., "Engineering Chinese Hamster Ovary Cells to Maximize Effector Function of Produced Antibodies Using FUT8 siRNA", Biotechnology and Bioengineering, vol. 88, No. 7, Dec. 30, 2004, pp. 901-908 (8 pages).

Morimoto, Koichi, et al., "Single-step purification of F(ab')2 fragments of mouse monoclonal antibodies (immunoglobulins G1) by hydrophobic interaction high performance liquid chromatography using TSKgel Phenyl-5PW", Journal of Biochemical and Biophysical Methods, vol. 24, 1992, pp. 107-117 (11 pages).

Nagy, Attila, et al., "Stability of cytotoxic luteinizing hormone-releasing hormone conjugate (AN-152) containing doxorubicin 14-O-hemiglutarate in mouse and human serum in vitro: Implications for the design of preclinical studies", Proceedings of the National Academy of Sciences USA, vol. 97, 2000, pp. 829-834 (6 pages).

Nilvebrant, Johan, et al., "The albumin-binding domain as a scaffold for protein engineering", Computational and Structural Biotechnology Journal, vol. 6, No. 7, Mar. 2013, pp. e201303009, DOI: 10.5936/csbj.201303009 (8 pages).

Nygren, Per-Åke, et al., "Analysis and Use of the Serum Albumin Binding Domains of Streptococcal Protein G", Journal of Molecular Recognition, vol. 1, No. 2, 1988, pp. 69-74 (6 pages).

O'Donoghue, Anthony J., et al., "Global Identification of Peptidase Specificity by Multiplex Substrate Profiling", Nature Methods, vol. 9, No. 11, Nov. 2012, pp. 1095-1100, DOI: doi:10.1038/nmeth. 2182, Author Manuscript (18 pages).

Okazaki, Akira, et al., "Fucose Depletion from Human IgG1 Oligosaccharide Enhances Binding Enthalpy and Association Rate Between IgG1 and FcγRIIIa", Journal of Molecular Biology, vol. 336, 2004, pp. 1239-1249, DOI: 10.1016/j.jmb.2004.01.007 (11 pages).

Omasa, Takeshi, et al., "Decrease in Antithrombin III Fucosylation by Expressing GDP-fucose Transporter siRNA in Chinese Hamster Ovary Cells", Journal of Bioscience and Bioengineering, vol. 106, No. 2, 2008, pp. 168-173, DOI: 10.1263/jbb.106.168 (6 pages).

Podust, Vladimir N., et al., "Extension of in vivo half-life of biologically active molecules by XTEN protein polymers", Journal of Controlled Release, vol. 240, 2016, pp. 52-66, DOI: 10.1016/j.jconrel.2015.10.038 (15 pages).

Proba, Karl, et al., "Functional antibody single-chain fragments from the cytoplasm of *Escherichia coli*: influence of thioredoxin reductase (TrxB)", Gene, vol. 159, 1995, pp. 203-207 (6 pages).

(56)　　　　　References Cited

OTHER PUBLICATIONS

Puskas, John, et al., "Development of an attenuated interleukin-2 fusion protein that can be activated by tumour-expressed proteases", Immunology, vol. 133, 2011, pp. 206-220, DOI: 10.1111/j.1365-2567.2011.0342.x (15 pages).

Ramm, Kathrin, et al., "The Periplasmic *Escherichia coli* Peptidylprolyl cis, trans-Isomerase FkpA", The Journal of Biological Chemistry, vol. 276, No. 22, Jun. 2, 2000, pp. 17106-17113, DOI: 10.1074/jbc.M910234199 (9 pages).

Reyes, Gregory R., et al., "Expression of human ß-interferon cDNA under the control of a thymidine kinase promoter from herpes simplex virus", Nature, vol. 297, Jun. 17, 1982, pp. 598-601 (4 pages).

Ridgway, John B.B., et al., "'Knobs-into-holes' engineering of antibody CH3 domains for heavy chain heterodimerization", Protein Engineering, vol. 9, No. 7, 1996, pp. 617-621 (5 pages).

Riechmann, Lutz, et al., "Reshaping human antibodies for therapy", Nature, vol. 332, 1988, pp. 323-327, DOI: 10.1038/332323a0 (5 pages).

Ripka, James, et al., "Two Chinese Hamster Ovary Glycosylation Mutants Affected in the Conversion of GDP-Mannose to GDP-Fucose", Archives of Biochemistry and Biophysics, vol. 249, No. 2, Sep. 1986, pp. 533-545 (13 pages).

Roux, Kenneth H., et al., "Comparisons of the Ability of Human IgG3 Hinge Mutants, IgM, IgE, and IgA2, to Form Small Immune Complexes: A Role for Flexibility and Geometry", The Journal of Immunology, vol. 161, 1998, pp. 4083-4090 (9 pages).

Sali, Tina M., et al., "Characterization of a Novel Human-Specific Sting Agonist that Elicits Antiviral Activity Against Emerging Alphaviruses", PLOS Pathogens, vol. 11, No. 12, e1005324, Dec. 8, 2015, DOI: 10.1371/journal.ppat.1005324 (30 pages).

Santollani, Luciano, et al., "Spatiotemporally programming cytokine immunotherapies through protein engineering.", Immunological Reviews, Wiley-Blackwell Publishing, Inc., US, vol. 320, No. 1, Jul. 6, 2023 (19 pages).

Schlapschy, Martin, et al., "PASylation: a biological alternative to PEGylation for extending the plasma half-life of pharmaceutically active proteins", Protein Engineering, Design & Selection, vol. 26, No. 8, 2013, pp. 489-501, DOI: 10.1093/protein/gzt023 (13 pages).

Shields, Robert L., et al., "Lack of Fucose on Human IgG1 N-Linked Oligosaccharide Improves Binding to Human FcγRIII and Antibody-dependent Cellular Toxicity", The Journal of Biological Chemistry, vol. 277, No. 30, Jul. 26, 2002, pp. 26733-26740, DOI: 10.1074/jbc.M202069200 (8 pages).

Shields, Robert L., et al., "High Resolution Mapping of the Binding Site on Human IgG1 for FcγRI, FcγRII, FcγRIII, and FcRn and Design of IgG1 Variants with Improved Binding to the FcγR", The Journal of Biological Chemistry, vol. 276, No. 9, Mar. 2, 2001, pp. 6591-6604, DOI: 10.1074/jbc.M009483200 (14 pages).

Shinkawa, et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity", The Journal of Biological Chemistry, vol. 278, No. 5, Jan. 31, 2003, pp. 3466-3473, DOI: 10.1074/jbc.M210665200 (8 pages).

Siebenlist, Ulrich, et al., "*E. coli* RNA Polymerase Interacts Homologously with Two Different Promoters", Cell, vol. 20, Jun. 1980, pp. 269-281 (13 pages).

Simmons, Laura C., et al., "Expression of full-length immunoglobulins in *Escherichia coli*: rapid and efficient production of aglycosylated antibodies", Journal of Immunological Methods, vol. 263, 2002, pp. 133-147 (15 pages).

Skrombolas, Denise, et al., "Development of an Interleukin-12 Fusion Protein That Is Activated by Cleavage with Matrix Metalloproteinase 9", Journal of Interferon & Cytokine Research, vol. 39, No. 4, Apr. 1, 2019, pp. 233-245 (13 pages).

Solá, R. J., et al., "Modulation of protein biophysical properties by chemical glycosylation: biochemical insights and biomedical implications", Cellular and Molecular Life Sciences, vol. 64, 2007, pp. 2133-2152, DOI: 10.1007/s00018-007-6551-y (20 pages).

Solá, Ricardo J., et al., "Effects of Glycosylation on the Stability of Protein Pharmaceuticals", J Pharm Sci, vol. 98, No. 4, Apr. 2009, pp. 1223-1245, DOI: 10.1002/jps.21504, Author Manuscript (32 pages).

Suresh, M. R., et al., "Bispecific Monoclonal Antibodies from Hybrid Hybridomas", Methods in Enzymology, vol. 121, 1986, pp. 210-228 (19 pages).

Tomizuka, Kazuma, et al., "Double trans-chromosomic mice: Maintenance of two individual human chromosome fragments containing Ig heavy and k loci and expression of fully human antibodies", Proceedings of the National Academy of Sciences, vol. 97, No. 2, Jan. 18, 2000, pp. 722-727 (6 pages).

Torgov, Michael Y., et al., "Generation of an Intensely Potent Anthracycline by a Monoclonal Antibody-ß-Galactosidase Conjugate", Bioconjugate Chem, vol. 16, 2005, pp. 717-721, DOI: 10.1021/bc050039z (5 pages).

Traunecker, Andre, et al., "Bispecific single chain molecules (Janusins) target cytotoxic lymphocytes on HIV infected cells", The EMBO Journal, vol. 10, No. 12, 1991, pp. 3655-3659 (5 pages).

Urlaub, Gail, et al., "Isolation of Chinese hamster cell mutants deficient in dihydrofolate reductase activity", Proceedings of the National Academy of Sciences USA, Genetics, vol. 77, No. 7, Jul. 1980, pp. 4216-4220 (5 pages).

Verhoeyen, Martine, et al., "Reshaping Human Antibodies: Grafting an Antilysozyme Activity", Science, vol. 239, No. 4847, Mar. 25, 1988, pp. 1534-1536 (4 pages).

Vitetta, Ellen S., et al., "Redesigning Nature's Poisons to Create Anti-Tumor Reagents", Science, vol. 238, Nov. 20, 1987, pp. 1098-1104 (7 pages).

Wüest, Thomas, et al., "TNF-Selectokine: a novel prodrug generated for tumor targeting and site-specific activation of tumor necrosis factor", Oncogene, vol. 21, 2002, pp. 4257-4265 (9 pages).

Yamane-Ohnuki, Naoko, et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity", Biotechnology and Bioengineering, vol. 87, No. 5, Sep. 5, 2004, pp. 614-622 (9 pages).

Yamane-Ohnuki, Naoko, et al., "Production of therapeutic antibodies with controlled fucosylation", mAbs, vol. 1, No. 3, May 2009, pp. 230-236, DOI: 10.4161/mabs.1.3.8328 (8 pages).

Yang, Karen, et al., "Tailoring structure-function and pharmacokinetic properties of single-chain Fv proteins by site-specific PEGylation", Protein Engineering, vol. 16, No. 10, 2003, pp. 761-770, DOI: 10.1093/protein/gzg093 (10 pages).

Yaniv, Moshe, "Enhancing elements for activation of eukaryotic promoters", Nature, vol. 297, May 6, 1982, pp. 17-18 (2 pages).

Yeung, Yik Andy, et al., "Engineering Human IgG1 Affinity to Human Neonatal Fc Receptor: Impact of Affinity Improvement on Pharmacokinetics in Primates", The Journal of Immunology, vol. 182, 2009, pp. 7667-7671, DOI: 10.4049/jimmunol.0804182 (9 pages).

Zaman, Rahela, et al., "Current strategies in extending half-lives of therapeutic proteins", Journal of Controlled Release 301 (2019) pp. 176-189 (14 pages).

Zapata, Gerardo, et al., "Engineering linear F(ab')2 fragments for efficient production in *Escherichia coli* and enhanced antiproliferative activity", Protein Engineering, vol. 8, No. 10, 1995, pp. 1057-1062 (6 pages).

| Test Article | Dose Level | Estimated t₁/₂ (days) (±SD) | Cmax (ug/mL) (±SD) | AUCₗₐₛₜ (hr*ug/mL) (±SD) | CLₒₐₛ (mL/hr/kg) (±SD) |
|---|---|---|---|---|---|
| UCM12 | 10 mg/kg (n=4) | 6.3 (±0.4) | 102 (±39.1) | 7490 (±2000) | 1.06 (±0.414) |
| | 3 mg/kg (n=5) | 6.0 (±1.5) | 26.0 (±3.72) | 2000 (±192) | 1.13 (±0.165) |
| | 1 mg/kg (n=5) | 6.0 (±1.7) | 12.8 (±1.91) | 1180 (±32.1) | 0.668 (±0.0738) |
| Control UCM1 | 9.15 mg/kg (n=5) | 1.4 (±1.0) | 105 (±18) | 1630 (±237) | 5.5 (±0.825) |
| | 2.75 mg/kg (n=5) | 1.3 (±0.4) | 29.7 (±4.18) | 713 (±41.3) | 3.77 (±0.212) |
| | 0.92 mg/kg (n=5) | 1.2 (±0.1) | 14.1 (±3.51) | 288 (±41.5) | 3.15 (±0.399) |

MASKED IL-2 CYTOKINES AND METHODS OF USE THEREOF

CROSS REFERENCE TO RELATED APPLICATIONS

This application is a Continuation of International Application No. PCT/US2025/011140, filed Jan. 10, 2025, which claims priority to U.S. Provisional Application No. 63/619,623 filed on Jan. 10, 2024, and U.S. Provisional Application No. 63/689,277 filed on Aug. 30, 2024; the contents of each of which are incorporated herein by reference in their entirety.

INCORPORATION OF SEQUENCE LISTING

This application contains a sequence listing filed electronically in XML format. The present application hereby incorporates by reference the entire contents of the XML file named "XTX_UNIVFC_03US2_SL.xml", which was created on Aug. 27, 2025, and is 70,179 bytes in size.

BACKGROUND

Cancer is the second leading cause of death in the United States, accounting for more deaths than the next five leading causes (chronic respiratory disease, stroke, accidents, Alzheimer's disease, and diabetes). While great strides have been made especially with targeted therapies, there remains a great deal of work to do in this space. Immunotherapy and a branch of this field, immuno-oncology, is creating viable and exciting therapeutic options for treating malignancies. Specifically, it is now recognized that one hallmark of cancer is immune evasion and significant efforts have identified targets and developed therapies to these targets to reactivate the immune system to recognize and treat cancer.

One effective strategy for stimulating the immune system to induce anti-tumor cytotoxicity is a cytokine therapy. Unfortunately, cytokines that are administered to patients generally have a very short half-life, thereby requiring frequent dosing. For instance, the product label of aldesleukin, marketed under the brand name Proleukin, states that the drug was shown to have a half-life of 85 minutes in patients who received a 5-minute intravenous (IV) infusion. In addition, administration of high doses of cytokine can cause adverse health outcomes, such as vascular leakage, through systemic immune activation. To extend half-life and reduce toxicity, carrier moieties such as an Fc domain, albumin, and PEG have been fused to the cytokine through a cleavable linker, which allows release of an active cytokine once the fused molecule reaches a tumor microenvironment.

SUMMARY OF INVENTION

The masked cytokine constructs described herein comprise an IL-2 cytokine, a VHH masking moiety, a targeting moiety, and an engineered Fc domain. In particular, the masked cytokines are engineered to optimize binding between the anti-IL-2 VHH masking moiety and the IL-2 cytokine to promote safe and effective targeted therapeutics for treating cancer. A VHH masking moiety binds to the IL-2 cytokine and inhibits a biological activity of the cytokine in undesired targets. Additionally, the Fc domain in the masked cytokine of the present invention is engineered to harbor a cleavage substrate. Upon cleavage in desired targets (e.g., tumor), the masking moiety is released from the cytokine, activating the function of the IL-2 polypeptide. In particular, the masked cytokine comprising an IL-2 and VHH masking moieties of the present invention is characterized with (1) effective masking efficiency such that IL-2 cytokine's function is inhibited in undesired targets; (2) efficient IL-2 activation by protease to release the VHH masking moiety; (3) selective IL-2 activation in tumor, and not in plasma; and (4) in vivo efficacy (e.g., high tumor growth inhibition).

In one aspect, the present invention provides, among other things, a masked cytokine comprising an IL-2 polypeptide, a masking moiety comprising a heavy-chain-only antibody (VHH), an anti-PD1 targeting moiety, and an engineered Fc domain comprising a first Fc polypeptide and a second Fc polypeptide, wherein the first Fc polypeptide comprises a tumor-associated protease cleavage site and is fused to the IL-2 polypeptide or the masking moiety such that the masking moiety binds to the IL-2 polypeptide and upon cleavage of the tumor-associated protease cleavage site in the first Fc polypeptide, the IL-2 polypeptide is released from the masking moiety.

In one aspect, the present invention provides, among other things, a masked cytokine comprising an IL-2 polypeptide, a masking moiety, a targeting moiety, and an engineered Fc domain comprising a first Fc polypeptide and a second Fc polypeptide, wherein the first Fc polypeptide comprises a tumor-associated protease cleavage site between positions 438-447 by EU numbering, wherein the first Fc polypeptide is fused to the IL-2 polypeptide or the masking moiety such that the masking moiety binds to the IL-2 polypeptide and upon cleavage of the tumor-associated protease cleavage site in the first Fc polypeptide, the IL-2 polypeptide is released from the masking moiety.

In one aspect, the present invention provides, among other things, a masked cytokine comprising an attenuated IL-2 polypeptide, a masking moiety, a targeting moiety, and an engineered Fc domain comprising a first Fc polypeptide and a second Fc polypeptide, wherein the first Fc polypeptide comprises a tumor-associated protease cleavage site of sequence PLGL (SEQ ID NO: 1); wherein the first Fc polypeptide is fused to the IL-2 polypeptide or the masking moiety such that the masking moiety binds to the IL-2 polypeptide and upon cleavage of the tumor-associated protease cleavage site in the first Fc polypeptide, the IL-2 polypeptide is released from the masking moiety.

In some embodiments, the first Fc polypeptide comprises a tumor-associated protease cleavage site of sequence SLPLGL (SEQ ID NO: 2). In some embodiments, the first Fc polypeptide comprises a tumor-associated protease cleavage site of sequence GGPLGL (SEQ ID NO: 3).

In some embodiments, the masking moiety comprises a heavy-chain-only antibody (VHH).

In some embodiments, the targeting moiety is an anti-PD1 targeting moiety.

In some embodiments, the targeting moiety is a scFv. In some embodiments, the targeting moiety is a Fab. In some embodiments, the targeting moiety is a VHH. In some embodiments, the targeting moiety is an antigen binding domain. In some embodiments, the targeting moiety is a single-domain antibody (sdAb). In some embodiments, the targeting moiety is diabody.

In some embodiments, the tumor-associated protease cleavage site is located between positions 444-447 by EU numbering. In some embodiments, the tumor-associated protease cleavage site is located between positions 440-447 by EU numbering. In some embodiments, the tumor-associated protease cleavage site is located between positions 438-447 by EU numbering. In some embodiments, the tumor-associated protease cleavage site is located between positions 438-446 by EU numbering. In some embodiments, the tumor-associated protease cleavage site is located between positions 442-447 by EU numbering. In some embodiments, the tumor-associated protease cleavage site is located in the G-strand of the Fc polypeptide.

In some embodiments, the tumor-associated cleavage site comprises amino acid sequence of PLGL (SEQ ID NO: 1). In some embodiments, the tumor-associated cleavage site comprises amino acid sequence of SLPLGL (SEQ ID NO: 2). In some embodiments, the tumor-associated cleavage site comprises amino acid sequence of GGPLGL (SEQ ID NO: 3). In some embodiments, the tumor-associated cleavage site comprises amino acid sequence of MPY (SEQ ID NO: 4). In some embodiments, the tumor-associated cleavage site comprises amino acid sequence of MPYDLYHP (SEQ ID NO: 5). In some embodiments, the tumor-associated cleavage site comprises amino acid sequence of APAG (SEQ ID NO: 6). In some embodiments, the tumor-associated cleavage site comprises amino acid sequence of APAGLIVPYN (SEQ ID NO: 7). In some embodiments, the tumor-associated cleavage site comprises amino acid sequence of PAN (SEQ ID NO: 8). In some embodiments, the tumor-associated cleavage site comprises amino acid sequence of PANLVAPDP (SEQ ID NO: 9).

In some embodiments, the engineered Fc polypeptide comprises amino acid substitutions of S442G, L443G, S444P, P445L and G447L by EU numbering. In some embodiments, the engineered Fc polypeptide comprises amino acid substitutions of S444P, P445L, and G447L by EU numbering. In some embodiments, the engineered Fc polypeptide comprises amino acid substitutions of S440M, L441P, S442Y, L443D, S444L, P445Y, G446H, and G447P by EU numbering. In some embodiments, the engineered Fc polypeptide comprises amino acid substitutions of Q438A, K439P, S440A, L441G, S442L, L443I, S444V, G446Y, and G447N by EU numbering. In some embodiments, the engineered Fc polypeptide comprises amino acid substitutions of Q438P, K439A, S440N, S442V, L443A, S444P, P445D, and G446P by EU numbering.

In some embodiments, the IL-2 comprises modifications R38A, F42A, Y45A, and E62A relative to the sequence of a mature IL-2 having SEQ ID NO: 10. In some embodiments, the IL-2 comprises a modification C125A relative to the sequence of a mature IL-2 having SEQ ID NO: 10. In some embodiments, the IL-2 comprises modifications F42E and C125A relative to the sequence of a mature IL-2 having SEQ ID NO: 10. In some embodiments, the IL-2 comprises a modification F42E relative to the sequence of a mature IL-2 having SEQ ID NO: 10.

In some embodiments, the VHH comprises a CDR1 of sequence GSIFSINVMG (SEQ ID NO: 14), a CDR2 of sequence AISSGGSTNYADSVKG (SEQ ID NO: 15), and a CDR3 of sequence ASSWYEDETDY (SEQ ID NO: 16). In some embodiments, the VHH comprises a CDR1 of sequence GSIFSINVMG (SEQ ID NO: 14), a CDR2 of sequence AISSGGSTNYADSVKG (SEQ ID NO: 15), and a CDR3 of sequence ASSFYEDETDY (SEQ ID NO: 17).

In one aspect, the present invention provides, among other things, a masked cytokine comprising an attenuated interleukin 2 (IL-2) polypeptide comprising an amino acid substitution of F42E and C125A, a VHH masking moiety comprising a CDR1 of sequence GSIFSINVMG (SEQ ID NO: 14), a CDR2 of sequence AISSGGSTNYADSVKG (SEQ ID NO: 15), and a CDR3 of sequence ASSWYEDE-TDY (SEQ ID NO: 16), an anti-PD1 targeting moiety, and an Fc domain comprising a first Fc polypeptide and a second Fc polypeptide, wherein the first Fc polypeptide comprises amino acid substitutions of S442G, L443G, S444P, P445L and G447L to engineer a tumor-associated protease cleavage site and the second Fc polypeptide does not comprise a tumor-associated protease cleavage site; and wherein the first Fc polypeptide is linked to the VHH masking moiety and the polypeptide Fc polypeptide is linked to the attenuated IL-2 polypeptide.

In one aspect, the present invention provides, among other things, an attenuated interleukin 2 (IL-2) polypeptide comprising an amino acid substitution of F42E and C125A, a VHH masking moiety comprising a CDR1 of sequence GSIFSINVMG (SEQ ID NO: 14), a CDR2 of sequence AISSGGSTNYADSVKG (SEQ ID NO: 15), and a CDR3 of sequence ASSFYEDETDY (SEQ ID NO: 17), an anti-PD1 targeting moiety, and an Fc domain comprising a first Fc polypeptide and a second Fc polypeptide, wherein the first Fc polypeptide comprises amino acid substitutions of S444P, P445L and G447L to engineer a tumor-associated protease cleavage site and the second Fc polypeptide does not comprise a tumor-associated protease cleavage site; and wherein the first Fc polypeptide is linked to the VHH masking moiety and the second Fc polypeptide is linked to the attenuated IL-2 polypeptide.

In one aspect, the present invention provides, among other things, an attenuated interleukin 2 (IL-2) polypeptide comprising an amino acid substitution of R38A, F42A, Y45A, E62A and C125A, a VHH masking moiety comprising a CDR1 of sequence GSIFSINVMG (SEQ ID NO: 14), a CDR2 of sequence AISSGGSTNYADSVKG (SEQ ID NO: 15), and a CDR3 of sequence ASSWYEDETDY (SEQ ID NO: 16), an anti-PD1 targeting moiety, and an Fc domain comprising a first Fc polypeptide and a second Fc polypeptide, wherein the first Fc domain comprising amino acid substitutions of S444P, P445L and G447L to engineer a tumor-associated protease cleavage site and the second Fc polypeptide does not comprise a tumor-associated protease cleavage site; and wherein the first Fc domain is linked to the VHH masking moiety and the second Fc domain is linked to the attenuated IL-2 polypeptide.

In one aspect, the present invention provides, among other things, an attenuated interleukin 2 (IL-2) polypeptide comprising an amino acid substitution of R38A, F42A, Y45A, E62A and C125A, a VHH masking moiety comprising a CDR1 of sequence GSIFSINVMG (SEQ ID NO: 14), a CDR2 of sequence AISSGGSTNYADSVKG (SEQ ID NO: 15), and a CDR3 of sequence ASSWYEDETDY (SEQ ID NO: 16), an anti-PD1 targeting moiety, and an Fc domain comprising a first Fc polypeptide and a second Fc polypeptide, wherein the first Fc domain comprising amino acid substitutions of S440M, L441P, S442Y, L443D, S444L, P445Y, G446H, and G447P to engineer a tumor-associated protease cleavage site and the second Fc polypeptide does not comprise a tumor-associated protease cleavage site; and wherein the first Fc domain is linked to the VHH masking moiety and the second Fc domain is linked to the attenuated IL-2 polypeptide.

In some embodiments, the VHH comprises one or more amino acid extension at C-terminus. In some embodiments, the VHH comprises an alanine extension at C-terminus. In some embodiments, the VHH comprises amino acid sequence of AAA (SEQ ID NO: 18) at the C-terminus.

In some embodiments, the VHH comprises an amino acid sequence of

```
                                        (SEQ ID NO: 19)
EVQLVESGGGLVQPGGSLRLSCAASGSIFSINVMGWYRQAPGKQR

ELVAAISSGGSTNYADSVKGRFTISRDNAKNTVYLQMNSLKPEDT

AVYYCMYASSWYEDETDYWGQGTQVTVSS.
```

In some embodiments, the VHH comprises an amino acid sequence of

```
                                        (SEQ ID NO: 21)
EVQLVESGGGLVQPGGSLRLSCAASGSIFSINVMGWYRQAPGKQR

ELVAAISSGGSTNYADSVKGRFTISRDNAKNTVYLQMNSLKPEDT

AVYYCMYASSWYEDETDYWGQGTQVTVSSAAA.
```

In some embodiments, the VHH comprises an amino acid sequence of

```
                                        (SEQ ID NO: 20)
EVQLVESGGGLVQPGGSLRLSCAASGSIFSINVMGWYRQAPGKGR

ELVAAISSGGSTNYADSVKGRFTISRDNAKNTVYLQMNSLKPEDT

AVYYCAYASSFYEDETDYWGQGTQVTVSS.
```

In some embodiments, the targeting moiety comprises a heavy chain CDR1 sequence of GYTFTNYY (SEQ ID NO: 43), a heavy chain CDR2 sequence of INPSNGGT (SEQ ID NO: 44), a heavy chain CDR3 sequence of ARRDYRFDMGEDY (SEQ ID NO: 45), a light chain CDR1 sequence of KGVSTSGYSY (SEQ ID NO: 46), a light chain CDR2 sequence of LAS (SEQ ID NO: 47), and a light chain CDR3 sequence of QHSRDLPLT (SEQ ID NO: 48).

In some embodiments, the targeting moiety comprises a heavy chain region having an amino acid sequence at least about 80% identical to SEQ ID NO: 41. In some embodiments, the targeting moiety comprises a heavy chain region having an amino acid sequence at least about 82% identical to SEQ ID NO: 41. In some embodiments, the targeting moiety comprises a heavy chain region having an amino acid sequence at least about 85% identical to SEQ ID NO: 41. In some embodiments, the targeting moiety comprises a heavy chain region having an amino acid sequence at least about 86% identical to SEQ ID NO: 41. In some embodiments, the targeting moiety comprises a heavy chain region having an amino acid sequence at least about 88% identical to SEQ ID NO: 41. In some embodiments, the targeting moiety comprises a heavy chain region having an amino acid sequence at least about 90% identical to SEQ ID NO: 41. In some embodiments, the targeting moiety comprises a heavy chain region having an amino acid sequence at least about 92% identical to SEQ ID NO: 41. In some embodiments, the targeting moiety comprises a heavy chain region having an amino acid sequence at least about 94% identical to SEQ ID NO: 41. In some embodiments, the targeting moiety comprises a heavy chain region having an amino acid sequence at least about 95% identical to SEQ ID NO: 41. In some embodiments, the targeting moiety comprises a heavy chain region having an amino acid sequence at least about 96% identical to SEQ ID NO: 41. In some embodiments, the targeting moiety comprises a heavy chain region having an amino acid sequence at least about 97% identical to SEQ ID NO: 41. In some embodiments, the targeting moiety comprises a heavy chain region having an amino acid sequence at least about 98% identical to SEQ ID NO:

41. In some embodiments, the targeting moiety comprises a heavy chain region having an amino acid sequence at least about 99% identical to SEQ ID NO: 41. In some embodiments, the targeting moiety comprises a heavy chain region having an amino acid sequence of SEQ ID NO: 41

In some embodiments, the targeting moiety comprises a heavy chain region having an amino acid sequence at least about 80% identical to SEQ ID NO: 42. In some embodiments, the targeting moiety comprises a heavy chain region having an amino acid sequence at least about 82% identical to SEQ ID NO: 42. In some embodiments, the targeting moiety comprises a heavy chain region having an amino acid sequence at least about 85% identical to SEQ ID NO: 42. In some embodiments, the targeting moiety comprises a heavy chain region having an amino acid sequence at least about 86% identical to SEQ ID NO: 42. In some embodiments, the targeting moiety comprises a heavy chain region having an amino acid sequence at least about 88% identical to SEQ ID NO: 42. In some embodiments, the targeting moiety comprises a heavy chain region having an amino acid sequence at least about 90% identical to SEQ ID NO: 42. In some embodiments, the targeting moiety comprises a heavy chain region having an amino acid sequence at least about 92% identical to SEQ ID NO: 42. In some embodiments, the targeting moiety comprises a heavy chain region having an amino acid sequence at least about 94% identical to SEQ ID NO: 42. In some embodiments, the targeting moiety comprises a heavy chain region having an amino acid sequence at least about 95% identical to SEQ ID NO: 42. In some embodiments, the targeting moiety comprises a heavy chain region having an amino acid sequence at least about 96% identical to SEQ ID NO: 42. In some embodiments, the targeting moiety comprises a heavy chain region having an amino acid sequence at least about 97% identical to SEQ ID NO: 42. In some embodiments, the targeting moiety comprises a heavy chain region having an amino acid sequence at least about 98% identical to SEQ ID NO: 42. In some embodiments, the targeting moiety comprises a heavy chain region having an amino acid sequence at least about 99% identical to SEQ ID NO: 42. In some embodiments, the targeting moiety comprises a heavy chain region having an amino acid sequence of SEQ ID NO: 42.

In some embodiments, the targeting moiety comprises a heavy chain variable region comprising SEQ ID NO: 41 and a light chain variable region comprising SEQ ID NO: 42.

In some embodiments, the second Fc polypeptide does not comprise the tumor-associated protease cleavage site.

In some embodiments, the first Fc polypeptide is linked to the IL-2 polypeptide, and the second Fc polypeptide is linked to the masking moiety. In some embodiments, the first Fc polypeptide is linked to the masking moiety, and the second Fc polypeptide is linked to the IL-2 polypeptide.

In some embodiments, the first Fc polypeptide comprises an amino acid substitution of N297A. In some embodiments, the first Fc polypeptide comprises amino acid substitutions of H435R and Y436F. In some embodiments, the first Fc polypeptide comprises amino acid substitutions of Y349C, T366S, L368A, and Y407V. In some embodiments, the first Fc polypeptide comprises amino acid substitutions of S354C and T366W. In some embodiments, the first Fc polypeptide comprises amino acid substitutions of N297A, S354C and T366W. In some embodiments, the first Fc polypeptide comprises amino acid substitutions of N297A, S354C, T366W, H435R and Y436F. In some embodiments, the first Fc polypeptide comprises amino acid substitutions of N297A, Y349C, T366S, L368A, and Y407V. In some embodiments, the first Fc polypeptide comprises amino acid substitutions of N297A, Y349C, T366S, L368A, Y407V, H435R and Y436F.

In some embodiments, the second Fc polypeptide comprises an amino acid substitution of N297A. In some embodiments, the second Fc polypeptide comprises amino acid substitutions of H435R and Y436F. In some embodiments, the second Fc polypeptide comprises amino acid substitutions of Y349C, T366S, L368A, and Y407V. In some embodiments, the second Fc polypeptide comprises amino acid substitutions of S354C and T366W. In some embodiments, the second Fc polypeptide comprises amino acid substitutions of N297A, S354C and T366W. In some embodiments, the second Fc polypeptide comprises amino acid substitutions of N297A, S354C, T366W, H435R and Y436F. In some embodiments, the second Fc polypeptide comprises amino acid substitutions of N297A, Y349C, T366S, L368A, and Y407V. In some embodiments, the second Fc polypeptide comprises amino acid substitutions of N297A, Y349C, T366S, L368A, Y407V, H435R and Y436F.

In some embodiments, the first Fc polypeptide comprises SEQ ID NO: 23, and the second Fc polypeptide comprises SEQ ID NO: 33. In some embodiments, the first Fc polypeptide comprises SEQ ID NO: 24, and the second Fc polypeptide comprises SEQ ID NO: 33. In some embodiments, the first Fc polypeptide comprises SEQ ID NO: 25, and the second Fc polypeptide comprises SEQ ID NO: 33. In some embodiments, the first Fc polypeptide comprises SEQ ID NO: 26, and the second Fc polypeptide comprises SEQ ID NO: 33. In some embodiments, the first Fc polypeptide comprises SEQ ID NO: 27, and the second Fc polypeptide comprises SEQ ID NO: 33.

In some embodiments, the second Fc polypeptide comprises SEQ ID NO: 23, and the first Fc polypeptide comprises SEQ ID NO: 33. In some embodiments, the second Fc polypeptide comprises SEQ ID NO: 24, and the first Fc polypeptide comprises SEQ ID NO: 33. In some embodiments, the second Fc polypeptide comprises SEQ ID NO: 25, and the first Fc polypeptide comprises SEQ ID NO: 33. In some embodiments, the second Fc polypeptide comprises SEQ ID NO: 26, and the first Fc polypeptide comprises SEQ ID NO: 33. In some embodiments, the second Fc polypeptide comprises SEQ ID NO: 27, and the first Fc polypeptide comprises SEQ ID NO: 33.

In one aspect, the present invention provides, among other things, a masked cytokine comprising an interleukin 2 (IL-2) polypeptide comprising an amino acid sequence that is at least 90% identical to SEQ ID NO: 13, a VHH masking moiety comprising an amino acid sequence that is at least 90% identical to SEQ ID NO: 19, an anti-PD1 targeting moiety comprising a variable heavy region (VH) that is at least 90% identical to SEQ ID NO: 41, and a variable light region (VL) that is at least 90% identical to SEQ ID NO: 42, a first Fc polypeptide comprising an amino acid sequence that is at least 90% identical to SEQ ID NO: 27, and a second Fc polypeptide comprising SEQ ID NO: 33, wherein the first Fc domain is linked to the VHH masking moiety and the second Fc domain is linked to the IL-2 polypeptide.

In one aspect, the present invention provides, among other things, an interleukin 2 (IL-2) polypeptide comprising an amino acid sequence that is at least 90% identical to SEQ ID NO: 13, a VHH masking moiety comprising an amino acid sequence that is at least 90% identical to SEQ ID NO: 21, an anti-PD1 targeting moiety comprising a variable heavy region (VH) that is at least 90% identical to SEQ ID NO: 41, and a variable light region (VL) that is at least 90% identical to SEQ ID NO: 42, a first Fc polypeptide comprising an amino acid sequence that is at least 90% identical to SEQ ID NO: 27 or SEQ ID NO: 23, and a second Fc polypeptide comprising SEQ ID NO: 33, wherein the first Fc domain is linked to the VHH masking moiety and the second Fc domain is linked to the IL-2 polypeptide.

In one aspect, the present invention provides, among other things, an interleukin 2 (IL-2) polypeptide comprising an amino acid sequence that is at least 90% identical to SEQ ID NO: 12, a VHH masking moiety comprising an amino acid sequence that is at least 90% identical to SEQ ID NO: 19, an anti-PD1 targeting moiety comprising a variable heavy region (VH) that is at least 90% identical to SEQ ID NO: 41, and a variable light region (VL) that is at least 90% identical to SEQ ID NO: 42, a first Fc polypeptide comprising an amino acid sequence that is at least 90% identical to SEQ ID NO: 23, SEQ ID NO: 24, SEQ ID NO: 25, or SEQ ID NO: 26 and a second Fc polypeptide comprising SEQ ID NO: 33, wherein the first Fc polypeptide is linked to the VHH masking moiety and the second Fc polypeptide is linked to the IL-2 polypeptide.

In one aspect, the present invention provides, among other things, an interleukin 2 (IL-2) polypeptide comprising an amino acid sequence that is at least 90% identical to SEQ ID NO: 11, a VHH masking moiety comprising an amino acid sequence that is at least 90% identical to SEQ ID NO: 19, an anti-PD1 targeting moiety comprising a variable heavy region (VH) that is at least 90% identical to SEQ ID NO: 41, and a variable light region (VL) that is at least 90% identical to SEQ ID NO: 42, a first Fc polypeptide comprising an amino acid sequence that is at least 90% identical to SEQ ID NO: 23, and a second Fc polypeptide comprising SEQ ID NO: 33, wherein the first Fc polypeptide is linked to the VHH masking moiety and the second Fc polypeptide is linked to the IL-2 polypeptide.

In some embodiments, the IL-2 polypeptide comprises an amino acid sequence that is at least 90% identical to SEQ ID NO: 11. In some embodiments, the IL-2 polypeptide comprises an amino acid sequence that is at least 92% identical to SEQ ID NO: 11. In some embodiments, the IL-2 polypeptide comprises an amino acid sequence that is at least 93% identical to SEQ ID NO: 11. In some embodiments, the IL-2 polypeptide comprises an amino acid sequence that is at least 94% identical to SEQ ID NO: 11. In some embodiments, the IL-2 polypeptide comprises an amino acid sequence that is at least 95% identical to SEQ ID NO: 11. In some embodiments, the IL-2 polypeptide comprises an amino acid sequence that is at least 96% identical to SEQ ID NO: 11. In some embodiments, the IL-2 polypeptide comprises an amino acid sequence that is at least 97% identical to SEQ ID NO: 11. In some embodiments, the IL-2 polypeptide comprises an amino acid sequence that is at least 98% identical to SEQ ID NO: 11. In some embodiments, the IL-2 polypeptide comprises an amino acid sequence that is at least 99% identical to SEQ ID NO: 11. In some embodiments, the IL-2 polypeptide comprises an amino acid sequence that is 100% identical to SEQ ID NO: 11.

In some embodiments, the IL-2 polypeptide comprises an amino acid sequence that is at least 90% identical to SEQ ID NO: 12. In some embodiments, the IL-2 polypeptide comprises an amino acid sequence that is at least 92% identical to SEQ ID NO: 12. In some embodiments, the IL-2 polypeptide comprises an amino acid sequence that is at least 93% identical to SEQ ID NO: 12. In some embodiments, the IL-2 polypeptide comprises an amino acid sequence that is at least 94% identical to SEQ ID NO: 12. In some embodiments, the IL-2 polypeptide comprises an amino acid sequence that is at least 95% identical to SEQ ID NO: 12. In some embodiments, the IL-2 polypeptide comprises an amino acid sequence that is at least 96% identical to SEQ ID NO: 12. In some embodiments, the IL-2 polypeptide comprises an amino acid sequence that is at least 97% identical to SEQ ID NO: 12. In some embodiments, the IL-2 polypeptide comprises an amino acid sequence that is at least 98% identical to SEQ ID NO: 12. In some embodiments, the IL-2 polypeptide comprises an amino acid sequence that is at least 99% identical to SEQ ID NO: 12. In some embodiments, the IL-2 polypeptide comprises an amino acid sequence that is 100% identical to SEQ ID NO: 12.

In some embodiments, the IL-2 polypeptide comprises an amino acid sequence that is at least 90% identical to SEQ ID NO: 13. In some embodiments, the IL-2 polypeptide comprises an amino acid sequence that is at least 92% identical to SEQ ID NO: 13. In some embodiments, the IL-2 polypeptide comprises an amino acid sequence that is at least 93% identical to SEQ ID NO: 13. In some embodiments, the IL-2 polypeptide comprises an amino acid sequence that is at least 94% identical to SEQ ID NO: 13. In some embodiments, the IL-2 polypeptide comprises an amino acid sequence that is at least 95% identical to SEQ ID NO: 13. In some embodiments, the IL-2 polypeptide comprises an amino acid sequence that is at least 96% identical to SEQ ID NO: 13. In some embodiments, the IL-2 polypeptide comprises an amino acid sequence that is at least 97% identical to SEQ ID NO: 13. In some embodiments, the IL-2 polypeptide comprises an amino acid sequence that is at least 98% identical to SEQ ID NO: 13. In some embodiments, the IL-2 polypeptide comprises an amino acid sequence that is at least 99% identical to SEQ ID NO: 13. In some embodiments, the IL-2 polypeptide comprises an amino acid sequence that is 100% identical to SEQ ID NO: 13.

In some embodiments, the VHH masking moiety comprises and amino acid that is at least 90% identical to SEQ ID NO: 19. In some embodiments, the VHH masking moiety comprises and amino acid that is at least 92% identical to SEQ ID NO: 19. In some embodiments, the VHH masking moiety comprises and amino acid that is at least 93% identical to SEQ ID NO: 19. In some embodiments, the VHH masking moiety comprises and amino acid that is at least 94% identical to SEQ ID NO: 19. In some embodiments, the VHH masking moiety comprises and amino acid that is at least 95% identical to SEQ ID NO: 19. In some embodiments, the VHH masking moiety comprises and amino acid that is at least 96% identical to SEQ ID NO: 19. In some embodiments, the VHH masking moiety comprises and amino acid that is at least 97% identical to SEQ ID NO: 19. In some embodiments, the VHH masking moiety comprises and amino acid that is at least 98% identical to SEQ ID NO: 19. In some embodiments, the VHH masking moiety comprises and amino acid that is at least 99% identical to SEQ ID NO: 19. In some embodiments, the VHH masking moiety comprises and amino acid that is 100% identical to SEQ ID NO: 19.

In some embodiments, the VHH masking moiety comprises and amino acid that is at least 90% identical to SEQ ID NO: 20. In some embodiments, the VHH masking moiety comprises and amino acid that is at least 92% identical to SEQ ID NO: 20. In some embodiments, the VHH masking moiety comprises and amino acid that is at least 93% identical to SEQ ID NO: 20. In some embodiments, the VHH masking moiety comprises and amino acid that is at least 94% identical to SEQ ID NO: 20. In some embodiments, the VHH masking moiety comprises and amino acid that is at least 95% identical to SEQ ID NO: 20. In some embodiments, the VHH masking moiety comprises and amino acid that is at least 96% identical to SEQ ID NO: 20. In some embodiments, the VHH masking moiety comprises and amino acid that is at least 97% identical to SEQ ID NO: 20. In some embodiments, the VHH masking moiety comprises and amino acid that is at least 98% identical to SEQ ID NO: 20. In some embodiments, the VHH masking moiety comprises and amino acid that is at least 99% identical to SEQ ID NO: 20. In some embodiments, the VHH masking moiety comprises and amino acid that is 100% identical to SEQ ID NO: 20.

In some embodiments, the VHH masking moiety comprises and amino acid that is at least 90% identical to SEQ ID NO: 21. In some embodiments, the VHH masking moiety comprises and amino acid that is at least 92% identical to SEQ ID NO: 21. In some embodiments, the VHH masking moiety comprises and amino acid that is at least 93% identical to SEQ ID NO: 21. In some embodiments, the VHH masking moiety comprises and amino acid that is at least 94% identical to SEQ ID NO: 21. In some embodiments, the VHH masking moiety comprises and amino acid that is at least 95% identical to SEQ ID NO: 21. In some embodiments, the VHH masking moiety comprises and amino acid that is at least 96% identical to SEQ ID NO: 21. In some embodiments, the VHH masking moiety comprises and amino acid that is at least 97% identical to SEQ ID NO: 21. In some embodiments, the VHH masking moiety comprises and amino acid that is at least 98% identical to SEQ ID NO: 21. In some embodiments, the VHH masking moiety comprises and amino acid that is at least 99% identical to SEQ ID NO: 21. In some embodiments, the VHH masking moiety comprises and amino acid that is 100% identical to SEQ ID NO: 21.

In some embodiments, the VHH masking moiety comprises and amino acid that is at least 90% identical to SEQ ID NO: 22. In some embodiments, the VHH masking moiety comprises and amino acid that is at least 92% identical to SEQ ID NO: 22. In some embodiments, the VHH masking moiety comprises and amino acid that is at least 93% identical to SEQ ID NO: 22. In some embodiments, the VHH masking moiety comprises and amino acid that is at least 94% identical to SEQ ID NO: 22. In some embodiments, the VHH masking moiety comprises and amino acid that is at least 95% identical to SEQ ID NO: 22. In some embodiments, the VHH masking moiety comprises and amino acid that is at least 96% identical to SEQ ID NO: 22. In some embodiments, the VHH masking moiety comprises and amino acid that is at least 97% identical to SEQ ID NO: 22. In some embodiments, the VHH masking moiety comprises and amino acid that is at least 98% identical to SEQ ID NO: 22. In some embodiments, the VHH masking moiety comprises and amino acid that is at least 99% identical to SEQ ID NO: 22. In some embodiments, the VHH masking moiety comprises and amino acid that is 100% identical to SEQ ID NO: 22.

In some embodiments, the first Fc polypeptide comprises an amino acid sequence that is 90% identical to SEQ ID NO: 23. In some embodiments, the first Fc polypeptide comprises an amino acid sequence that is 92% identical to SEQ ID NO: 23. In some embodiments, the first Fc polypeptide comprises an amino acid sequence that is 93% identical to SEQ ID NO: 23. In some embodiments, the first Fc polypeptide comprises an amino acid sequence that is 94% identical to SEQ ID NO: 23. In some embodiments, the first Fc polypeptide comprises an amino acid sequence that is 95% identical to SEQ ID NO: 23. In some embodiments, the first Fc polypeptide comprises an amino acid sequence that is 96% identical to SEQ ID NO:

23. In some embodiments, the first Fc polypeptide comprises an amino acid sequence that is 97% identical to SEQ ID NO: 23. In some embodiments, the first Fc polypeptide comprises an amino acid sequence that is 98% identical to SEQ ID NO: 23. In some embodiments, the first Fc polypeptide comprises an amino acid sequence that is 99% identical to SEQ ID NO: 23. In some embodiments, the first Fc polypeptide comprises an amino acid sequence that is 100% identical to SEQ ID NO: 23.

In some embodiments, the first Fc polypeptide comprises an amino acid sequence that is 90% identical to SEQ ID NO: 24. In some embodiments, the first Fc polypeptide comprises an amino acid sequence that is 92% identical to SEQ ID NO: 24. In some embodiments, the first Fc polypeptide comprises an amino acid sequence that is 93% identical to SEQ ID NO: 24. In some embodiments, the first Fc polypeptide comprises an amino acid sequence that is 94% identical to SEQ ID NO: 24. In some embodiments, the first Fc polypeptide comprises an amino acid sequence that is 95% identical to SEQ ID NO: 24. In some embodiments, the first Fc polypeptide comprises an amino acid sequence that is 96% identical to SEQ ID NO: 24. In some embodiments, the first Fc polypeptide comprises an amino acid sequence that is 97% identical to SEQ ID NO: 24. In some embodiments, the first Fc polypeptide comprises an amino acid sequence that is 98% identical to SEQ ID NO: 24. In some embodiments, the first Fc polypeptide comprises an amino acid sequence that is 99% identical to SEQ ID NO: 24. In some embodiments, the first Fc polypeptide comprises an amino acid sequence that is 100% identical to SEQ ID NO: 24.

In some embodiments, the first Fc polypeptide comprises an amino acid sequence that is 90% identical to SEQ ID NO: 25. In some embodiments, the first Fc polypeptide comprises an amino acid sequence that is 92% identical to SEQ ID NO: 25. In some embodiments, the first Fc polypeptide comprises an amino acid sequence that is 93% identical to SEQ ID NO: 25. In some embodiments, the first Fc polypeptide comprises an amino acid sequence that is 94% identical to SEQ ID NO: 25. In some embodiments, the first Fc polypeptide comprises an amino acid sequence that is 95% identical to SEQ ID NO: 25. In some embodiments, the first Fc polypeptide comprises an amino acid sequence that is 96% identical to SEQ ID NO: 25. In some embodiments, the first Fc polypeptide comprises an amino acid sequence that is 97% identical to SEQ ID NO: 25. In some embodiments, the first Fc polypeptide comprises an amino acid sequence that is 98% identical to SEQ ID NO: 25. In some embodiments, the first Fc polypeptide comprises an amino acid sequence that is 99% identical to SEQ ID NO: 25. In some embodiments, the first Fc polypeptide comprises an amino acid sequence that is 100% identical to SEQ ID NO: 25.

In some embodiments, the first Fc polypeptide comprises an amino acid sequence that is 90% identical to SEQ ID NO: 26. In some embodiments, the first Fc polypeptide comprises an amino acid sequence that is 92% identical to SEQ ID NO: 26. In some embodiments, the first Fc polypeptide comprises an amino acid sequence that is 93% identical to SEQ ID NO: 26. In some embodiments, the first Fc polypeptide comprises an amino acid sequence that is 94% identical to SEQ ID NO: 26. In some embodiments, the first Fc polypeptide comprises an amino acid sequence that is 95% identical to SEQ ID NO: 26. In some embodiments, the first Fc polypeptide comprises an amino acid sequence that is 96% identical to SEQ ID NO: 26. In some embodiments, the first Fc polypeptide comprises an amino acid sequence that is 97% identical to SEQ ID NO: 26. In some embodiments, the first Fc polypeptide comprises an amino acid sequence that is 98% identical to SEQ ID NO:

26. In some embodiments, the first Fc polypeptide comprises an amino acid sequence that is 99% identical to SEQ ID NO: 26. In some embodiments, the first Fc polypeptide comprises an amino acid sequence that is 100% identical to SEQ ID NO: 26.

In some embodiments, the first Fc polypeptide comprises an amino acid sequence that is 90% identical to SEQ ID NO: 27. In some embodiments, the first Fc polypeptide comprises an amino acid sequence that is 92% identical to SEQ ID NO: 27. In some embodiments, the first Fc polypeptide comprises an amino acid sequence that is 93% identical to SEQ ID NO: 27. In some embodiments, the first Fc polypeptide comprises an amino acid sequence that is 94% identical to SEQ ID NO: 27. In some embodiments, the first Fc polypeptide comprises an amino acid sequence that is 95% identical to SEQ ID NO: 27. In some embodiments, the first Fc polypeptide comprises an amino acid sequence that is 96% identical to SEQ ID NO: 27. In some embodiments, the first Fc polypeptide comprises an amino acid sequence that is 97% identical to SEQ ID NO: 27. In some embodiments, the first Fc polypeptide comprises an amino acid sequence that is 98% identical to SEQ ID NO: 27. In some embodiments, the first Fc polypeptide comprises an amino acid sequence that is 99% identical to SEQ ID NO: 27. In some embodiments, the first Fc polypeptide comprises an amino acid sequence that is 100% identical to SEQ ID NO: 27.

In some embodiments, the first Fc polypeptide comprises an amino acid sequence that is 90% identical to SEQ ID NO: 33. In some embodiments, the first Fc polypeptide comprises an amino acid sequence that is 92% identical to SEQ ID NO: 33. In some embodiments, the first Fc polypeptide comprises an amino acid sequence that is 93% identical to SEQ ID NO: 33. In some embodiments, the first Fc polypeptide comprises an amino acid sequence that is 94% identical to SEQ ID NO: 33. In some embodiments, the first Fc polypeptide comprises an amino acid sequence that is 95% identical to SEQ ID NO: 33. In some embodiments, the first Fc polypeptide comprises an amino acid sequence that is 96% identical to SEQ ID NO: 33. In some embodiments, the first Fc polypeptide comprises an amino acid sequence that is 97% identical to SEQ ID NO: 33. In some embodiments, the first Fc polypeptide comprises an amino acid sequence that is 98% identical to SEQ ID NO: 33. In some embodiments, the first Fc polypeptide comprises an amino acid sequence that is 99% identical to SEQ ID NO: 33. In some embodiments, the first Fc polypeptide comprises an amino acid sequence that is 100% identical to SEQ ID NO: 33.

In one aspect, the present invention provides, among other things, a masked cytokine comprising a first polypeptide comprising an amino acid sequence that is at least 90% identical to SEQ ID NO: 63, a second polypeptide comprising an amino acid sequence that is at least 90% identical to SEQ ID NO: 74, a third polypeptide comprising an amino acid sequence that is at least 90% identical to SEQ ID NO: 50.

In one aspect, the present invention provides, among other things, a masked cytokine comprising a first polypeptide comprising an amino acid sequence that is at least 90% identical to SEQ ID NO: 64, a second polypeptide comprising an amino acid sequence that is at least 90% identical to SEQ ID NO: 66, a third polypeptide comprising an amino acid sequence that is at least 90% identical to SEQ ID NO: 50.

In one aspect, the present invention provides, among other things, a masked cytokine comprising a first polypeptide comprising an amino acid sequence that is at least 90% identical to SEQ ID NO: 65, a second polypeptide comprising an amino acid sequence that is at least 90% identical to SEQ ID NO: 66, a third polypeptide comprising an amino acid sequence that is at least 90% identical to SEQ ID NO: 50.

In one aspect, the present invention provides, among other things, a masked cytokine comprising a first polypeptide comprising an amino acid sequence that is at least 90% identical to SEQ ID NO: 63, a second polypeptide comprising an amino acid sequence that is at least 90% identical to SEQ ID NO: 66, a third polypeptide comprising an amino acid sequence that is at least 90% identical to SEQ ID NO: 50.

In one aspect, the present invention provides, among other things, a masked cytokine comprising a first polypeptide comprising an amino acid sequence that is at least 90% identical to SEQ ID NO: 65, a second polypeptide comprising an amino acid sequence that is at least 90% identical to SEQ ID NO: 68, a third polypeptide comprising an amino acid sequence that is at least 90% identical to SEQ ID NO: 50.

In one aspect, the present invention provides, among other things, a masked cytokine comprising a first polypeptide comprising an amino acid sequence that is at least 90% identical to SEQ ID NO: 65, a second polypeptide comprising an amino acid sequence that is at least 90% identical to SEQ ID NO: 69, a third polypeptide comprising an amino acid sequence that is at least 90% identical to SEQ ID NO: 50.

In one aspect, the present invention provides, among other things, a masked cytokine comprising a first polypeptide comprising an amino acid sequence that is at least 90% identical to SEQ ID NO: 65, a second polypeptide comprising an amino acid sequence that is at least 90% identical to SEQ ID NO: 70, a third polypeptide comprising an amino acid sequence that is at least 90% identical to SEQ ID NO: 50.

In one aspect, the present invention provides, among other things, a masked cytokine comprising a first polypeptide comprising an amino acid sequence that is at least 90% identical to SEQ ID NO: 65, a second polypeptide comprising an amino acid sequence that is at least 90% identical to SEQ ID NO: 67, a third polypeptide comprising an amino acid sequence that is at least 90% identical to SEQ ID NO: 50.

In one aspect, the present invention provides, among other things, a masked cytokine comprising a first polypeptide comprising an amino acid sequence that is at least 90% identical to SEQ ID NO: 65, a second polypeptide comprising an amino acid sequence that is at least 90% identical to SEQ ID NO: 71, a third polypeptide comprising an amino acid sequence that is at least 90% identical to SEQ ID NO: 50.

In one aspect, the present invention provides, among other things, a masked cytokine comprising a first polypeptide comprising an amino acid sequence that is at least 90% identical to SEQ ID NO: 63, a second polypeptide comprising an amino acid sequence that is at least 90% identical to SEQ ID NO: 72, a third polypeptide comprising an amino acid sequence that is at least 90% identical to SEQ ID NO: 50.

In one aspect, the present invention provides, among other things, a masked cytokine comprising a first polypeptide comprising an amino acid sequence that is at least 90% identical to SEQ ID NO: 63, a second polypeptide comprising an amino acid sequence that is at least 90% identical to SEQ ID NO: 73, a third polypeptide comprising an amino acid sequence that is at least 90% identical to SEQ ID NO: 50.

In one aspect, the present invention provides, among other things, a masked cytokine comprising a first polypeptide comprising an amino acid sequence that is at least 90% identical to SEQ ID NO: 63, a second polypeptide comprising an amino acid sequence that is at least 90% identical to SEQ ID NO: 67, a third polypeptide comprising an amino acid sequence that is at least 90% identical to SEQ ID NO: 50.

In some embodiments, the first polypeptide comprises an amino acid sequence that is at least 92% identical to SEQ ID NO: 63. In some embodiments, the first polypeptide comprises an amino acid sequence that is at least 93% identical to SEQ ID NO: 63. In some embodiments, the first polypeptide comprises an amino acid sequence that is at least 94% identical to SEQ ID NO: 63. In some embodiments, the first polypeptide comprises an amino acid sequence that is at least 95% identical to SEQ ID NO: 63. In some embodiments, the first polypeptide comprises an amino acid sequence that is at least 96% identical to SEQ ID NO: 63. In some embodiments, the first polypeptide comprises an amino acid sequence that is at least 97% identical to SEQ ID NO: 63. In some embodiments, the first polypeptide comprises an amino acid sequence that is at least 98% identical to SEQ ID NO: 63. In some embodiments, the first polypeptide comprises an amino acid sequence that is at least 99% identical to SEQ ID NO: 63. In some embodiments, the first polypeptide comprises an amino acid sequence that is 100% identical to SEQ ID NO: 63.

In some embodiments, the first polypeptide comprises an amino acid sequence that is at least 92% identical to SEQ ID NO: 64. In some embodiments, the first polypeptide comprises an amino acid sequence that is at least 93% identical to SEQ ID NO: 64. In some embodiments, the first polypeptide comprises an amino acid sequence that is at least 94% identical to SEQ ID NO: 64. In some embodiments, the first polypeptide comprises an amino acid sequence that is at least 95% identical to SEQ ID NO: 64. In some embodiments, the first polypeptide comprises an amino acid sequence that is at least 96% identical to SEQ ID NO: 64. In some embodiments, the first polypeptide comprises an amino acid sequence that is at least 97% identical to SEQ ID NO: 64. In some embodiments, the first polypeptide comprises an amino acid sequence that is at least 98% identical to SEQ ID NO: 64. In some embodiments, the first polypeptide comprises an amino acid sequence that is at least 99% identical to SEQ ID NO: 64. In some embodiments, the first polypeptide comprises an amino acid sequence that is 100% identical to SEQ ID NO: 64.

In some embodiments, the first polypeptide comprises an amino acid sequence that is at least 92% identical to SEQ ID NO: 65. In some embodiments, the first polypeptide comprises an amino acid sequence that is at least 93% identical to SEQ ID NO: 65. In some embodiments, the first polypeptide comprises an amino acid sequence that is at least 94% identical to SEQ ID NO: 65. In some embodiments, the first polypeptide comprises an amino acid sequence that is at least 95% identical to SEQ ID NO: 65. In some embodiments, the first polypeptide comprises an amino acid sequence that is at least 96% identical to SEQ ID NO: 65. In some embodiments, the first polypeptide comprises an amino acid sequence that is at least 97% identical to SEQ ID NO: 65. In some embodiments, the first polypeptide comprises an amino acid sequence that is at least 98% identical to SEQ ID NO: 65. In some embodiments, the first polypeptide comprises an amino acid sequence that is at least 99% identical to SEQ ID NO: 65. In some embodiments, the first polypeptide comprises an amino acid sequence that is 100% identical to SEQ ID NO: 65.

In some embodiments, the second polypeptide comprises an amino acid sequence that is at least 92% identical to SEQ ID NO: 66. In some embodiments, the second polypeptide comprises an amino acid sequence that is at least 93% identical to SEQ ID NO: 66. In some embodiments, the second polypeptide comprises an amino acid sequence that is at least 94% identical to SEQ ID NO: 66. In some embodiments, the second polypeptide comprises an amino acid sequence that is at least 95% identical to SEQ ID NO: 66. In some embodiments, the second polypeptide comprises an amino acid sequence that is at least 96% identical to SEQ ID NO: 66. In some embodiments, the second polypeptide comprises an amino acid sequence that is at least 97% identical to SEQ ID NO: 66. In some embodiments, the second polypeptide comprises an amino acid sequence that is at least 98% identical to SEQ ID NO: 66. In some embodiments, the second polypeptide comprises an amino acid sequence that is at least 99% identical to SEQ ID NO: 66. In some embodiments, the second polypeptide comprises an amino acid sequence that is 100% identical to SEQ ID NO: 66.

In some embodiments, the second polypeptide comprises an amino acid sequence that is at least 92% identical to SEQ ID NO: 67. In some embodiments, the second polypeptide comprises an amino acid sequence that is at least 93% identical to SEQ ID NO: 67. In some embodiments, the second polypeptide comprises an amino acid sequence that is at least 94% identical to SEQ ID NO: 67. In some embodiments, the second polypeptide comprises an amino acid sequence that is at least 95% identical to SEQ ID NO: 67. In some embodiments, the second polypeptide comprises an amino acid sequence that is at least 96% identical to SEQ ID NO: 67. In some embodiments, the second polypeptide comprises an amino acid sequence that is at least 97% identical to SEQ ID NO: 67. In some embodiments, the second polypeptide comprises an amino acid sequence that is at least 98% identical to SEQ ID NO: 67. In some embodiments, the second polypeptide comprises an amino acid sequence that is at least 99% identical to SEQ ID NO: 67. In some embodiments, the second polypeptide comprises an amino acid sequence that is 100% identical to SEQ ID NO: 67.

In some embodiments, the second polypeptide comprises an amino acid sequence that is at least 92% identical to SEQ ID NO: 68. In some embodiments, the second polypeptide comprises an amino acid sequence that is at least 93% identical to SEQ ID NO: 68. In some embodiments, the second polypeptide comprises an amino acid sequence that is at least 94% identical to SEQ ID NO: 68. In some embodiments, the second polypeptide comprises an amino acid sequence that is at least 95% identical to SEQ ID NO: 68. In some embodiments, the second polypeptide comprises an amino acid sequence that is at least 96% identical to SEQ ID NO: 68. In some embodiments, the second polypeptide comprises an amino acid sequence that is at least 97% identical to SEQ ID NO: 68. In some embodiments, the second polypeptide comprises an amino acid sequence that is at least 98% identical to SEQ ID NO: 68. In some embodiments, the second polypeptide comprises an amino acid sequence that is at least 99% identical to SEQ ID NO: 68. In some embodiments, the second polypeptide comprises an amino acid sequence that is 100% identical to SEQ ID NO: 68.

In some embodiments, the second polypeptide comprises an amino acid sequence that is at least 92% identical to SEQ ID NO: 69. In some embodiments, the second polypeptide comprises an amino acid sequence that is at least 93% identical to SEQ ID NO: 69. In some embodiments, the second polypeptide comprises an amino acid sequence that is at least 94% identical to SEQ ID NO: 69. In some embodiments, the second polypeptide comprises an amino acid sequence that is at least 95% identical to SEQ ID NO: 69. In some embodiments, the second polypeptide comprises an amino acid sequence that is at least 96% identical to SEQ ID NO: 69. In some embodiments, the second polypeptide comprises an amino acid sequence that is at least 97% identical to SEQ ID NO: 69. In some embodiments, the second polypeptide comprises an amino acid sequence that is at least 98% identical to SEQ ID NO: 69. In some embodiments, the second polypeptide comprises an amino acid sequence that is at least 99% identical to SEQ ID NO: 69. In some embodiments, the second polypeptide comprises an amino acid sequence that is 100% identical to SEQ ID NO: 69.

In some embodiments, the second polypeptide comprises an amino acid sequence that is at least 92% identical to SEQ ID NO: 70. In some embodiments, the second polypeptide comprises an amino acid sequence that is at least 93% identical to SEQ ID NO: 70. In some embodiments, the second polypeptide comprises an amino acid sequence that is at least 94% identical to SEQ ID NO: 70. In some embodiments, the second polypeptide comprises an amino acid sequence that is at least 95% identical to SEQ ID NO: 70. In some embodiments, the second polypeptide comprises an amino acid sequence that is at least 96% identical to SEQ ID NO: 70. In some embodiments, the second polypeptide comprises an amino acid sequence that is at least 97% identical to SEQ ID NO: 70. In some embodiments, the second polypeptide comprises an amino acid sequence that is at least 98% identical to SEQ ID NO: 70. In some embodiments, the second polypeptide comprises an amino acid sequence that is at least 99% identical to SEQ ID NO: 70. In some embodiments, the second polypeptide comprises an amino acid sequence that is 100% identical to SEQ ID NO: 70.

In some embodiments, the second polypeptide comprises an amino acid sequence that is at least 92% identical to SEQ ID NO: 71. In some embodiments, the second polypeptide comprises an amino acid sequence that is at least 93% identical to SEQ ID NO: 71. In some embodiments, the second polypeptide comprises an amino acid sequence that is at least 94% identical to SEQ ID NO: 71. In some embodiments, the second polypeptide comprises an amino acid sequence that is at least 95% identical to SEQ ID NO: 71. In some embodiments, the second polypeptide comprises an amino acid sequence that is at least 96% identical to SEQ ID NO: 71. In some embodiments, the second polypeptide comprises an amino acid sequence that is at least 97% identical to SEQ ID NO: 71. In some embodiments, the second polypeptide comprises an amino acid sequence that is at least 98% identical to SEQ ID NO: 71. In some embodiments, the second polypeptide comprises an amino acid sequence that is at least 99% identical to SEQ ID NO: 71. In some embodiments, the second polypeptide comprises an amino acid sequence that is 100% identical to SEQ ID NO: 71.

In some embodiments, the second polypeptide comprises an amino acid sequence that is at least 92% identical to SEQ ID NO: 72. In some embodiments, the second polypeptide comprises an amino acid sequence that is at least 93% identical to SEQ ID NO: 72. In some embodiments, the second polypeptide comprises an amino acid sequence that is at least 94% identical to SEQ ID NO: 72. In some embodiments, the second polypeptide comprises an amino acid sequence that is at least 95% identical to SEQ ID NO: 72. In some embodiments, the second polypeptide comprises an amino acid sequence that is at least 96% identical to SEQ ID NO: 72. In some embodiments, the second polypeptide comprises an amino acid sequence that is at least 97% identical to SEQ ID NO: 72. In some embodiments, the second polypeptide comprises an amino acid sequence that is at least 98% identical to SEQ ID NO: 72. In some embodiments, the second polypeptide comprises an amino acid sequence that is at least 99% identical to SEQ ID NO: 72. In some embodiments, the second polypeptide comprises an amino acid sequence that is 100% identical to SEQ ID NO: 72.

In some embodiments, the second polypeptide comprises an amino acid sequence that is at least 92% identical to SEQ ID NO: 73. In some embodiments, the second polypeptide comprises an amino acid sequence that is at least 93% identical to SEQ ID NO: 73. In some embodiments, the second polypeptide comprises an amino acid sequence that is at least 94% identical to SEQ ID NO: 73. In some embodiments, the second polypeptide comprises an amino acid sequence that is at least 95% identical to SEQ ID NO: 73. In some embodiments, the second polypeptide comprises an amino acid sequence that is at least 96% identical to SEQ ID NO: 73. In some embodiments, the second polypeptide comprises an amino acid sequence that is at least 97% identical to SEQ ID NO: 73. In some embodiments, the second polypeptide comprises an amino acid sequence that is at least 98% identical to SEQ ID NO: 73. In some embodiments, the second polypeptide comprises an amino acid sequence that is at least 99% identical to SEQ ID NO: 73. In some embodiments, the second polypeptide comprises an amino acid sequence that is 100% identical to SEQ ID NO: 73.

In some embodiments, the second polypeptide comprises an amino acid sequence that is at least 92% identical to SEQ ID NO: 74. In some embodiments, the second polypeptide comprises an amino acid sequence that is at least 93% identical to SEQ ID NO: 74. In some embodiments, the second polypeptide comprises an amino acid sequence that is at least 94% identical to SEQ ID NO: 74. In some embodiments, the second polypeptide comprises an amino acid sequence that is at least 95% identical to SEQ ID NO: 74. In some embodiments, the second polypeptide comprises an amino acid sequence that is at least 96% identical to SEQ ID NO: 74. In some embodiments, the second polypeptide comprises an amino acid sequence that is at least 97% identical to SEQ ID NO: 74. In some embodiments, the second polypeptide comprises an amino acid sequence that is at least 98% identical to SEQ ID NO: 74. In some embodiments, the second polypeptide comprises an amino acid sequence that is at least 99% identical to SEQ ID NO: 74. In some embodiments, the second polypeptide comprises an amino acid sequence that is 100% identical to SEQ ID NO: 74.

In some embodiments, the third polypeptide comprises an amino acid sequence that is at least 92% identical to SEQ ID NO: 50. In some embodiments, the third polypeptide comprises an amino acid sequence that is at least 93% identical to SEQ ID NO: 50. In some embodiments, the third polypeptide comprises an amino acid sequence that is at least 94% identical to SEQ ID NO: 50. In some embodiments, the second polypeptide comprises an amino acid sequence that is at least 95% identical to SEQ ID NO: 50. In some embodiments, the third polypeptide comprises an amino acid sequence that is at least 96% identical to SEQ ID NO: 50. In some embodiments, the third polypeptide comprises an amino acid sequence that is at least 97% identical to SEQ ID NO: 50. In some embodiments, the third polypeptide comprises an amino acid sequence that is at least 98% identical to SEQ ID NO: 50. In some embodiments, the third polypeptide comprises an amino acid sequence that is at least 99% identical to SEQ ID NO: 50. In some embodiments, the third polypeptide comprises an amino acid sequence that is 100% identical to SEQ ID NO: 50.

In one aspect, the present invention provides, among other things, a masked cytokine comprising a first polypeptide comprising an amino acid sequence of SEQ ID NO: 64, a second polypeptide comprising an amino acid sequence of SEQ ID NO: 66, a third polypeptide comprising an amino acid sequence of SEQ ID NO: 50.

In one aspect, the present invention provides, among other things, a masked cytokine comprising a first polypeptide comprising an amino acid sequence of SEQ ID NO: 65, a second polypeptide comprising an amino acid sequence of SEQ ID NO: 66, a third polypeptide comprising an amino acid sequence of SEQ ID NO: 50.

In one aspect, the present invention provides, among other things, a masked cytokine comprising a first polypeptide comprising an amino acid sequence of SEQ ID NO: 63, a second polypeptide comprising an amino acid sequence of SEQ ID NO: 66, a third polypeptide comprising an amino acid sequence of SEQ ID NO: 50.

In one aspect, the present invention provides, among other things, a masked cytokine comprising a first polypeptide comprising an amino acid sequence of SEQ ID NO: 65, a second polypeptide comprising an amino acid sequence of SEQ ID NO: 68, a third polypeptide comprising an amino acid sequence of SEQ ID NO: 50.

In one aspect, the present invention provides, among other things, a masked cytokine comprising a first polypeptide comprising an amino acid sequence of SEQ ID NO: 65, a second polypeptide comprising an amino acid sequence of SEQ ID NO: 69, a third polypeptide comprising an amino acid sequence of SEQ ID NO: 50.

In one aspect, the present invention provides, among other things, a masked cytokine comprising a first polypeptide comprising an amino acid sequence of SEQ ID NO: 65, a second polypeptide comprising an amino acid sequence of SEQ ID NO: 70, a third polypeptide comprising an amino acid sequence of SEQ ID NO: 50.

In one aspect, the present invention provides, among other things, a masked cytokine comprising a first polypeptide comprising an amino acid sequence of SEQ ID NO: 65, a second polypeptide comprising an amino acid sequence of SEQ ID NO: 67, a third polypeptide comprising an amino acid sequence of SEQ ID NO: 50.

In one aspect, the present invention provides, among other things, a masked cytokine comprising a first polypeptide comprising an amino acid sequence of SEQ ID NO: 65, a second polypeptide comprising an amino acid sequence of SEQ ID NO: 71, a third polypeptide comprising an amino acid sequence of SEQ ID NO: 50.

In one aspect, the present invention provides, among other things, a masked cytokine comprising a first polypeptide comprising an amino acid sequence of SEQ ID NO: 63, a second polypeptide comprising an amino acid sequence of SEQ ID NO: 72, a third polypeptide comprising an amino acid sequence of SEQ ID NO: 50.

In one aspect, the present invention provides, among other things, a masked cytokine comprising a first polypeptide comprising an amino acid sequence of SEQ ID NO: 63, a second polypeptide comprising an amino acid sequence of SEQ ID NO: 73, a third polypeptide comprising an amino acid sequence of SEQ ID NO: 50.

In one aspect, the present invention provides, among other things, a masked cytokine comprising a first polypeptide comprising an amino acid sequence of SEQ ID NO: 63, a second polypeptide comprising an amino acid sequence of SEQ ID NO: 67, a third polypeptide comprising an amino acid sequence of SEQ ID NO: 50.

In one aspect, the present invention provides, among other things, a masked cytokine comprising a first polypeptide comprising an amino acid sequence of SEQ ID NO: 63, a second polypeptide comprising an amino acid sequence of SEQ ID NO: 74, a third polypeptide comprising an amino acid sequence of SEQ ID NO: 50.

In one aspect, the present invention provides, among other things, a nucleic acid encoding a masked cytokine described herein.

In one aspect, the present invention provides, among other things, a vector comprising a nucleic acid encoding a masked cytokine described herein.

In one aspect, the present invention provides, among other things, a host cell comprising a nucleic acid or a vector encoding a masked cytokine described herein.

In one aspect, the present invention provides among other things, a method of producing a masked cytokine described herein comprising culturing a host cell under a condition that produces the masked cytokine.

In one aspect, the present invention provides, among other things, a pharmaceutical composition comprising the masked cytokine described herein and a pharmaceutically accepted carrier.

In one aspect, the present invention provides, among other things, a kit comprising the masked cytokine described herein or a pharmaceutical composition.

In one aspect, the present invention provides, among other things, a method of treating or preventing a neoplastic disease in a subject, the method comprising administering to the subject an effective amount of the masked cytokine described herein.

In one aspect, the present invention provides, among other things, a method of treating or preventing an inflammatory or autoimmune disease in a subject, the method comprising administering to the subject an effective amount of the masked cytokine described herein.

BRIEF DESCRIPTION OF THE DRAWINGS

The drawings are for illustration purposes only, not for limitation.

DEFINITIONS

Figure 1:
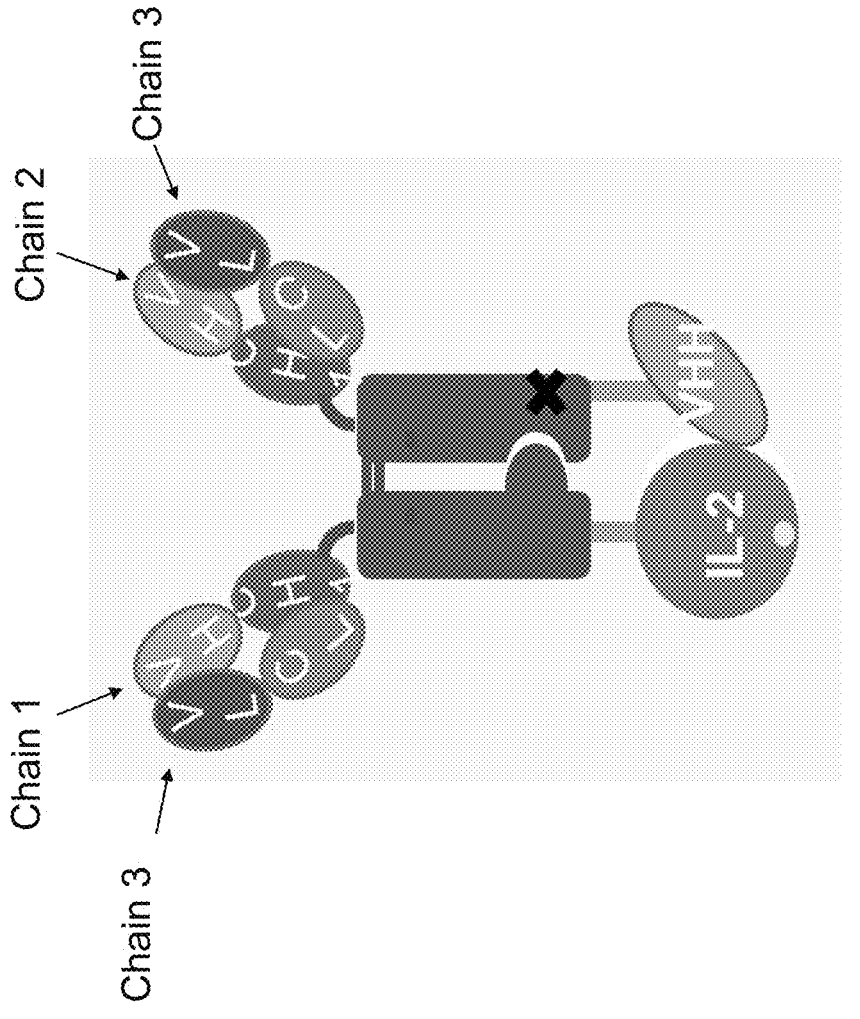
FIG. 1 is an exemplary schematic of a targeted cytokine construct containing a cleavable Fc domain. The cross indicates the location of a cleavage site. One Fc domain is fused to a cytokine via a non-cleavable linker, and the other Fc domain is fused to a masking moiety (e.g., anti-cytokine VHH) via a non-cleavable linker. Each Fc polypeptide also contains a targeting moiety (e.g., Fab) that can specifically bind to a target of interest (e.g., PD-1).

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

It is to be understood that this invention is not limited to particular compositions or biological systems, which can, of course, vary. It is also to be understood that the terminology used herein is for the purpose of describing particular embodiments only, and is not intended to be limiting.

As used in this specification and the appended claims, the singular forms "a," "an," and "the" include plural referents unless the content clearly dictates otherwise. Thus, for example, reference to "an IL-2 polypeptide" optionally includes a combination of two or more such polypeptides, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

As used herein, the term "and/or" refers to any one of the items, any combination of the items, or all of the items with which the term is associated. For instance, the phrase "A, B, and/or C" is intended to encompass each of the following embodiments: A, B, and C; A, B, or C; A or B; A or C; B or C; A and B; A and C; B and C; A and B or C; B and A or C; C and A or B; A (alone); B (alone); and C (alone).

The term "antibody" includes polyclonal antibodies, monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F (ab') 2, and Fv). The term "immunoglobulin" (Ig) is used interchangeably with "antibody" herein.

The term "diabodies" refers to small antibody fragments with two antigen-binding sites, which comprise a heavy chain variable (VH) domain connected to a light chain variable (VL) domain in the same polypeptide chain (VH-VL).

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the a and y chains and four CH domains for p and s isotypes. Each L chain has at the N-terminus, a variable domain (VL) followed by a constant domain at its other end. The VL is aligned with the VH, and the CL is aligned with the first constant domain of the heavy chain (CHI). Particular amino acid residues are believed to form an interface between the light chain and heavy chain variable domains. The pairing of a VH and VL together forms a single antigen-binding site.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated a, 8, e, y and p, respectively. The y and a classes are further divided into subclasses on the basis of relatively minor differences in the CH sequence and function, e.g., humans express the following subclasses: IgG1, IgG2, IgG3, IgG4, IgAQ1 and IgA2. IgG1 antibodies can exist in multiple polymorphic variants termed allotypes (reviewed in Jefferis and Lefranc 2009. mAbs Vol 1 Issue 4 1-7) any of which are suitable for use in the invention. Common allotypic variants in human populations are those designated by the letters a,f,n,z.

An "isolated" antibody is one that has been identified, separated and/or recovered from a component of its production environment (e.g., naturally or recombinantly). In some embodiments, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In some embodiments, the polypeptide is purified: (1) to greater than 95% by weight of antibody as determined by, for example, the Lowry method, and in some embodiments, to greater than 99% by weight; (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or silver stain. Isolated antibody includes the antibody in situ within recombinant cells since at least one component of the antibody's natural environment will not be present. Ordinarily, however, an isolated polypeptide or antibody is prepared by at least one purification step.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. In some embodiments, monoclonal antibodies have a C-terminal cleavage at the heavy chain and/or light chain. For example, 1, 2, 3, 4, or 5 amino acid residues are cleaved at the C-terminus of heavy chain and/or light chain. In some embodiments, the C-terminal cleavage removes a C-terminal lysine from the heavy chain. In some embodiments, monoclonal antibodies have an N-terminal cleavage at the heavy chain and/or light chain. For example, 1, 2, 3, 4, or 5 amino acid residues are cleaved at the N-terminus of heavy chain and/or light chain. In some embodiments truncated forms of monoclonal antibodies can be made by recombinant techniques. In some embodiments, monoclonal antibodies are highly specific, being directed against a single antigenic site. In some embodiments, monoclonal antibodies are highly specific, being directed against multiple antigenic sites (such as a bispecific antibody or a multispecific antibody). The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method, recombinant DNA methods, phage-display technologies, and technologies for producing human or human-like antibodies in animals that have parts or all of the human immunoglobulin loci or genes encoding human immunoglobulin sequences.

The terms "full-length antibody," "intact antibody" or "whole antibody" are used interchangeably to refer to an antibody in its substantially intact form, as opposed to an antibody fragment. Specifically, whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, such as the antigen binding region and/or the variable region of the intact antibody, and/or the constant region of the intact antibody. Examples of an antibody fragment include the Fc region of the antibody, a portion of the Fc region, or a portion of the antibody comprising the Fc region. Examples of antigen-binding antibody fragments include domain antibodies (dAbs), Fab, Fab', F(ab')2 and Fv fragments; diabodies; linear antibodies (see U.S. Pat. No. 5,641,870, Example 2; Zapata et ah, Protein Eng. 8 (10): 1057-1062 [1995]); single-chain antibody molecules, and multispecific antibodies formed from antibody fragments, a single chain Fv (scFv), a single domain antibody (VHH), one or more CDRs, a variable heavy chain (VH), a variable light chain (VL), a Fab-like bispecific antibodies (bsFab), a single-domain antibody-linked Fab (s-Fab), and a combination thereof. Single heavy chain antibodies or single light chain antibodies can be engineered, or in the case of the heavy chain, can be isolated from camelids, shark, libraries or mice engineered to produce single heavy chain molecules.

Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CHI). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having different antigen-binding activity and is still capable of cross-linking antigen. Fab' fragments differ from Fab fragments by having a few additional residues at the carboxy terminus of the CHI domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known. The Fc fragment comprises the carboxy-terminal portions of both H chains held together by disulfide bonds. The effector functions of antibodies are determined by sequences and glycan in the Fc region, the region which is also recognized by Fc receptors (FcR) found on certain types of cells.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For example, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Antibody "effector functions" refer to those biological activities attributable to the Fc region (a native sequence Fc region or amino acid sequence variant Fc region) of an antibody and vary with the antibody isotype. Examples of antibody effector functions include: Clq binding and complement dependent cytotoxicity; Fc receptor binding; antibody-dependent cell-mediated cytotoxicity (ADCC); phagocytosis; down regulation of cell surface receptors (e.g., B cell receptors); and B cell activation.

"Attenuated IL-2" is used herein to refer to an IL-2 variant that comprises one or more mutations that reduce but do not eliminate binding to IL-2Ra. Present inventors discovered that "attenuated IL-2" can effectively expand tumor-specific T cells better than "not-alpha IL-2" and exhibit less regulatory T cell activity than "alpha-biased IL-2" counterpart. In some embodiments, attenuated IL-2 comprises mutations of F42E and C125A.

"Not-alpha IL-2" is used herein to refer to an IL-2 variant that comprises one or more mutations that eliminate binding to IL-2Ra. In some embodiments, not-alpha IL-2 comprises mutations of R38A, F42A, Y45A, E62A, and C125A relative wild-type IL-2.

"Alpha-biased IL-2" is used herein to refer to an IL-2 variant that comprises one or more mutation that reduce or eliminate binding to IL-2Rβγ. Alpha-biased IL-2 has "biased" affinity to the cells that constitutively express IL-2a (e.g., regulatory T-cells).

"Binding affinity" as used herein refers to the strength of the non-covalent interactions between a single binding site of a molecule (e.g., a cytokine) and its binding partner (e.g., a cytokine receptor). In some embodiments, the affinity of a binding protein (e.g., a cytokine) can generally be represented by a dissociation constant (Kd). Affinity can be measured by common methods known in the art, including those described herein.

An "isolated" nucleic acid molecule encoding the cytokine polypeptides described herein is a nucleic acid molecule that is identified and separated from at least one contaminant nucleic acid molecule with which it is ordinarily associated in the environment in which it was produced. In some embodiments, the isolated nucleic acid is free of association with all components associated with the production environment. The isolated nucleic acid molecules encoding the polypeptides and cytokine polypeptides herein is in a form other than in the form or setting in which it is found in nature. Isolated nucleic acid molecules therefore are distinguished from nucleic acid encoding the polypeptides and cytokine polypeptides herein existing naturally in cells.

The term "pharmaceutical formulation" refers to a preparation that is in such form as to permit the biological activity of the active ingredient to be effective, and that contains no additional components that are unacceptably toxic to a subject to which the formulation would be administered.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™

As used herein, the term "treatment" refers to clinical intervention designed to alter the natural course of the individual or cell being treated during the course of clinical pathology. Desirable effects of treatment include decreasing the rate of disease progression, ameliorating, or palliating the disease state, and remission or improved prognosis. An individual is successfully "treated", for example, if one or more symptoms associated with a disorder (e.g., a neoplastic disease) are mitigated or eliminated. For example, an individual is successfully "treated" if treatment results in increasing the quality of life of those suffering from a disease, decreasing the dose of other medications required for treating the disease, reducing the frequency of recurrence of the disease, lessening severity of the disease, delaying the development or progression of the disease, and/or prolonging survival of individuals.

As used herein, "in conjunction with" or "in combination with" refers to administration of one treatment modality in addition to another treatment modality. As such, "in conjunction with" or "in combination with" refers to administration of one treatment modality before, during or after administration of the other treatment modality to the individual.

As used herein, the term "prevention" includes providing prophylaxis with respect to occurrence or recurrence of a disease in an individual. An individual may be predisposed to, susceptible to a disorder, or at risk of developing a disorder, but has not yet been diagnosed with the disorder. In some embodiments, targeted cytokines described herein are used to delay development of a disorder.

As used herein, an individual "at risk" of developing a disorder may or may not have detectable disease or symptoms of disease and may or may not have displayed detectable disease or symptoms of disease prior to the treatment methods described herein. "At risk" denotes that an individual has one or more risk factors, which are measurable parameters that correlate with development of the disease, as known in the art. An individual having one or more of these risk factors has a higher probability of developing the disorder than an individual without one or more of these risk factors.

An "effective amount" refers to at least an amount effective, at dosages and for periods of time necessary, to achieve the desired or indicated effect, including a therapeutic or prophylactic result.

An effective amount can be provided in one or more administrations. A "therapeutically effective amount" is at least the minimum concentration required to affect a measurable improvement of a particular disorder. A therapeutically effective amount herein may vary according to factors such as the disease state, age, sex, and weight of the patient, and the ability of the antibody to elicit a desired response in the individual. A therapeutically effective amount may also be one in which any toxic or detrimental effects of the targeted cytokine are outweighed by the therapeutically beneficial effects. A "prophylactically effective amount" refers to an amount effective, at the dosages and for periods of time necessary, to achieve the desired prophylactic result. Typically, but not necessarily, since a prophylactic dose is used in subjects prior to or at the earlier stage of disease, the prophylactically effective amount can be less than the therapeutically effective amount.

"Chronic" administration refers to administration of the medicament(s) in a continuous as opposed to acute mode, so as to main the initial therapeutic effect (activity) for an extended period of time. "Intermittent" administration is treatment that is not consecutively done without interruption, but rather is cyclic in nature.

As used herein, an "individual" or a "subject" is a mammal. A "mammal" for purposes of treatment includes humans, domestic and farm animals, and zoo, sports, or pet animals, such as dogs, horses, rabbits, cattle, pigs, hamsters, gerbils, mice, ferrets, rats, cats, etc. In some embodiments, the individual or subject is human Amino acid: As used herein, term "amino acid," in its broadest sense, refers to any compound and/or substance that can be incorporated into a polypeptide chain. In some embodiments, an amino acid has the general structure H2N—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an 1-amino acid. "Standard amino acid" refers to any of the twenty standard 1-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery).

Dosing interval: As used herein dosing interval in the context of a method for treating a disease is the frequency of administering a therapeutic composition in a subject (mammal) in need thereof, for example an mRNA composition, at an effective dose of the mRNA, such that one or more symptoms associated with the disease is reduced; or one or more biomarkers associated with the disease is reduced, at least for the period of the dosing interval. Dosing frequency and dosing interval may be used interchangeably in the current disclosure.

Expression: As used herein, "expression" of a nucleic acid sequence refers to translation of an mRNA into a polypeptide, assemble multiple polypeptides into an intact protein (e.g., enzyme) and/or post-translational modification of a polypeptide or fully assembled protein (e.g., enzyme). In this application, the terms "expression" and "production," and grammatical equivalent, are used inter-changeably.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in J. Pharmaceutical Sciences (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N+ (C1-4 alkyl) 4 salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

Subject: As used herein, the term "subject" refers to a human or any non-human animal (e.g., mouse, rat, rabbit, dog, cat, cattle, swine, sheep, horse, or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Various aspects of the invention are described in detail in the following sections. The use of sections is not meant to limit the invention. Each section can apply to any aspect of the invention. In this application, the use of "or" means "and/or" unless stated otherwise.

DETAILED DESCRIPTION

The masked cytokine constructs described herein are engineered to optimize binding between the masking moiety (e.g., anti-IL-2 VHH) and the cytokine (e.g., IL-2 polypeptide) to promote safe and effective targeted therapeutics for treating cancer. A VHH masking moiety binds to the IL-2 cytokine and inhibits a biological activity of the cytokine in undesired targets. Additionally, an Fc domain in the masked cytokine of the present invention is engineered to harbor a cleavage substrate. Upon cleavage in desired targets (e.g., tumor), the masking moiety is released from the cytokine, activating the function of the IL-2 polypeptide. In particular, the masked cytokine comprising an IL-2 and VHH masking moieties of the present invention is characterized with (1) effective masking efficiency such that IL-2 cytokine's function is inhibited in undesired targets; (2) efficient IL-2 activation by protease to release the VHH masking moiety; (3) selective IL-2 activation in tumor, and not in plasma; and (4) in vivo efficacy (e.g., high tumor growth inhibition).

Interleukin 2 (IL-2)

Provided herein are IL-2 polypeptide or functional fragment thereof for use in any masked cytokine or cleavage product thereof. IL-2 plays an important role in cellular signalling, particularly in cells of the immune system by regulating activities of white blood cells. Suitable IL-2 polypeptides for use in the present invention can be any IL-2 polypeptide or functional fragment thereof. In some embodiments, the IL-2 polypeptide is naturally occurring IL-2. In some embodiments, the IL-2 polypeptide comprises one or more substitutions (e.g., an IL-2 mutein, or IL-2 variant), or truncated IL-2. In some embodiments, the IL-2 is a polypeptide that retains at least one property of IL-2 biological activity. In present application, the terms IL-2 polypeptide and IL-2 cytokine are used interchangeably.

In eukaryotic cells, naturally occurring IL-2 polypeptide is synthesized as a precursor polypeptide of 153 amino acids. This is then processed into mature IL-2 by the removal of amino acid residues 1-20. This results in a mature form of IL-2 consisting of 133 amino acids (amino acid residues 21-153) in SEQ ID NO: 10. In some embodiments, the IL-2 polypeptide is naturally occurring IL-2.

```
                                         (SEQ ID NO: 10)
    APTSSSTKKTQLQLEHLLLDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFCQSIISTLT
```

In some embodiments, the mature IL-2 polypeptide comprises a mutation at position 125 relative to SEQ ID NO: 10. In some embodiments, the mutation comprises C125A resulting in SEQ ID NO: 11.

```
                                         (SEQ ID NO: 11)
    APTSSSTKKTQLQLEHLLLDLQMILNGINNYKNPKLTRMLTFKFY

MPKKATELKHLQCLEEELKPLEEVLNLAQSKNFHLRPRDLISNIN

VIVLELKGSETTFMCEYADETATIVEFLNRWITFAQSIISTLT
```

Attenuated IL-2

Present inventors discovered that the use of "attenuated IL-2 can effectively expand tumor-specific T cells better than other IL-2 variants (e.g., "not-alpha IL-2"), and exhibit less regulatory T cell activity than other IL-2 variants (e.g., "alpha-biased IL-2"). "Attenuated IL-2" refers to an IL-2 variant that comprises one or more mutations as compared to the wild-type IL-2 that reduce but do not eliminate binding to IL-2Ra. "Not-alpha IL-2" refers to an IL-2 variant that comprises one or more mutations that eliminate binding to IL-2Rα, and "alpha-biased IL-2" refers to an IL-2 variant that comprises one or more mutation that reduce or eliminate binding to IL-2Rβγ. In some embodiments, attenuated IL-2 comprises a mutation F42E. In some embodiments, attenuated IL-2 comprises mutations F42E and C125A.

In some embodiments, the amino acid substitutions reduce the affinity of the IL-2 polypeptide or functional fragment thereof for CD25 (IL-2Rα). In some embodiments, the IL-2 polypeptide or functional fragment thereof comprises mutations that reduce but do not eliminate affinity for IL-2Ra binding (e.g., attenuated IL-2).

In some embodiments, the IL-2 polypeptide or functional fragment thereof comprises an amino acid sequence having one or more amino acid substitutions as compared to the amino acid sequence of wild-type IL-2 of SEQ ID NO: 10 that reduces the affinity of the IL-2 polypeptide or functional fragment thereof for IL-2Ra (CD25).

In some embodiments, the IL-2 polypeptide or functional fragment thereof comprises amino acid sequence substitution F42E as compared to the amino acid sequence of SEQ ID NO: 10. In some embodiments, the IL-2 polypeptide or functional fragment thereof comprises amino acid sequence substitution F42E as compared to the amino acid sequence of SEQ ID NO: 11.

In some embodiments, the IL-2 polypeptide or functional fragment thereof comprises amino acid sequence substitutions F42E and C125A as compared to the amino acid sequence of SEQ ID NO: 10.

In some embodiments, the IL-2 polypeptide or functional fragment thereof comprises an amino acid sequence of SEQ ID NO: 13.

```
                                       (SEQ ID NO: 13)
APTSSSTKKTQLQLEHLLLDLQMILNGINNYKNPKLTRMLTEKFY

MPKKATELKHLQCLEEELKPLEEVLNLAQSKNFHLRPRDLISNIN

VIVLELKGSETTFMCEYADETATIVEFLNRWITFAQSIISTLT
```

In some embodiments, the IL-2 polypeptide or functional fragment thereof comprises an amino acid sequence having about or at least about 85%, 86%, 87%, 88%, 89%, 90%, 91%, 92%, 93%, 94%, 95%, 96%, 97%, 98%, or 99% sequence identity to the amino acid sequence of SEQ ID NO: 13. In some embodiments, the IL-2 polypeptide or functional fragment thereof comprises an amino acid sequence having at least about 80% identity to SEQ ID NO: 13. In some embodiments, the IL-2 polypeptide or functional fragment thereof comprises an amino acid sequence having at least about 85% identity to SEQ ID NO: 13. In some embodiments, the IL-2 polypeptide or functional fragment thereof comprises an amino acid sequence having at least about 90% identity to SEQ ID NO: 13. In some embodiments, the IL-2 polypeptide or functional fragment thereof comprises an amino acid sequence having at least about 92% identity to SEQ ID NO: 13. In some embodiments, the IL-2 polypeptide or functional fragment thereof comprises an amino acid sequence having at least about 95% identity to SEQ ID NO: 13. In some embodiments, the IL-2 polypeptide or functional fragment thereof comprises an amino acid sequence having at least about 96% identity to SEQ ID NO: 13. In some embodiments, the IL-2 polypeptide or functional fragment thereof comprises an amino acid sequence having at least about 97% identity to SEQ ID NO: 13. In some embodiments, the IL-2 polypeptide or functional fragment thereof comprises an amino acid sequence having at least about 98% identity to SEQ ID NO: 13. In some embodiments, the IL-2 polypeptide or functional fragment thereof comprises an amino acid sequence having at least about 99% identity to SEQ ID NO: 13. In some embodiments, the IL-2 polypeptide or functional fragment thereof comprises an amino acid sequence of SEQ ID NO: 13.

In some embodiments, the IL-2 polypeptide comprises a substitution at position 42 relative to SEQ ID NO: 10. In some embodiments, the substitution is F42A. In some embodiments, the substitution is F42E. In some embodiments, the substitution is F42K. In some embodiments, the substitution is F42S. In some embodiments, the substitution is F42R. In some embodiments, the substitution is F42Q. In some embodiments, the substitution is F42Y.

In some embodiments, the IL-2 polypeptide comprises a sequence selected from Table 1. In some embodiments, the IL-2 polypeptide comprises SEQ ID NO: 10. In some embodiment, the IL-2 polypeptide comprises SEQ ID NO: 11. In some embodiments, the IL-2 polypeptide comprises SEQ ID NO: 13.

"Functional fragments" of an IL-2 polypeptide comprise a portion of a full-length cytokine protein which retains or has modified cytokine receptor binding capability (e.g., within at least 50%, 80%, 90%, 95%, 96%, 97%, 98%, 99% or 100% activity compared to the full-length cytokine protein). Cytokine receptor binding capability can be shown, for example, by the capability of a cytokine to bind to the cytokine's cognate receptor or a component thereof (e.g., one or more chain(s) of a heterotrimeric receptor complex).

In some embodiments, the IL-2 polypeptide is a "not-alpha IL-2." Not-alpha IL-2" is used herein to refer to an IL-2 variant that comprises one or more mutations that eliminate binding to IL-2Rα. In some embodiments, not-alpha IL-2 comprises mutations of R38A, F42A, Y45A, E62A, and C125A relative wild-type IL-2. In some embodiments, the IL-2 polypeptide or functional fragment thereof comprises an amino acid sequence of SEQ ID NO: 12.

```
                                       (SEQ ID NO: 12)
APTSSSTKKTQLQLEHLLLDLQMILNGINNYKNPKLTAMLTAKFA

MPKKATELKHLQCLEEALKPLEEVLNLAQSKNFHLRPRDLISNIN

VIVLELKGSETTFMCEYADETATIVEFLNRWITFAQSIISTLT
```

In some embodiments, the IL-2 polypeptide or functional fragment thereof is any naturally occurring interleukin-2 (IL-2) protein or modified variant thereof capable of binding to an interleukin-2 receptor, particularly the IL-2Ra chain. In the context of IL-2 polypeptide binding, the target protein could be IL-2R (comprising the IL-2Rα, IL-2RB, and IL-2Ry chains), the IL-2Ra chain, the IL-2RB chain, or the IL-2Rα/β dimeric complex.

VHH Masking Moieties

The present invention provides, among other things, novel anti-IL-2 antigen binding fragments (e.g., VHH) that can be used as masking moieties in any of the masked or targeted IL-2 cytokines described herein. A VHH masking moiety binds to the IL-2 cytokine and inhibits a biological activity of the cytokine. Upon cleavage, the masking moiety is released from the cytokine, activating the function of the IL-2 polypeptide. In particular, VHH masking moieties of the present invention are characterized with improved binding kinetics, effective IL-2 masking efficiency (i.e., inhibiting IL-2 in non-target environment), and activating IL-2 activity once released from IL-2 to promote an anti-tumor-response in tumor-microenvironment. The VHH masking moieties of the present invention effectively mask or inhibit IL-2 activity such that the EC50 values based on pSTAT5 activity on CD8+ T cells of masked IL-2 cytokines are greater than 300-fold as compared to an IL-2 cytokine without a masking moiety. In some embodiments, a masked cytokine has an EC50 value based on pSTAT5 activity on CD8+ T cells of greater than 300-fold as compared to an IL-2 cytokine without a masking moiety. But once the masking moiety is cleaved from the IL-2 cytokine molecule, IL-2 function is restored. Preferentially, % of cleaved molecules in tumor is greater than 5% in at least one of the cancer indications tested, and % of cleaved molecules is below the lower limit of quantitation (LLOQ) in plasma.

In some embodiments, anti-IL-2 VHHs of the present invention have improved stability, developability and manufacturability to be produced in large-scale for use in therapeutics. In some embodiments, anti-IL-2 VHHs of the present invention have reduced immunogenicity (i.e., induce minimal endotoxin or have reduced binding to pre-existing anti-drug antibodies).

In some embodiments, an anti-IL-2 VHH binds to wild-type IL-2, attenuated IL-2, and not-alpha IL-2 with high affinity (e.g., ≤5 nM).

In some embodiments, the masking moiety is a heavy-chain-only antibody (VHH). In some embodiments, the masking moiety is an anti-IL-2 VHH antibody described herein.

VHH antibody (or nanobody) is the antigen binding fragment of heavy chain only antibodies. The VHH may be derived from, for example, an organism that produces VHH antibody such as a camelid, and a shark. In some cases, the VHH may be a recombinant VHH. VHH technology is based on fully functional antibodies from camelids that lack light chains. These heavy-chain antibodies contain a single variable domain (VHH) and two constant domains (CH2 and CH3). A VHH comprises a single chain polypeptide having three CDRs and four framework regions (FRs1-4). As used herein, "framework region" or "FR" refers to a region in the variable domain which is located between the CDRs. As used herein, "complementary determining region" or "CDR" refers to variable regions in VHHs that contains the amino acid sequences capable of specifically binding to antigenic targets (e.g., cytokines). In present application, VHH and sdAb are used interchangeably.

In some embodiments, the VHH comprises three CDRs and four framework regions, designated FR1, CDR1, FR2, CDR2, FR3, CDR3, and FR4. In some embodiments, a VHH may be truncated at the N-terminus or C-terminus such that it comprises only a partial FR1 and/or FR4, or lacks one or both of those framework regions, so long as the VHH substantially maintains cytokine binding and specificity.

In some embodiments, the VHH masking moiety is linked to the Fc domain. In some embodiments, the VHH masking moiety is linked to a cleavable Fc domain by a non-cleavable linker. In some embodiments, the VHH masking moiety is linked to a non-cleavable Fc domain by a non-cleavable linker.

In some embodiments, the VHH antibody binds to an IL-2 polypeptide. In some embodiments, the VHH antibody binds to a wild-type IL-2. In some embodiments, the VHH antibody binds to a variant of IL-2. In some embodiments, the VHH antibody binds to an engineered variant of IL-2. In some embodiments, the VHH antibody binds to an attenuated IL-2. In some embodiments, the VHH antibody binds to a not-alpha IL-2.

In some embodiments, the VHH masking moieties of the present invention are further modified. Some modifications provide modified molecules with a reduced ability to bind to pre-existing anti-drug antibodies (ADAs) as compared to the unmodified molecule. In other words, the modified molecule will bind with reduced affinity or avidity to a pre-existing ADA. Modifications can be selected from, for example and without limitation, C-terminal additions, extensions, deletions, or tags. Additional modifications are described in WO2013024059A2, the contents of which are incorporated herein by reference.

Additionally, the modified molecules may have an enhanced safety profile and fewer side effects than the unmodified molecule which does not comprise a C-terminal extension, addition, deletion, or tag. Administration of pharmaceutical compositions comprising the modified molecules can lead to improved immunogenicity and increased efficacy. A composition comprising the modified molecules can be advantageously used for repeated dosing to subjects who could develop autoantibodies to the unmodified molecules.

In some embodiments, the targeted masked cytokine comprises a modification. In some embodiments, the targeted masked cytokine comprises a C-terminal extension. In some embodiments, the targeted masked cytokine comprises a C-terminal addition. In some embodiments, the targeted masked cytokine comprises a C-terminal deletion. In some embodiments, the targeted masked cytokine comprises a C-terminal tag.

In some embodiments, the masking moiety comprises a modification. In some embodiments, the masking moiety comprises a C-terminal extension. In some embodiments, the masking moiety comprises a C-terminal addition. In some embodiments, the masking moiety comprises a C-terminal deletion. In some embodiments, the masking moiety comprises a C-terminal tag.

In some embodiments, the VHH antibody comprises a modification. In some embodiments, the VHH antibody comprises a C-terminal extension. In some embodiments, the VHH antibody comprises a C-terminal addition. In some embodiments, the VHH antibody comprises a C-terminal deletion. In some embodiments, the VHH antibody comprises a C-terminal tag.

In some embodiments, the C-terminal extension comprises an alanine. In some embodiments, the C-terminal extension comprises the sequence AS (SEQ ID NO: 34). In some embodiments, the C-terminal extension comprises the sequence AST (SEQ ID NO: 35). In some embodiments, the C-terminal extension comprises the sequence AAA (SEQ ID NO: 18). In some embodiments, the C-terminal extension comprises the sequence AH (SEQ ID NO: 36). In some embodiments, the C-terminal extension comprises the sequence GS (SEQ ID NO: 37). In some embodiments, the C-terminal extension comprises the sequence PP (SEQ ID NO: 38). In some embodiments, the C-terminal extension comprises the sequence PPP (SEQ ID NO: 39). In some embodiments, the C-terminal extension comprises the sequence GP (SEQ ID NO: 40). In some embodiments, the C-terminal modification comprises a deletion and an extension comprising the sequence GP (SEQ ID NO: 40).

In some embodiments, the VHH antibody comprises an amino acid sequence of SEQ ID NO: 19. In some embodiments, the VHH antibody comprises an amino acid sequence of SEQ ID NO: 20. In some embodiments, the VHH antibody comprises an amino acid sequence of SEQ ID NO: 21. In some embodiments, the VHH antibody comprises an amino acid sequence of SEQ ID NO: 22.

TABLE A

| Exemplary VHH Masking Moieties (CDRs underlined) | |
| --- | --- |
| SEQ ID | Sequence |
| VHH1 | EVQLVESGGGLVQPGGSLRLSCAAS GSIFSINVMGWYRQAPGKQRELVAA ISSGGSTNYADSVKGRFTISRDNAK NTVYLQMNSLKPEDTAVYYCMYASS WYEDETDYWGQGTQVTVSS (SEQ ID NO: 19) |
| VHH2 | EVQLVESGGGLVQPGGSLRLSCAAS GSIFSINVMGWYRQAPGKGRELVAA ISSGGSTNYADSVKGRFTISRDNAK NTVYLQMNSLKPEDTAVYYCAYASS FYEDETDYWGQGTQVTVSS (SEQ ID NO: 20) |
| VHH3 | EVQLVESGGGLVQPGGSLRLSCAAS GSIFSINVMGWYRQAPGKQRELVAA ISSGGSTNYADSVKGRFTISRDNAK NTVYLQMNSLKPEDTAVYYCMYASS WYEDETDYWGQGTQVTVSSAAA (SEQ ID NO: 21) |

TABLE A-continued

Exemplary VHH Masking Moieties
(CDRs underlined)

| SEQ ID | Sequence |
|---|---|
| VHH4 | EVQLVESGGGLVQPGGSLRLSCAAS<br>GSIFSINVMGWYRQAPGKGRELVAA<br>ISSGGSTNYADSVKGRFTISRDNAK<br>NTVYLQMNSLKPEDTAVYYCAYASS<br>FYEDETDYWGQGTQVTVSSAAA<br>(SEQ ID NO: 22) |

In some embodiments, the VHH antibody comprises an amino acid sequence at least 85% identical to SEQ ID NO: 19. In some embodiments, the VHH antibody comprises an amino acid sequence at least 87% identical to SEQ ID NO: 19. In some embodiments, the VHH antibody comprises an amino acid sequence at least 90% identical to SEQ ID NO: 19. In some embodiments, the VHH antibody comprises an amino acid sequence at least 92% identical to SEQ ID NO: 19. In some embodiments, the VHH antibody comprises an amino acid sequence at least 93% identical to SEQ ID NO: 19. In some embodiments, the VHH antibody comprises an amino acid sequence at least 94% identical to SEQ ID NO: 19. In some embodiments, the VHH antibody comprises an amino acid sequence at least 95% identical to SEQ ID NO: 19. In some embodiments, the VHH antibody comprises an amino acid sequence at least 96% identical to SEQ ID NO: 19. In some embodiments, the VHH antibody comprises an amino acid sequence at least 97% identical to SEQ ID NO: 19. In some embodiments, the VHH antibody comprises an amino acid sequence at least 98% identical to SEQ ID NO: 19. In some embodiments, the VHH antibody comprises an amino acid sequence at least 99% identical to SEQ ID NO: 19. In some embodiments, the VHH antibody comprises an amino acid sequence that is identical to SEQ ID NO: 19.

In some embodiments, the VHH antibody comprises an amino acid sequence at least 85% identical to SEQ ID NO: 20. In some embodiments, the VHH antibody comprises an amino acid sequence at least 87% identical to SEQ ID NO: 20. In some embodiments, the VHH antibody comprises an amino acid sequence at least 90% identical to SEQ ID NO: 20. In some embodiments, the VHH antibody comprises an amino acid sequence at least 92% identical to SEQ ID NO: 20. In some embodiments, the VHH antibody comprises an amino acid sequence at least 93% identical to SEQ ID NO: 20. In some embodiments, the VHH antibody comprises an amino acid sequence at least 94% identical to SEQ ID NO: 20. In some embodiments, the VHH antibody comprises an amino acid sequence at least 95% identical to SEQ ID NO: 20. In some embodiments, the VHH antibody comprises an amino acid sequence at least 96% identical to SEQ ID NO: 20. In some embodiments, the VHH antibody comprises an amino acid sequence at least 97% identical to SEQ ID NO: 20. In some embodiments, the VHH antibody comprises an amino acid sequence at least 98% identical to SEQ ID NO: 20. In some embodiments, the VHH antibody comprises an amino acid sequence at least 99% identical to SEQ ID NO: 20. In some embodiments, the VHH antibody comprises an amino acid sequence that is identical to SEQ ID NO: 20.

In some embodiments, the VHH antibody comprises an amino acid sequence at least 85% identical to SEQ ID NO: 21. In some embodiments, the VHH antibody comprises an amino acid sequence at least 87% identical to SEQ ID NO: 21. In some embodiments, the VHH antibody comprises an amino acid sequence at least 90% identical to SEQ ID NO:

21. In some embodiments, the VHH antibody comprises an amino acid sequence at least 92% identical to SEQ ID NO: 21. In some embodiments, the VHH antibody comprises an amino acid sequence at least 93% identical to SEQ ID NO: 21. In some embodiments, the VHH antibody comprises an amino acid sequence at least 94% identical to SEQ ID NO: 21. In some embodiments, the VHH antibody comprises an amino acid sequence at least 95% identical to SEQ ID NO: 21. In some embodiments, the VHH antibody comprises an amino acid sequence at least 96% identical to SEQ ID NO: 21. In some embodiments, the VHH antibody comprises an amino acid sequence at least 97% identical to SEQ ID NO: 21. In some embodiments, the VHH antibody comprises an amino acid sequence at least 98% identical to SEQ ID NO: 21. In some embodiments, the VHH antibody comprises an amino acid sequence at least 99% identical to SEQ ID NO: 21. In some embodiments, the VHH antibody comprises an amino acid sequence that is identical to SEQ ID NO: 21.

In some embodiments, the VHH antibody comprises an amino acid sequence at least 85% identical to SEQ ID NO: 22. In some embodiments, the VHH antibody comprises an amino acid sequence at least 87% identical to SEQ ID NO: 22. In some embodiments, the VHH antibody comprises an amino acid sequence at least 90% identical to SEQ ID NO: 22. In some embodiments, the VHH antibody comprises an amino acid sequence at least 92% identical to SEQ ID NO: 22. In some embodiments, the VHH antibody comprises an amino acid sequence at least 93% identical to SEQ ID NO: 22. In some embodiments, the VHH antibody comprises an amino acid sequence at least 94% identical to SEQ ID NO: 22. In some embodiments, the VHH antibody comprises an amino acid sequence at least 95% identical to SEQ ID NO: 22. In some embodiments, the VHH antibody comprises an amino acid sequence at least 96% identical to SEQ ID NO: 22. In some embodiments, the VHH antibody comprises an amino acid sequence at least 97% identical to SEQ ID NO: 22. In some embodiments, the VHH antibody comprises an amino acid sequence at least 98% identical to SEQ ID NO: 22. In some embodiments, the VHH antibody comprises an amino acid sequence at least 99% identical to SEQ ID NO: 22. In some embodiments, the VHH antibody comprises an amino acid sequence that is identical to SEQ ID NO: 22.

TABLE B

CDRs of Exemplary VHH Masking Moieties

| SEQ ID | CDR1 | CDR2 | CDR3 |
|---|---|---|---|
| VHH1 | GSIFSI NVMG (SEQ ID NO: 14) | AISSGG STNYAD SVKG (SEQ ID NO: 15) | ASSWYE DETDY (SEQ ID NO: 16) |
| VHH2 | GSIFSI NVMG (SEQ ID NO: 14) | AISSGG STNYAD SVKG (SEQ ID NO: 15) | ASSFYE DETDY (SEQ ID NO: 17) |
| VHH3 | GSIFSI NVMG (SEQ ID NO: 14) | AISSGG STNYAD SVKG (SEQ ID NO: 15) | ASSWYE DETDY (SEQ ID NO: 16) |

TABLE B-continued

CDRs of Exemplary VHH Masking Moieties

| SEQ ID | CDR1 | CDR2 | CDR3 |
|---|---|---|---|
| VHH4 | GSIFSI NVMG (SEQ ID NO: 14) | AISSGG STNYAD SVKG (SEQ ID NO: 15) | ASSFYE DETDY (SEQ ID NO: 17) |

In some embodiments, the VHH antibody comprises a CDR1 of GSIFSINVMG (SEQ ID NO: 14), a CDR2 of AISSGGSTNYADSVKG (SEQ ID NO: 15), and a CDR3 of ASSWYEDETDY (SEQ ID NO: 16).

In some embodiments, the VHH antibody comprises a CDR1 of GSIFSINVMG (SEQ ID NO: 14), a CDR2 of AISSGGSTNYADSVKG (SEQ ID NO: 15), and a CDR3 of ASSFYEDETDY (SEQ ID NO: 17).

In some embodiments, the VHH antibody comprises a CDR1 having an amino acid sequence that differs by 1 amino acid from SEQ ID NO: 14. In some embodiments, the VHH antibody comprises a CDR1 having an amino acid sequence that differs by 2 amino acids from SEQ ID NO: 14. In some embodiments, the VHH antibody comprises a CDR1 having an amino acid sequence that differs by 3 amino acids from SEQ ID NO: 14. In some embodiments, the VHH antibody comprises a CDR1 having an amino acid sequence that differs by 4 amino acids from SEQ ID NO: 14. In some embodiments, the VHH antibody comprises a CDR1 having an amino acid sequence that differs by 5 amino acids from SEQ ID NO: 14. In some embodiments, the VHH antibody comprises a CDR1 having an amino acid sequence that differs by 6 amino acids from SEQ ID NO: 14. In some embodiments, the VHH antibody comprises a CDR1 having an amino acid sequence that differs by 7 amino acids from SEQ ID NO: 14. In some embodiments, the VHH antibody comprises a CDR1 having an amino acid sequence that differs by 8 amino acids from SEQ ID NO: 14.

In some embodiments, the VHH antibody comprises a CDR2 having an amino acid sequence that differs by 1 amino acid from SEQ ID NO: 15. In some embodiments, the VHH antibody comprises a CDR2 having an amino acid sequence that differs by 2 amino acids from SEQ ID NO: 15. In some embodiments, the VHH antibody comprises a CDR2 having an amino acid sequence that differs by 3 amino acids from SEQ ID NO: 15. In some embodiments, the VHH antibody comprises a CDR2 having an amino acid sequence that differs by 4 amino acids from SEQ ID NO: 15. In some embodiments, the VHH antibody comprises a CDR2 having an amino acid sequence that differs by 5 amino acids from SEQ ID NO: 15. In some embodiments, the VHH antibody comprises a CDR2 having an amino acid sequence that differs by 6 amino acids from SEQ ID NO: 15. In some embodiments, the VHH antibody comprises a CDR2 having an amino acid sequence that differs by 7 amino acids from SEQ ID NO: 15. In some embodiments, the VHH antibody comprises a CDR2 having an amino acid sequence that differs by 8 amino acids from SEQ ID NO: 15. In some embodiments, the VHH antibody comprises a CDR2 having an amino acid sequence that differs by 9 amino acids from SEQ ID NO: 15. In some embodiments, the VHH antibody comprises a CDR2 having an amino acid sequence that differs by 10 amino acids from SEQ ID NO: 15.

In some embodiments, the VHH antibody comprises a CDR3 having an amino acid sequence that differs by 1 amino acid from SEQ ID NO: 16. In some embodiments, the VHH antibody comprises a CDR3 having an amino acid sequence that differs by 8 amino acids from SEQ ID NO: 16. In some embodiments, the VHH antibody comprises a CDR3 having an amino acid sequence that differs by 3 amino acids from SEQ ID NO: 16. In some embodiments, the VHH antibody comprises a CDR3 having an amino acid sequence that differs by 4 amino acids from SEQ ID NO: 16. In some embodiments, the VHH antibody comprises a CDR3 having an amino acid sequence that differs by 5 amino acids from SEQ ID NO: 16. In some embodiments, the VHH antibody comprises a CDR3 having an amino acid sequence that differs by 6 amino acids from SEQ ID NO: 16. In some embodiments, the VHH antibody comprises a CDR3 having an amino acid sequence that differs by 7 amino acids from SEQ ID NO: 16. In some embodiments, the VHH antibody comprises a CDR3 having an amino acid sequence that differs by 8 amino acids from SEQ ID NO: 16. In some embodiments, the VHH antibody comprises a CDR3 having an amino acid sequence that differs by 9 amino acids from SEQ ID NO: 16. In some embodiments, the VHH antibody comprises a CDR3 having an amino acid sequence that differs by 10 amino acids from SEQ ID NO: 16.

In some embodiments, the VHH antibody comprises a CDR3 having an amino acid sequence that differs by 1 amino acid from SEQ ID NO: 17. In some embodiments, the VHH antibody comprises a CDR3 having an amino acid sequence that differs by 8 amino acids from SEQ ID NO: 17. In some embodiments, the VHH antibody comprises a CDR3 having an amino acid sequence that differs by 3 amino acids from SEQ ID NO: 17. In some embodiments, the VHH antibody comprises a CDR3 having an amino acid sequence that differs by 4 amino acids from SEQ ID NO: 17. In some embodiments, the VHH antibody comprises a CDR3 having an amino acid sequence that differs by 5 amino acids from SEQ ID NO: 17. In some embodiments, the VHH antibody comprises a CDR3 having an amino acid sequence that differs by 6 amino acids from SEQ ID NO: 17. In some embodiments, the VHH antibody comprises a CDR3 having an amino acid sequence that differs by 7 amino acids from SEQ ID NO: 17. In some embodiments, the VHH antibody comprises a CDR3 having an amino acid sequence that differs by 8 amino acids from SEQ ID NO: 17. In some embodiments, the VHH antibody comprises a CDR3 having an amino acid sequence that differs by 9 amino acids from SEQ ID NO: 17. In some embodiments, the VHH antibody comprises a CDR3 having an amino acid sequence that differs by 10 amino acids from SEQ ID NO: 17.

Cleavable Fc Domain Carrier Moiety

A long half-life in vivo is important for therapeutic proteins. Unfortunately, cytokines that are administered to a subject generally have a short half-life since they are normally cleared rapidly from the subject by mechanisms including clearance by the kidney and endocytic degradation. Thus, in the masked cytokine provided herein, a carrier moiety is linked to the cytokine or a masking moiety for the purpose of extending the half-life of the cytokine in vivo, among other things.

As used herein, the term "cleavable carrier" refers to any agent that is cleavable from the present composition enzymatically or non-enzymatically. In the context of the present disclosure, the terms "cleavable carrier" and "cleavable domain" are used interchangeably. The present cleavable carrier moiety provides enzymatically induced prodrug activation, characterized in that the cleavage of the carrier moiety controls release of active therapeutics. The carrier moiety may be an Fc domain in which at least one tumor-associated protease cleavage site is engineered, e.g., by amino acid substitutions at particular positions of the Fc domain.

In some embodiments, the carrier moiety is an Fc domain.

In accordance with the present disclosure, the carrier moiety is an Fc domain derived from an immunoglobulin, such as IgM, IgG1, IgG2, IgG3, IgG4, IgD, IgE and IgA, or variant thereof, or fragment thereof. Accordingly, the Fc domain is genetically engineered to be enzymatically cleavable. The engineered Fc domain is referred to a "cleavable Fc domain".

In some embodiments, the Fc domain comprises a first Fc polypeptide and a second Fc polypeptide. In some embodiments, the Fc domain is from any antibody or fragment thereof comprising either a heavy chain Fc polypeptide or a light chain Fc polypeptide. In some embodiments, the Fc domain comprises a portion of either a heavy chain polypeptide or a light chain polypeptide. In some embodiments, the antibody or fragment thereof comprises an Fc domain or fragment thereof. In some embodiments, the Fc domain derived from an antibody or fragment thereof comprises a hinge region, a CH2 domain and a CH3 domain or a fragment thereof. In some embodiments, the Fc domain comprises only the constant domain of the heavy chain polypeptide. In some embodiments, the Fc domain comprises only the constant domain of the light chain polypeptide. In some embodiments, the Fc domain comprises a first Fc polypeptide having the CH2 and CH3 domains and a second Fc polypeptide having the CH2 and CH3 domains. In some embodiments, the Fc domain comprises a first Fc polypeptide having the CH3 domain and a second Fc polypeptide having the CH3 domain. In some embodiments, the Fc domain comprises a first Fc polypeptide having the CH2 and CH3 domains and a second Fc polypeptide having the CH3 domain. In some embodiments, the Fc domain comprises a first Fc polypeptide having the CH3 domain and a second Fc polypeptide having the CH2 and CH3 domains.

In some embodiments, the first Fc polypeptide and the second Fc polypeptide are linked via a linker such as a short peptide linker. In some embodiments, the linker is non-cleavable.

In some embodiments, the Fc polypeptide comprises an amino acid sequence of SEQ ID NO: 28.

```
                                        (SEQ ID NO: 28)
  DKTHTCPPCPAPELLGGPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPSR

DELTKNQVSLTCLVKGFYPSDIAVEWESNGQPENNYKTTPPVLDS

DGSFFLYSKLTVDKSRWQQGNVFSCSVMHEALHNHYTQKSLSLSP

GK.
```

In some embodiments, the Fc domain comprises an amino acid sequence at least 85% identical to SEQ ID NO: 28. In some embodiments, the Fc domain comprises an amino acid sequence at least 88% identical to SEQ ID NO: 28. In some embodiments, the Fc domain comprises an amino acid sequence at least 90% identical to SEQ ID NO: 28. In some embodiments, the Fc domain comprises an amino acid sequence at least 92% identical to SEQ ID NO: 28. In some embodiments, the Fc domain comprises an amino acid sequence at least 94% identical to SEQ ID NO: 28. In some embodiments, the Fc domain comprises an amino acid sequence at least 96% identical to SEQ ID NO: 28. In some embodiments, the Fc domain comprises an amino acid sequence at least 97% identical to SEQ ID NO: 28. In some embodiments, the Fc domain comprises an amino acid sequence at least 98% identical to SEQ ID NO: 28. In some embodiments, the Fc domain comprises an amino acid sequence at least 99% identical to SEQ ID NO: 28.

Incorporation of Cleavable Substrate

An engineered cleavable Fc domain comprises one or more cleavable sites.

In some embodiments, an Fc domain comprises a first Fc polypeptide comprising a cleavage site, and a second Fc polypeptide that does not comprise a cleavage site. In some embodiments, an Fc domain comprises a first Fc polypeptide that does not comprise a cleavage site, and a second Fc polypeptide comprising a cleavage site. In some embodiments, an Fc domain comprises a first Fc polypeptide and a second Fc polypeptide wherein the first Fc polypeptide and the second Fc polypeptide each comprises a cleavage site.

As used herein, a "cleavage site" refers to a recognizable site for cleavage of a portion of the cleavable peptide found in any of the Fc domain. A "cleavage site" can be an amino acid sequence, such as a short peptide motif, that is recognized and cleaved by a cleaving agent. The cleavage sites may be the amino acid sequences naturally in the Fc domain. Additionally, and/or alternatively, the cleavage sites may be introduced into the cleavable portion of the Fc domain by mutations (e.g., amino acid insertions, substitutions and deletions). The mutations do not change other activities of Fc domain. In some embodiments, one or more cleavage peptide motifs may be engineered in the cleavable Fc domain as described herein. The cleaving agent may be an enzyme, for example a protease. In some embodiments, the cleavage sites are protease cleavage sites such that the cleavable Fc domain is proteolytically cleavable. Proteases are enzymes that cleave and hydrolyse the peptide bonds between two specific amino acid residues of target substrate proteins. Proteases general recognize a specific peptide motif and cleave the peptide bonds between two specific amino acid residues within the short peptide motif.

The Fc domain may be engineered to include one or more peptide motifs that can be recognized by one or more protease such as tumor associated proteases, tissue selective proteases and diseases (e.g., inflammation) associated proteases. As non-limiting examples, the cleavable Fc domain as described herein may be cleaved by a disease associated or tissue selective protease selected from matrix metalloproteases (MMP1, MMP2, MMP3, MMP7, MMP8, MMP9, MMP10, MMP11, MMP12, MMP13, MMP14, MMP15, MMP16, MMP17, MMP19, MMP20, MMP21, MMP23A, MMP23B, MMP24, MMP25, MMP27 and MMP28), Cathepsins (Cathepsin B, cathepsin D, cathepsin F, cathepsin K, cathepsin L, cathepsin V, cathepsin S and cathepsin W), ADAM, ADAMTS, Kallikreins 1 to 15, HTRA1-2-3, HGFAc, PRSS, TMPRSS, elastase, PR-3, granzymes (granzyme A, B, M, H and K), fibroblast activation proteins (FAP), plasmin, urokinase plasminogen activator (uPA), Tryptase, Caspase, Thrombin, Legumain, Chymase, Collagenase, napsin A, and matriptase1-2.

In some embodiments, the cleavable Fc domain as described herein comprises at least one engineered tumor-associated protease cleavage site. A "tumor-associated protease cleavage site" as provided herein is an amino acid sequence recognized by a protease whose expression is specific or upregulated for a tumor cell or tumor cell environment thereof. In some embodiments, the tumor-associated protease is a matrix metalloproteinase (MMP), selected from the group consisting of MMP1, MMP2, MMP3, MMP7, MMP8, MMP9, MMP10, MMP11, MMP12, MMP13, MMP14, MMP15, MMP16, MMP17, MMP19, MMP20, MMP21, MMP23A, MMP23B, MMP24, MMP25, MMP27, and MMP28. In one embodiment, the tumor-associated protease is MMP2. In another embodiment, the tumor-associated protease is MMP3. In yet another embodiment, the tumor-associated protease is MMP9. In yet another embodiment, the tumor-associated protease is MMP10. In some embodiments, the protease is Cathepsin B. In other embodiments, the protease is matriptase.

An advantage of such engineered cleavable Fc domain provides a universal design architecture; such that the fusion of an engineered cleavable Fc domain to a therapeutic agent and the subsequent cleavage at the cleavage site allows release of the agent at a particular environment, e.g., a tumor microenvironment.

The tumor cell environment is complex and can comprise multiple different proteases. As such, the precise site at which the Fc domain will be cleaved in the tumor cell environment may vary between tumor types, between patients with the same tumor type and even between cleavage products formed in the same tumor dependent on the specific tumor cell environment. Moreover, even after cleavage, further modification of the initial cleavage product, e.g., by removal of one or two terminal amino acids, may occur by the further action of proteases in the tumor cell environment. A distribution of cleavage products is expected to form in the tumor cell environment of a patient following administration of a single structure of a targeted cytokine as described herein.

It will be understood that a cleavage site as referred to herein refers to a site between two specific amino acid residues within the cleavable peptide that are a target for a protease known to be associated with a tumor cell environment. In this sense, there may be more than one cleavage site present in a cleavable peptide as described herein where different proteases cleave the cleavable peptide at different cleavage sites. It is also possible that more than one protease may act on the same cleavage site within a cleavable peptide. Discussion of protease cleavage sites can be found in the art.

Thus, the cleavable Fc domain disclosed herein may be cleaved by one or more proteases. In some embodiments, the cleavage sites of the cleavable Fc domain are cleavage sites of one or more tumor associated proteases. In some embodiments, the cleavage sites of the cleavable Fc domain are cleavage sites of one or more tissue selective proteases. In some embodiments, the cleavage sites of the cleavable Fc domain are cleavage sites of one or more inflammation associated proteases. In other embodiments, the cleavable Fc domain comprises one or more cleavage sites of other disease-associated proteases.

In some embodiments, the cleavable Fc domain is a substrate for a protease that is co-localized in a region or a tissue or an organ expressing the cytokine receptor.

In some embodiments, the cleavable peptide motif in the Fc domain is from 3 to 18 amino acids in length. In some embodiments, the cleavable peptide motif in the Fc domain is from 5 to 10 amino acids in length, or from 5 to 8 amino acids in length, or from 6 to 10 amino acids in length, or from 7 to 10 amino acids in length, or from 6 to 12 amino acids in length. In some embodiments, the cleavable peptide motif in the Fc domain is 3 amino acids in length. In some embodiments, the cleavable peptide motif in the Fc domain is 4 amino acids in length. In some embodiments, the cleavable peptide motif in the Fc domain is 5 amino acids in length. In some embodiments, the cleavable peptide motif in the Fc domain is 6 amino acids in length. In some embodiments, the cleavable peptide motif in the Fc domain is 7 amino acids in length. In some embodiments, the cleavable peptide motif in the Fc domain is 8 amino acids in length. In some embodiments, the cleavable peptide motif in the Fc domain is 9 amino acids in length. In some embodiments, the cleavable peptide motif in the Fc domain is 10 amino acids in length.

In some embodiments, the protease cleavage site within the engineered cleavable Fc domain is in the hinge region, in the CH2 domain, in the CH3 domain and/or in the CH2-CH3 domain linker region. In some embodiments, the protease cleavage site within the engineered cleavable Fc domain is in the F strand region. In some embodiments, the protease cleavage site within the engineered cleavable Fc domain is in the FG-loop region. In some embodiments, the protease cleavage site within the engineered cleavable Fc domain is in the G-strand region.

In some embodiments, the cleavable sites within the engineered cleavable Fc domain may be created based on the short amino acid motifs close to a cleavage site of a protease.

In some embodiments, the cleavable peptide motif within the engineered cleavable Fc domain comprises PLGL (SEQ ID NO: 1). In some embodiments, the cleavable peptide motif within the engineered cleavable Fc domain comprises SLPLGL (SEQ ID NO: 2). In some embodiments, the cleavable peptide motif within the engineered cleavable Fc domain comprises GGPLGL (SEQ ID NO: 3). In some embodiments, the cleavable peptide motif within the engineered cleavable Fc domain comprises MPYDLYHP (SEQ ID NO: 5). In some embodiments, the cleavable peptide motif within the engineered cleavable Fc domain comprises APAGLIVPYN (SEQ ID NO: 7). In some embodiments, the cleavable peptide motif within the engineered cleavable Fc domain comprises PANLVAPDP (SEQ ID NO: 9).

In some embodiments, an engineered cleavable Fc domain comprises one or more substitutions in the CH3 domain. In some embodiments, an engineered cleavable Fc domain comprises one or more substitutions in the C-terminal region within the Fc domain. In some embodiments, an engineered cleavable Fc domain comprises one or more substitutions in the G-strand within the Fc domain. In some embodiments, an engineered cleavable Fc domain comprises one or more substitutions in positions between 436-447 by EU numbering. In some embodiments, an engineered cleavable Fc domain comprises one or more substitutions in positions between 438 and 447 by EU numbering.

In some embodiments, the cleavable peptide motif is located between positions 438 and 445 by EU numbering. In some embodiments, the cleavable peptide motif is located between positions 439 and 446 by EU numbering. In some embodiments, the cleavable peptide motif is located between positions 440 and 447 by EU numbering. In some embodiments, the cleavable peptide motif is located between positions 438 and 447 by EU numbering. In some embodiments, the cleavable peptide motif is located between positions 437 and 444 by EU numbering. In some embodiments, the cleavable peptide motif is located between positions 440 and 443 by EU numbering. In some embodiments, the cleavable peptide motif is located between positions 441 and 444 by EU numbering. In some embodiments, the cleavable peptide motif is located between positions 442 and 445 by EU numbering. In some embodiments, the cleavable peptide motif is located between positions 444 and 447 by EU numbering. In some embodiments, the cleavable peptide motif is located between positions 441 and 447 by EU numbering. In some embodiments, the cleavable peptide motif is located between positions 443 and 447 by EU numbering. In some embodiments, the cleavable peptide motif is located between positions 436 and 443 by EU numbering. In some embodiments, the cleavable peptide motif is located between positions 442 and 447 by EU numbering.

In some embodiments, an engineered cleavable Fc domain comprises one or more substitutions shown in Table C.

TABLE C

Exemplary Engineered Fc domain comprising cleavable substrates

| Cleavage Substrate | Fc Mutations | Cleavage Substrate location |
|---|---|---|
| SL-PLGL | S444P, P445L, G447L | 444-PLGL-447 |
| GG-PLGL | S442G, L443G, S444P, P445L, G447L | 442-GGPLGL-447 |
| MPY | S440M, L441P, S442Y, L443D, S444L, P445Y, G446H, G447P, | 440-MPYDLYHP-447 |
| APAG | Q438A, K439P, S440A, L441G, S442L, L443I, S444V, G446Y, G447N | 438-APAGLIVPYN-447 |
| PAN | Q438P, K439A, S440N, S442V, L443A, S444P, P445D, G446P | 438-PANLVAPDP-446 |

In some embodiments, an engineered cleavable Fc domain comprises S444P, P445L, and G447L substitutions by EU numbering. In some embodiments, an engineered cleavable Fc domain comprises S442G, L443G, S444P, P445L, and G447L substitutions by EU numbering. In some embodiments, an engineered cleavable Fc domain comprises S440M, L441P, S442Y, L443D, S444L, P445Y, G446H, and G447P substitutions by EU numbering. In some embodiments, an engineered cleavable Fc domain comprises Q438A, K439P, S440A, L441G, S442L, L443I, S444V, G446Y, and G447N substitutions by EU numbering. In some embodiments, an engineered cleavable Fc domain comprises Q438P, K439A, S440N, S442V, L443A, S444P, P445D, and G446P substitutions by EU numbering.

In some embodiments, an engineered cleavable Fc domain comprises a first Fc polypeptide and a second Fc polypeptide, wherein the first Fc polypeptide comprises S444P, P445L, and G447L substitutions by EU numbering. In some embodiments, an engineered cleavable Fc domain comprises a first Fc polypeptide and a second Fc polypeptide, wherein the first Fc polypeptide comprises S442G, L443G, S444P, P445L, and G447L substitutions by EU numbering. In some embodiments, an engineered cleavable Fc domain comprises a first Fc polypeptide and a second Fc polypeptide, wherein the first Fc polypeptide comprises S440M, L441P, S442Y, L443D, S444L, P445Y, G446H, and G447P substitutions by EU numbering. In some embodiments, an engineered cleavable Fc domain comprises a first Fc polypeptide and a second Fc polypeptide, wherein the first Fc polypeptide comprises Q438A, K439P, S440A, L441G, S442L, L443I, S444V, G446Y, and G447N substitutions by EU numbering. In some embodiments, an engineered cleavable Fc domain comprises a first Fc polypeptide and a second Fc polypeptide, wherein the first Fc polypeptide comprises Q438P, K439A, S440N, S442V, L443A, S444P, P445D, and G446P substitutions by EU numbering.

In some embodiments, an engineered cleavable Fc domain comprises a first Fc polypeptide and a second Fc polypeptide, wherein the second Fc polypeptide comprises S444P, P445L, and G447L substitutions by EU numbering. In some embodiments, an engineered cleavable Fc domain comprises a first Fc polypeptide and a second Fc polypeptide, wherein the second Fc polypeptide comprises S442G, L443G, S444P, P445L, and G447L substitutions by EU numbering. In some embodiments, an engineered cleavable Fc domain comprises a first Fc polypeptide and a second Fc polypeptide, wherein the second Fc polypeptide comprises S440M, L441P, S442Y, L443D, S444L, P445Y, G446H, and G447P substitutions by EU numbering. In some embodiments, an engineered cleavable Fc domain comprises a first Fc polypeptide and a second Fc polypeptide, wherein the second Fc polypeptide comprises Q438A, K439P, S440A, L441G, S442L, L443I, S444V, G446Y, and G447N substitutions by EU numbering. In some embodiments, an engineered cleavable Fc domain comprises a first Fc polypeptide and a second Fc polypeptide, wherein the second Fc polypeptide comprises Q438P, K439A, S440N, S442V, L443A, S444P, P445D, and G446P substitutions by EU numbering.

In some embodiments, the engineered cleavable Fc domain is used as a carrier moiety of a cytokine for cancer treatment. The engineered cleavable Fc domain is fused to a masked cytokine molecule such that upon cleavage of the engineered protease cleavage site such as the engineered tumor-associated protease cleavage site in the cleavable Fc domain, the masked cytokine is released from the masking moiety.

In some embodiments, the cleavable Fc domain, in addition to incorporation of one or more protease cleavage sites, may comprise further mutations described herein.

Fc Engineering to Promote Heterodimerization or to Increase Half-Life

An Fc domain or a fragment thereof that is capable of FcRn-mediated recycling, can be reduce or otherwise delay clearance of the targeted cytokine from a subject, thereby prolonging the half-life of the administered targeted cytokine. In some embodiments, the cleavable Fc domain or a fragment thereof is any antibody or fragment thereof that is capable of FcRn-mediated recycling, such as any heavy chain polypeptide or portion thereof (e.g., Fc domain or fragment thereof) that is capable of FcRn-mediated recycling.

The cleavable Fc domain or a fragment thereof may be derived from any antibody or fragment thereof. However, in some embodiments, either a first Fc polypeptide or a second Fc polypeptide may does not bind to the FcRn receptor, such as a light chain polypeptide. For example, in some embodiments, a first Fc polypeptide does not directly interact with the FcRn receptor, but the targeted cytokine nonetheless has an extended half-life due to comprising a second Fc polypeptide that is capable of interacting with the FcRn receptor, such as by comprising a heavy chain polypeptide. It is recognized in the art that FcRn-mediated recycling requires binding of the FcRn receptor to the Fc region of the antibody or fragment thereof. For instance, studies have shown that residues I253, S254, H435, and Y436 (numbering according to the Kabat EU index numbering system) are important for the interaction between the human Fc region and the human FcRn complex. See, e.g., Firan, M., et al., Int. Immunol. 13 (2001) 993-1002; Shields, R. L., et al, J. Biol. Chem. 276 (2001) 6591-6604). Various mutants of residues 248-259, 301-317, 376-382, and 424-437 (numbering according to the Kabat EU index numbering system) have also been examined and reported. Yeung, Y. A., et al. (J. Immunol. 182 (2009) 7667-7671.

In some embodiments, the first and/or second Fc polypeptides of the cleavable Fc domains each contain one or more modifications that promote the non-covalent association of the first and the second Fc polypeptides. In some embodiments, the first Fc polypeptide comprises an IgG1 Fc domain or fragment thereof including the mutations Y349C; T366S; L368A; and Y407V to form a 'hole' in the first half-life extension domain and the second Fc polypeptide comprises an IgG1 Fc domain or fragment thereof including the mutations S354C and T366W to form the 'knob' in the second half-life extension domain.

In some embodiments, the first and second Fc polypeptides are each an IgG1, IgG2 or IgG4 Fc domain or fragment thereof. In some embodiments, the first and second Fc polypeptides are each an IgG1 Fc domain or fragment thereof.

In some embodiments, the first and second Fc polypeptides comprise SEQ ID NO: 28 with amino substitutions to promote association of the first and second Fc polypeptides according to the 'knob into holes' approach.

In some embodiments, the sequence of SEQ ID NO: 28 contains mutations S354C and T366W (numbered according to the Kabat EU numbering system) to form the 'knob' in the first Fc polypeptide and mutations Y349C; T366S; L368A; and Y407V (numbered according to the Kabat EU numbering system) to form the 'hole' in the second Fc polypeptide.

In some embodiments, the sequence of SEQ ID NO: 28 contains mutations Y349C; T366S; L368A; and Y407V (numbered according to the Kabat EU numbering system) to form the 'hole' in the first Fc polypeptide and mutations S354C and T366W (numbered according to the Kabat EU numbering system) to form the 'knob' in the second Fc polypeptide. These modified sequences have SEQ ID NOs: 29 and 30 shown below:

Fc polypeptide with hole (Y349C; T366S; L368A; and Y407V):

```
                                        (SEQ ID NO: 29)
DKTHTCPPCPAPELLGGPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVCTLPPSR

DELTKNQVSLSCAVKGFYPSDIAVEWESNGQPENNYKTTPPVLDS

DGSFFLVSKLTVDKSRWQQGNVFSCSVMHEALHNHYTQKSLSLSP

G
```

Fc polypeptide with knob (S354C and T366W):

```
                                        (SEQ ID NO: 30)
DKTHTCPPCPAPELLGGPSVFLFPPKPKDTLMISRTPEVTCVVVD

VSHEDPEVKFNWYVDGVEVHNAKTKPREEQYNSTYRVVSVLTVLH

QDWLNGKEYKCKVSNKALPAPIEKTISKAKGQPREPQVYTLPPCR

DELTKNQVSLWCLVKGFYPSDIAVEWESNGQPENNYKTTPPVLDS

DGSFFLYSKLTVDKSRWQQGNVFSCSVMHEALHNHYTQKSLSLSP

G
```

In some embodiments, the first and second Fc polypeptides each further comprise amino substitution N297A, numbered according to the Kabat EU numbering system:

Fc polypeptide with hole (Y349C; T366S; L368A; Y407V and N297A):

```
                                        (SEQ ID NO: 31)
DKTHTCPPCPAPELLGGPSVFLFPPKPKDTLMISRTPEVTCVVVD

VSHEDPEVKFNWYVDGVEVHNAKTKPREEQYASTYRVVSVLTVLH

QDWLNGKEYKCKVSNKALPAPIEKTISKAKGQPREPQVCTLPPSR

DELTKNQVSLSCAVKGFYPSDIAVEWESNGQPENNYKTTPPVLDS

DGSFFLVSKLTVDKSRWQQGNVFSCSVMHEALHNHYTQKSLSLSP

G
```

Fc polypeptide with knob (S354C, T366W and N297A):

```
                                        (SEQ ID NO: 32)
DKTHTCPPCPAPELLGGPSVFLFPPKPKDTLMISRTPEVTCVVVD

VSHEDPEVKFNWYVDGVEVHNAKTKPREEQYASTYRVVSVLTVLH

QDWLNGKEYKCKVSNKALPAPIEKTISKAKGQPREPQVYTLPPCR

DELTKNQVSLWCLVKGFYPSDIAVEWESNGQPENNYKTTPPVLDS

DGSFFLYSKLTVDKSRWQQGNVFSCSVMHEALHNHYTQKSLSLSP

G
```

In some embodiments, the first Fc polypeptide comprises an amino acid sequence having about or at least about 85%, 86%, 87%, 88%, 89%, 90%, 91%, 92%, 93%, 94%, 95%, 96%, 97%, 98%, or 99% sequence identity to the amino acid sequence of SEQ ID NO: 29.

In some embodiments, the first Fc polypeptide comprises an amino acid sequence having about or at least about 85%, 86%, 87%, 88%, 89%, 90%, 91%, 92%, 93%, 94%, 95%, 96%, 97%, 98%, or 99% sequence identity to the amino acid sequence of SEQ ID NO: 30.

In some embodiments, the first Fc polypeptide comprises an amino acid sequence having about or at least about 85%, 86%, 87%, 88%, 89%, 90%, 91%, 92%, 93%, 94%, 95%, 96%, 97%, 98%, or 99% sequence identity to the amino acid sequence of SEQ ID NO: 31.

In some embodiments, the first Fc polypeptide comprises an amino acid sequence having about or at least about 85%, 86%, 87%, 88%, 89%, 90%, 91%, 92%, 93%, 94%, 95%, 96%, 97%, 98%, or 99% sequence identity to the amino acid sequence of SEQ ID NO: 32.

In some embodiments, the second Fc polypeptide comprises an amino acid sequence having about or at least about 85%, 86%, 87%, 88%, 89%, 90%, 91%, 92%, 93%, 94%, 95%, 96%, 97%, 98%, or 99% sequence identity to the amino acid sequence of SEQ ID NO: 29.

In some embodiments, the second Fc polypeptide comprises an amino acid sequence having about or at least about 85%, 86%, 87%, 88%, 89%, 90%, 91%, 92%, 93%, 94%, 95%, 96%, 97%, 98%, or 99% sequence identity to the amino acid sequence of SEQ ID NO: 30.

In some embodiments, the second Fc polypeptide comprises an amino acid sequence having about or at least about 85%, 86%, 87%, 88%, 89%, 90%, 91%, 92%, 93%, 94%, 95%, 96%, 97%, 98%, or 99% sequence identity to the amino acid sequence of SEQ ID NO: 31.

In some embodiments, the second Fc polypeptide comprises an amino acid sequence having about or at least about 85%, 86%, 87%, 88%, 89%, 90%, 91%, 92%, 93%, 94%, 95%, 96%, 97%, 98%, or 99% sequence identity to the amino acid sequence of SEQ ID NO: 32.

In some embodiments, the first Fc polypeptide comprises an amino acid sequence having one or more modifications, such as one or more amino acid substitutions, additions, or deletions, as compared to the amino acid sequence of any one of SEQ ID NOs: 29-32. In some embodiments, the second Fc polypeptide comprises an amino acid sequence having one or more modifications, such as one or more amino acid substitutions, additions, or deletions, as compared to the amino acid sequence of any one of SEQ ID NOs: 29-32. The one or more modifications can be any modifications or alterations described herein, including, in some embodiments, any modifications or alterations disclosed herein that promote heterodimerization of polypeptide chains and/or suppresses homodimerization of polypeptide chains, alter effector function, or enhance effector function.

In some embodiments, the protease cleavage sites as described herein may be introduced into any of SEQ ID NOs: 29-32.

In some embodiments, the cleavable Fc domain may further comprise one or more amino acid substitutions altering effector function. In some embodiments, the half-life extension domain is an IgG1 Fc domain or fragment thereof and comprises one or more amino acid substitutions selected from the group consisting of N297A, N297G, N297Q, L234A, L235A, C220S, C226S, C229S, P238S, E233P, L234V, L234F, L235E, P331S, S267E, L328F, D265A, and P329G, numbered according to the Kabat EU numbering system. In some embodiments, the half-life extension domain is an IgG2 Fc domain or fragment thereof and comprises the amino substitution(s): V234A and G237A; H268Q, V309L, A330S, and A331S; and/or V234A, G237A, P238S, H268A, V309L, and A330S, numbered according to the Kabat EU numbering system. In some embodiments, the half-life extension domain is an IgG2 Fc domain or fragment thereof and comprises one or more amino acid substitutions selected from the group consisting of V234A, G237A, H268Q, V309L, A330S, A331S, P238S, H268A, and V309L, numbered according to the Kabat EU numbering system. In some embodiments, the half-life extension domain is an IgG4 Fc domain or fragment thereof and comprises the amino substitution(s): L235A, G237A, and E318A; S228P, L234A, and L235A; H268Q, V309L, A330S, and P331S; and/or S228P and L235A, numbered according to the Kabat EU numbering system. In some embodiments, the half-life extension domain is an IgG2 Fc domain or fragment thereof and comprises one or more amino acid substitutions selected from the group consisting of L235A, G237A, E318A, S228P, L234A, H268Q, V309L, A330S, and P331S, numbered according to the Kabat EU numbering system.

In some embodiments, the cleavable Fc domain further comprises one or more amino acid substitutions enhancing effector function. In some embodiments, the half-life extension domain is an IgG1 Fc domain or fragment thereof and comprises the amino acid substitution(s): S298A, E333A, and K334A; S239D and I332E; S239D, A330L, and I332E; P247I and A339D or A339Q; D280H and K290S; D280H, K290S, and either S298D or S298V; F243L, R292P, and Y300L; F243L, R292P, Y300L, and P396L; F243L, R292P, Y300L, V305I, and P396L; G236A, S239D, and I332E; K326A and E333A; K326W and E333S; K290E, S298G, and T299A; K290E, S298G, T299A, and K326E; K290N, S298G, and T299A; K290N, S298G, T299A, and K326E; K334V; L235S, S239D, and K334V; K334V and Q331M, S239D, F243V, E294L, or S298T; E233L, Q311M, and K334V; L234I, Q311M, and K334V; K334V and S298T, A330M, or A330F; K334V, Q311M, and either A330M or A330F; K334V, S298T, and either A330M or A330F; K334V, S239D, and either A330M or S298T; L234Y, Y296W, and K290Y, F243V, or E294L; Y296W and either L234Y or K290Y; S239D, A330S, and I332E, V264I; F243L and V264I; L328M; I332E; L328M and I332E; V264I and I332E; S239E and I332E; S239Q and I332E; S239E; A330Y; I332D; L328I and I332E; L328Q and I332E; V264T; V240I; V266I; S239D; S239D and I332D; S239D and I332N; S239D and I332Q; S239E and I332D; S239E and I332N; S239E and I332Q; S239N and I332D; S239N and I332E; S239Q and I332D; A330Y and I332E; V264I, A330Y, and I332E; A330L and I332E; V264I, A330L, and I332E; L234E, L234Y, or L234I; L235D, L235S, L235Y, or L235I; S239T; V240M; V264Y; A330I; N325T; I332E and L328D, L328V, L328T, or L328I; V264I, I332E, and either S239E or S239Q; S239E, V264I, A330Y, and I332E; A330Y, I332E, and either S239D or S239N; A330L, I332E, and either S239D or S239N; V264I, S298A, and I332E; S298A, I332E, and either S239D or S239N; S239D, V264I, and I332E; S239D, V264I, S298A, and I332E; S239D, V264I, A330L, and I332E; S239D, I332E, and A330I; P230A; P230A, E233D, and I332E; E272Y; K274T, K274E, K274R, K274L, or K274Y; F275W; N276L; Y278T; V302I; E318R; S324D, S324I or S324V; K326I or K326T; T335D, T335R, or T335Y; V240I and V266I; S239D, A330Y, I332E, and L234I; S239D, A330Y, I332E, and L235D; S239D, A330Y, I332E, and V240I; S239D, A330Y, I332E, and V264T; and/or S239D, A330Y, I332E, and either K326E or K326T, numbered according to the Kabat EU numbering system. In some embodiments, the cleavable Fc domain is an IgG1 Fc domain or fragment thereof and comprises one or more amino acid substitution(s) selected from the group consisting of: P230A, E233D, L234E, L234Y, L234I, L235D, L235S, L235Y, L235I, S239D, S239E, S239N, S239Q, S239T, V240I, V240M, F243L, V264I, V264T, V264Y, V266I, E272Y, K274T, K274E, K274R, K274L, K274Y, F275W, N276L, Y278T, V302I, E318R, S324D, S324I, S324V, N325T, K326I, K326T, L328M, L328I, L328Q, L328D, L328V, L328T, A330Y, A330L, A330I, I332D, I332E, I332N, I332Q, T335D, T335R, and T335Y.

In some embodiments, the cleavable Fc domain further comprises one or more amino acid substitution(s) that enhance binding of the half-life extension domain to FcRn. In some embodiments, the one or more amino acid substitution(s) increase binding affinity of an Fc-containing polypeptide (e.g., a heavy chain polypeptide or an Fc domain or fragment thereof to FcRn at acidic pH. In some embodiments, the half-life extension domain comprises one or more amino acid substitution(s) selected from the group consisting of M428F; T250Q and M428F; M252Y, S254T, and T256E; P257I and N434H; D376V and N434H; P257I and Q311I; N434A; N434W; M428F and N434S; V259I and V308F; M252Y, S254T, and T256E; V259I, V308F, and M428F; T307Q and N434A; T307Q and N434S; T307Q, E380A, and N434A; V308P and N434A; N434H; and V308P.

RF Mutation or CH3 Domain Swap for Heterodimeric Protein Purification

Two immunoglobulin heavy chains that differ by at least one amino acid allows isolation of the antigen-binding protein based on a differential affinity of an immunoglobulin heavy chain and a modified or mutated immunoglobulin heavy chain toward an affinity reagent. The antigen-binding proteins that have IgG CH2 and CH3 regions with different affinities with respect to Protein A allow rapid isolation by differential binding of the IgG regions to Protein A.

In one embodiment, a first Fc polypeptide comprises a 95R modification (by IMGT exon numbering; 435R by EU numbering) in the CH3 region. In another embodiment, an isolation Fc polypeptide further comprises a 96F modification (IMGT; 436F by EU). In some embodiments, a second Fc polypeptide comprises wild-type CH2 and CH3 domains derived from IgG1 or IgG4, and a second Fc polypeptide comprises 95R/96F modifications by IMGT exon numbering. In some embodiments, a second Fc polypeptide comprises wild-type CH2 and CH3 domains derived from IgG1 or IgG4, and a first Fc polypeptide comprises 435R/436F modifications by EU numbering.

In some embodiments, a second Fc polypeptide comprises wild-type CH2 and CH3 domains derived from IgG1 or IgG4, and a first Fc polypeptide comprises CH3 domain derived from IgG3.

In some embodiments, a first Fc polypeptide or a second Fc polypeptide comprises amino acid sequence of SEQ ID NO: 33. SEQ ID NO: 33 comprises "knob mutations" with "RF mutations" (435R/436F).

```
                                         (SEQ ID NO: 33)
DKTHTCPPCPAPELLGGPSVFLFPPKPKDTLMISRTPEVTCVVVD

VSHEDPEVKENWYVDGVEVHNAKTKPREEQYASTYRVVSVLTVLH

QDWLNGKEYKCKVSNKALPAPIEKTISKAKGQPREPQVYTLPPCR

DELTKNQVSLWCLVKGFYPSDIAVEWESNGQPENNYKTTPPVLDS

DGSFFLYSKLTVDKSRWQQGNVFSCSVMHEALHNRFTQKSLSLSP

G
```

In some embodiments, a first Fc polypeptide or a second Fc polypeptide comprises amino acid sequence having at least about 85% identity to SEQ ID NO: 33. In some embodiments, a first Fc polypeptide or a second Fc polypeptide comprises amino acid sequence having at least about 90% identity to SEQ ID NO: 33. In some embodiments, a first Fc polypeptide or a second Fc polypeptide comprises amino acid sequence having at least about 91% identity to SEQ ID NO: 33. In some embodiments, a first Fc polypeptide or a second Fc polypeptide comprises amino acid sequence having at least about 92% identity to SEQ ID NO: 33. In some embodiments, a first Fc polypeptide or a second Fc polypeptide comprises amino acid sequence having at least about 93% identity to SEQ ID NO: 33. In some embodiments, a first Fc polypeptide or a second Fc polypeptide comprises amino acid sequence having at least about 94% identity to SEQ ID NO: 33. In some embodiments, a first Fc polypeptide or a second Fc polypeptide comprises amino acid sequence having at least about 95% identity to SEQ ID NO: 33. In some embodiments, a first Fc polypeptide or a second Fc polypeptide comprises amino acid sequence having at least about 96% identity to SEQ ID NO: 33. In some embodiments, a first Fc polypeptide or a second Fc polypeptide comprises amino acid sequence having at least about 97% identity to SEQ ID NO: 33. In some embodiments, a first Fc polypeptide or a second Fc polypeptide comprises amino acid sequence having at least about 98% identity to SEQ ID NO: 33. In some embodiments, a first Fc polypeptide or a second Fc polypeptide comprises amino acid sequence having at least about 99% identity to SEQ ID NO: 33.

In some embodiments, a first Fc polypeptide or a second Fc polypeptide comprises amino acid sequence of SEQ ID NO: 23. SEQ ID NO: 23 comprises "hole mutations" with cleavage substrate of SLPLGL (SEQ ID NO: 2).

```
                                         (SEQ ID NO: 23)
DKTHTCPPCPAPELLGGPSVFLFPPKPKDTLMISRTPEVTCVVVD

VSHEDPEVKFNWYVDGVEVHNAKTKPREEQYASTYRVVSVLTVLH

QDWLNGKEYKCKVSNKALPAPIEKTISKAKGQPREPQVCTLPPSR

DELTKNQVSLSCAVKGFYPSDIAVEWESNGQPENNYKTTPPVLDS

DGSFFLVSKLTVDKSRWQQGNVFSCSVMHEALHNHYTQKSLSLPL

GL
```

In some embodiments, a first Fc polypeptide or a second Fc polypeptide comprises amino acid sequence having at least about 85% identity to SEQ ID NO: 23. In some embodiments, a first Fc polypeptide or a second Fc polypeptide comprises amino acid sequence having at least about 90% identity to SEQ ID NO: 23. In some embodiments, a first Fc polypeptide or a second Fc polypeptide comprises amino acid sequence having at least about 91% identity to SEQ ID NO: 23. In some embodiments, a first Fc polypeptide or a second Fc polypeptide comprises amino acid sequence having at least about 92% identity to SEQ ID NO: 23. In some embodiments, a first Fc polypeptide or a second Fc polypeptide comprises amino acid sequence having at least about 93% identity to SEQ ID NO: 23. In some embodiments, a first Fc polypeptide or a second Fc polypeptide comprises amino acid sequence having at least about 94% identity to SEQ ID NO: 23. In some embodiments, a first Fc polypeptide or a second Fc polypeptide comprises amino acid sequence having at least about 95% identity to SEQ ID NO: 23. In some embodiments, a first Fc polypeptide or a second Fc polypeptide comprises amino acid sequence having at least about 96% identity to SEQ ID NO: 23. In some embodiments, a first Fc polypeptide or a second Fc polypeptide comprises amino acid sequence having at least about 97% identity to SEQ ID NO: 23. In some embodiments, a first Fc polypeptide or a second Fc polypeptide comprises amino acid sequence having at least about 98% identity to SEQ ID NO: 23. In some embodiments, a first Fc polypeptide or a second Fc polypeptide comprises amino acid sequence having at least about 99% identity to SEQ ID NO: 23.

In some embodiments, a first Fc polypeptide or a second Fc polypeptide comprises amino acid sequence of SEQ ID NO: 24. SEQ ID NO: 24 comprises "hole mutations" with cleavage substrate of MPYDLYHP (SEQ ID NO: 5).

```
                                         (SEQ ID NO: 24)
DKTHTCPPCPAPELLGGPSVFLFPPKPKDTLMISRTPEVTCVVVD

VSHEDPEVKFNWYVDGVEVHNAKTKPREEQYASTYRVVSVLTVLH

QDWLNGKEYKCKVSNKALPAPIEKTISKAKGQPREPQVCTLPPSR

DELTKNQVSLSCAVKGFYPSDIAVEWESNGQPENNYKTTPPVLDS

DGSFFLVSKLTVDKSRWQQGNVFSCSVMHEALHNHYTQKMPYDLY

HP
```

In some embodiments, a first Fc polypeptide or a second Fc polypeptide comprises amino acid sequence having at least about 85% identity to SEQ ID NO: 24. In some embodiments, a first Fc polypeptide or a second Fc polypeptide comprises amino acid sequence having at least about 90% identity to SEQ ID NO: 24. In some embodiments, a first Fc polypeptide or a second Fc polypeptide comprises amino acid sequence having at least about 91% identity to SEQ ID NO: 24. In some embodiments, a first Fc polypeptide or a second Fc polypeptide comprises amino acid sequence having at least about 92% identity to SEQ ID NO: 24. In some embodiments, a first Fc polypeptide or a second Fc polypeptide comprises amino acid sequence having at least about 93% identity to SEQ ID NO: 24. In some embodiments, a first Fc polypeptide or a second Fc polypeptide comprises amino acid sequence having at least about 94% identity to SEQ ID NO: 24. In some embodiments, a first Fc polypeptide or a second Fc polypeptide comprises amino acid sequence having at least about 95% identity to SEQ ID NO: 24. In some embodiments, a first Fc polypeptide or a second Fc polypeptide comprises amino acid sequence having at least about 96% identity to SEQ ID NO: 24. In some embodiments, a first Fc polypeptide or a second Fc polypeptide comprises amino acid sequence having at least about 97% identity to SEQ ID NO: 24. In some embodiments, a first Fc polypeptide or a second Fc polypeptide comprises amino acid sequence having at least about 98% identity to SEQ ID NO: 24. In some embodiments, a first Fc polypeptide or a second Fc polypeptide comprises amino acid sequence having at least about 99% identity to SEQ ID NO: 24.

In some embodiments, a first Fc polypeptide or a second Fc polypeptide comprises amino acid sequence of SEQ ID NO: 25. SEQ ID NO: 25 comprises "hole mutations" with cleavage substrate of APAGLIVPYN (SEQ ID NO: 7).

```
                                          (SEQ ID NO: 25)
DKTHTCPPCPAPELLGGPSVFLFPPKPKDTLMISRTPEVTCVVVD

VSHEDPEVKFNWYVDGVEVHNAKTKPREEQYASTYRVVSVLTVLH

QDWLNGKEYKCKVSNKALPAPIEKTISKAKGQPREPQVCTLPPSR

DELTKNQVSLSCAVKGFYPSDIAVEWESNGQPENNYKTTPPVLDS

DGSFFLVSKLTVDKSRWQQGNVFSCSVMHEALHNHYTAPAGLIVP

YN
```

In some embodiments, a first Fc polypeptide or a second Fc polypeptide comprises amino acid sequence having at least about 85% identity to SEQ ID NO: 25. In some embodiments, a first Fc polypeptide or a second Fc polypeptide comprises amino acid sequence having at least about 90% identity to SEQ ID NO: 25. In some embodiments, a first Fc polypeptide or a second Fc polypeptide comprises amino acid sequence having at least about 91% identity to SEQ ID NO: 25. In some embodiments, a first Fc polypeptide or a second Fc polypeptide comprises amino acid sequence having at least about 92% identity to SEQ ID NO: 25. In some embodiments, a first Fc polypeptide or a second Fc polypeptide comprises amino acid sequence having at least about 93% identity to SEQ ID NO: 25. In some embodiments, a first Fc polypeptide or a second Fc polypeptide comprises amino acid sequence having at least about 94% identity to SEQ ID NO: 25. In some embodiments, a first Fc polypeptide or a second Fc polypeptide comprises amino acid sequence having at least about 95% identity to SEQ ID NO: 25. In some embodiments, a first Fc polypeptide or a second Fc polypeptide comprises amino acid sequence having at least about 96% identity to SEQ ID NO:

25. In some embodiments, a first Fc polypeptide or a second Fc polypeptide comprises amino acid sequence having at least about 97% identity to SEQ ID NO: 25. In some embodiments, a first Fc polypeptide or a second Fc polypeptide comprises amino acid sequence having at least about 98% identity to SEQ ID NO: 25. In some embodiments, a first Fc polypeptide or a second Fc polypeptide comprises amino acid sequence having at least about 99% identity to SEQ ID NO: 25.

In some embodiments, a first Fc polypeptide or a second Fc polypeptide comprises amino acid sequence of SEQ ID NO: 26. SEQ ID NO: 26 comprises "hole mutations" with cleavage substrate of PANLVAPDP (SEQ ID NO: 9).

```
                                          (SEQ ID NO: 26)
DKTHTCPPCPAPELLGGPSVFLFPPKPKDTLMISRTPEVTCVVVD

VSHEDPEVKENWYVDGVEVHNAKTKPREEQYASTYRVVSVLTVLH

QDWLNGKEYKCKVSNKALPAPIEKTISKAKGQPREPQVCTLPPSR

DELTKNQVSLSCAVKGFYPSDIAVEWESNGQPENNYKTTPPVLDS

DGSFFLVSKLTVDKSRWQQGNVFSCSVMHEALHNHYTPANLVAPD

P
```

In some embodiments, a first Fc polypeptide or a second Fc polypeptide comprises amino acid sequence having at least about 85% identity to SEQ ID NO: 26. In some embodiments, a first Fc polypeptide or a second Fc polypeptide comprises amino acid sequence having at least about 90% identity to SEQ ID NO: 26. In some embodiments, a first Fc polypeptide or a second Fc polypeptide comprises amino acid sequence having at least about 91% identity to SEQ ID NO: 26. In some embodiments, a first Fc polypeptide or a second Fc polypeptide comprises amino acid sequence having at least about 92% identity to SEQ ID NO: 26. In some embodiments, a first Fc polypeptide or a second Fc polypeptide comprises amino acid sequence having at least about 93% identity to SEQ ID NO: 26. In some embodiments, a first Fc polypeptide or a second Fc polypeptide comprises amino acid sequence having at least about 94% identity to SEQ ID NO: 26. In some embodiments, a first Fc polypeptide or a second Fc polypeptide comprises amino acid sequence having at least about 95% identity to SEQ ID NO: 26. In some embodiments, a first Fc polypeptide or a second Fc polypeptide comprises amino acid sequence having at least about 96% identity to SEQ ID NO: 26. In some embodiments, a first Fc polypeptide or a second Fc polypeptide comprises amino acid sequence having at least about 97% identity to SEQ ID NO: 26. In some embodiments, a first Fc polypeptide or a second Fc polypeptide comprises amino acid sequence having at least about 98% identity to SEQ ID NO: 26. In some embodiments, a first Fc polypeptide or a second Fc polypeptide comprises amino acid sequence having at least about 99% identity to SEQ ID NO: 26.

In some embodiments, a first Fc polypeptide or a second Fc polypeptide comprises amino acid sequence of SEQ ID NO: 27. SEQ ID NO: 27 comprises "hole mutations" with cleavage substrate of GGPLGL (SEQ ID NO: 3).

```
                                          (SEQ ID NO: 27)
DKTHTCPPCPAPELLGGPSVFLFPPKPKDTLMISRTPEVTCVVVD

VSHEDPEVKFNWYVDGVEVHNAKTKPREEQYASTYRVVSVLTVLH
```

53

-continued

```
QDWLNGKEYKCKVSNKALPAPIEKTISKAKGQPREPQVCTLPPSR

DELTKNQVSLSCAVKGFYPSDIAVEWESNGQPENNYKTTPPVLDS

DGSFFLVSKLTVDKSRWQQGNVFSCSVMHEALHNHYTQKSLGGPL

GL
```

In some embodiments, a first Fc polypeptide or a second Fc polypeptide comprises amino acid sequence having at least about 85% identity to SEQ ID NO: 27. In some embodiments, a first Fc polypeptide or a second Fc polypeptide comprises amino acid sequence having at least about 90% identity to SEQ ID NO: 27. In some embodiments, a first Fc polypeptide or a second Fc polypeptide comprises amino acid sequence having at least about 91% identity to SEQ ID NO: 27. In some embodiments, a first Fc polypeptide or a second Fc polypeptide comprises amino acid sequence having at least about 92% identity to SEQ ID NO: 27. In some embodiments, a first Fc polypeptide or a second Fc polypeptide comprises amino acid sequence having at least about 93% identity to SEQ ID NO: 27. In some embodiments, a first Fc polypeptide or a second Fc polypeptide comprises amino acid sequence having at least about 94% identity to SEQ ID NO: 27. In some embodiments, a first Fc polypeptide or a second Fc polypeptide comprises amino acid sequence having at least about 95% identity to SEQ ID NO: 27. In some embodiments, a first Fc polypeptide or a second Fc polypeptide comprises amino acid sequence having at least about 96% identity to SEQ ID NO: 27. In some embodiments, a first Fc polypeptide or a second Fc polypeptide comprises amino acid sequence having at least about 97% identity to SEQ ID NO: 27. In some embodiments, a first Fc polypeptide or a second Fc polypeptide comprises amino acid sequence having at least about 98% identity to SEQ ID NO: 27. In some embodiments, a first Fc polypeptide or a second Fc polypeptide comprises amino acid sequence having at least about 99% identity to SEQ ID NO: 27.

In some embodiments, an Fc domain comprises a first Fc polypeptide comprising an amino acid sequence of SEQ ID NO: 33 and a second Fc polypeptide comprising an amino acid sequence of SEQ ID NO: 23.

In some embodiments, an Fc domain comprises a first Fc polypeptide comprising an amino acid sequence of SEQ ID NO: 33 and a second Fc polypeptide comprising an amino acid sequence of SEQ ID NO: 24.

In some embodiments, an Fc domain comprises a first Fc polypeptide comprising an amino acid sequence of SEQ ID NO: 33 and a second Fc polypeptide comprising an amino acid sequence of SEQ ID NO: 25.

In some embodiments, an Fc domain comprises a first Fc polypeptide comprising an amino acid sequence of SEQ ID NO: 33 and a second Fc polypeptide comprising an amino acid sequence of SEQ ID NO: 26.

In some embodiments, an Fc domain comprises a first Fc polypeptide comprising an amino acid sequence of SEQ ID NO: 33 and a second Fc polypeptide comprising an amino acid sequence of SEQ ID NO: 27.

Targeting Moieties

In some embodiments, the masked IL-2 cytokines described herein comprise a targeting moiety (e.g., a targeted cytokine). Accordingly, the present invention also provides, among other things, a targeted cytokine which comprises a targeting moiety, a cytokine or a variant thereof (e.g., an IL-2 polypeptide), a masking moiety (e.g., an anti-IL-2 VHH described herein), and a carrier moiety. In some embodiments, a targeted cytokine comprises a targeting moiety, an IL-2 polypeptide, a masking moiety, and an Fc domain. Targeted cytokines of the present invention become active at the site of disease and are able to specifically target a cell of interest for effective treatment of cancer without causing undesired side effects.

Targeted IL-2 polypeptides according to the disclosure can combine an IL-2 polypeptide or functional fragment thereof as described anywhere herein; a masking moiety as described anywhere herein; first and second Fc domains as described anywhere herein; cleavable and non-cleavable linkers as described anywhere herein; and targeting moieties as described anywhere herein.

Provided herein is a targeted cytokine that comprises a targeting moiety. In some embodiments, a targeting moiety comprises an antigen-binding moiety that binds to an antigen expressed on the surface of a target cell.

In some embodiments, the targeting moiety comprises an antigen-binding moiety, wherein the antigen is expressed on an immune cell. In some embodiments, the targeting moiety comprises an antigen-binding moiety, wherein the antigen is selected from PD-1, PD-L1, CTLA-4, TIGIT, TIM-3, LAG-3, OX40, DR5, ICOS, GITR, CD73, CD39, CD25, CD16a, CD8, KLRC1, KLRD1, KLRB1, CD40, CD137, CD28 and CD16b.

In some embodiments, a targeting moiety specifically binds PD-1, PD-L1, PD-L2, CTLA-4, TIGIT, TIM-3, LAG-3, CD25, CD16a, CD16b, OX40, DR5, ICOS, GITR, NKG2D, KLRC1, KLRD1, KLRB1, NKP44, NKP30, BCMA, human epidermal growth factor receptor 2 (HER2), MICA, DLK1, human epidermal growth factor receptor 3 (HER3), delta-like protein 3 (DLL3), delta-like protein 4 (DLL4), epidermal growth factor receptor (EGFR), glypican-3 (GPC3), c-MET, vascular endothelial growth factor receptor 1 (VEGF Rl), vascular endothelial growth factor receptor 2 (VEG FR2), Nectin-4, Liv-1, glycoprotein NMB (GPNMB), prostate specific membrane antigen (PSMA), Trop-2, carbonic anhydrase IX (CA9), endothelin B receptor (ETBR), six transmembrane epithelial antigen of the prostate 1 (STEAPI), NAPI2B, folate receptor alpha (FR-a), SLIT and NTRK-like protein 6 (SLITRK6), carbonic anhydrase VI (CA6), ectonucleotide pyrophosphatase/phosphodiesterase family member 3 (ENPP3), mesothelin, trophoblast glycoprotein (TPBG), CD19, CD8, CD20, CD22, CD28, CD33, CD39, CD40, CD56, CD66e, CD70, CD73, CD74, CD79b, CD98, CD123, CD137, CD138, CD352, CD47, signal-regulatory protein alpha (SIRPa), Claudin 18.2, Claudin 6, 5T4, fibroblast activation protein alpha (FAPa), fibronectin, the melanoma-associated chondroitin sulfate proteoglycan (MCSP), epithelial cellular adhesion molecule (EPCAM), or combinations thereof.

In some embodiments, a targeting moiety binds a tumor-associated antigen. In some embodiments, a targeting moiety is an antibody or an antigen binding fragment that binds a tumor-associated antigen. In some embodiments, a targeting moiety is a bispecific antibody or an antigen binding fragment that binds a tumor-associated antigen. In some embodiments, a targeting moiety is an anti-alpha-fetoprotein (AFP) antibody or a fragment thereof. In some embodiments, a targeting moiety is an anti-B2M antibody or a fragment thereof. In some embodiments, a targeting moiety is an anti-beta-human chorionic gonadotropin (beta-hCG) antibody or a fragment thereof. In some embodiments, a targeting moiety is an anti-CD117 antibody or a fragment thereof. In some embodiments, a targeting moiety is an anti-CD19 antibody or a fragment thereof. In some embodiments, a targeting moiety is an anti-CD20 antibody or a fragment thereof. In some embodiments, a targeting moiety is an anti-CD22 antibody or a fragment thereof. In some embodiments, a targeting moiety is an anti-CD25 antibody or a fragment thereof. In some embodiments, a targeting moiety is an anti-CD30 antibody or a fragment thereof. In some embodiments, a targeting moiety is an anti-CD33 antibody or a fragment thereof. In some embodiments, a targeting moiety is an anti-CD151 antibody or a fragment thereof. In some embodiments, a targeting moiety is an anti-MUC-1 antibody or a fragment thereof.

PD-1 Targeting Moiety

In some embodiments, a targeting moiety specifically binds PD-1. In some embodiments, a targeting moiety is an anti-PD1 Fab. In some embodiments, a targeting moiety is an anti-PD1 scFv.

In some embodiments, the targeting moiety is derived from an anti-PD1 antibody. In some embodiments, the targeting moiety is derived from pembrolizumab or nivolumab. In some embodiments, the targeting moiety is derived from pembrolizumab. In some embodiments, the targeting moiety is derived from nivolumab.

In some embodiments, a targeting moiety binds PD-1.

In some embodiments, a targeting moiety comprises an agent, a peptide, or a polypeptide that specifically binds to a target.

In some embodiments, a targeting moiety comprises a Fab, a single chain Fv (scFv), a single domain antibody (VHH), one or more CDRs, a variable heavy chain (VH), a variable light chain (VL), a Fab-like bispecific antibodies (bsFab), a single-domain antibody-linked Fab (s-Fab), an antibody, or a combination thereof. In some embodiments, a targeting moiety comprises a Fab. In some embodiments, a targeting moiety comprises a single chain Fv (scFv). In some embodiments, a targeting moiety comprises a single domain antibody (VHH). In some embodiments, a targeting moiety comprises one or more CDRs. In some embodiments, a targeting moiety comprises a variable heavy chain (VH). In some embodiments, a targeting moiety comprises a variable light chain (VL). In some embodiments, a targeting moiety comprises a Fab-like bispecific antibodies (bsFab). In some embodiments, a targeting moiety comprises a single-domain antibody-linked Fab (s-Fab). In some embodiments, a targeting moiety comprises an antibody or a fragment thereof.

In some embodiments, the targeting moiety comprises a heavy chain variable region or a light chain variable region of pembrolizumab.

In some embodiments, a targeting moiety comprises a heavy chain variable region of

```
                                         (SEQ ID NO: 41)
QVQLVQSGVEVKKPGASVKVSCKASGYTFTNYYMYWVRQAPGQGL

EWMGGINPSNGGTNFNEKFKNRVTLTTDSSTTTAYMELKSLQFDD

TAVYYCARRDYRFDMGFDYWGQGTTVTVSS.
```

In some embodiments, a targeting moiety comprises an amino acid sequence having at least about 80%, 85%, 90%, 91%, 92% 93%, 94%, 95%, 96%, 97% 98% or 99% sequence identity to SEQ ID NO: 41. In some embodiments, a targeting moiety comprises an amino acid sequence of SEQ ID NO: 41.

In some embodiments, a targeting moiety comprises a heavy chain variable and constant region of:

```
                                         (SEQ ID NO: 49)
QVQLVQSGVEVKKPGASVKVSCKASGYTFTNYYMYWVRQAPGQGL

EWMGGINPSNGGTNFNEKFKNRVTLTTDSSTTTAYMELKSLQFDD

TAVYYCARRDYRFDMGFDYWGQGTTVTVSSASTKGPSVFPLAPSS

KSTSGGTAALGCLVKDYFPEPVTVSWNSGALTSGVHTFPAVLQSS

GLYSLSSVVTVPSSSLGTQTYICNVNHKPSNTKVDKKVEPKSC.
```

In some embodiments, a targeting moiety comprises an amino acid sequence having at least about 80%, 85%, 90%, 91%, 92% 93%, 94%, 95%, 96%, 97% 98% or 99% sequence identity to SEQ ID NO: 49. In some embodiments, a targeting moiety comprises an amino acid sequence of SEQ ID NO: 49.

In some embodiments, a targeting moiety comprises a heavy chain CDR1 sequence of GYTFTNYY (SEQ ID NO: 43), a heavy chain CDR2 sequence of INPSNGGT (SEQ ID NO: 44), and a heavy chain CDR3 sequence of ARRDYRFDMGFDY (SEQ ID NO: 45).

In some embodiments, a targeting moiety comprises a light chain variable region of

```
                                         (SEQ ID NO: 42)
EIVLTQSPATLSLSPGERATLSCRASKGVSTSGYSYLHWYQQKPG

QAPRLLIYLASYLESGVPARFSGSGSGTDFTLTISSLEPEDFAVY

YCQHSRDLPLTFGGGTKVEIKTSENLYFQ.
```

In some embodiments, a targeting moiety comprises an amino acid sequence having at least about 80%, 85%, 90%, 91%, 92% 93%, 94%, 95%, 96%, 97% 98% or 99% sequence identity to SEQ ID NO: 42. In some embodiments, a targeting moiety comprises an amino acid sequence identical to SEQ ID NO: 42.

In some embodiments, a targeting moiety comprises a light chain of

```
                                         (SEQ ID NO: 50)
EIVLTQSPATLSLSPGERATLSCRASKGVSTSGYSYLHWYQQKPG

QAPRLLIYLASYLESGVPARFSGSGSGTDFTLTISSLEPEDFAVY

YCQHSRDLPLTFGGGTKVEIKRTVAAPSVFIFPPSDEQLKSGTAS

VVCLLNNFYPREAKVQWKVDNALQSGNSQESVTEQDSKDSTYSLS

STLTLSKADYEKHKVYACEVTHQGLSSPVTKSFNRGEC.
```

In some embodiments, a targeting moiety comprises an amino acid sequence having at least about 80%, 85%, 90%, 91%, 92% 93%, 94%, 95%, 96%, 97% 98% or 99% sequence identity to SEQ ID NO: 50. In some embodiments, a targeting moiety comprises an amino acid sequence identical to SEQ ID NO: 50.

In some embodiments, a targeting moiety comprises a light chain CDR1 sequence of KGVSTSGYSY (SEQ ID NO: 46), a light chain CDR2 sequence of LAS (SEQ ID NO: 47), and a light chain CDR3 sequence of QHSRDLPLT (SEQ ID NO: 48).

In some embodiments, a targeting moiety comprises a HCDR1 of SEQ ID NO: 43, a HCDR2 of SEQ ID NO: 44, a HCDR3 of SEQ ID NO: 45, a LCDR1 of SEQ ID NO: 46, a LCDR2 of SEQ ID NO: 47, and a LCDR3 of SEQ ID NO: 48.

In some embodiments, the targeting moiety comprises a heavy chain variable region or a light chain variable region of nivolumab.

In some embodiments, a targeting moiety comprises a heavy chain variable region of

```
                                          (SEQ ID NO: 51)
QVQLVESGGGVVQPGRSLRLDCKASGITFSNSGMHWVRQAPGKGL

EWVAVIWYDGSKRYYADSVKGRFTISRDNSKNTLFLQMNSLRAED

TAVYYCATNDDYWGQGTLVTVSS.
```

In some embodiments, a targeting moiety comprises an amino acid sequence having at least about 80%, 85%, 90%, 91%, 92% 93%, 94%, 95%, 96%, 97% 98% or 99% sequence identity to SEQ ID NO: 51. In some embodiments, a targeting moiety comprises an amino acid sequence identical to SEQ ID NO: 51.

In some embodiments, a targeting moiety comprises a heavy chain of

```
                                          (SEQ ID NO: 52)
QVQLVESGGG VVQPGRSLRL DCKASGITFS NSGMHWVRQA

PGKGLEWVAV IWYDGSKRYY ADSVKGRFTI SRDNSKNTLF

LQMNSLRAED TAVYYCATND DYWGQGTLVT VSSASTKGPS

VFPLAPCSRS TSESTAALGC LVKDYFPEPV TVSWNSGALT

SGVHTFPAVL QSSGLYSLSS VVTVPSSSLG TKTYTCNVDH

KPSNTKVDKR VESKYGPPCP PCPAPEFLGG PSVFLFPPKP

KDTLMISRTP EVTCVVVDVS QEDPEVQFNW YVDGVEVHNA

KTKPREEQFN STYRVVSVLT VLHQDWLNGK EYKCKVSNKG

LPSSIEKTIS KAKGQPREPQ VYTLPPSQEE MTKNQVSLTC

LVKGFYPSDI AVEWESNGQP ENNYKTTPPV LDSDGSFFLY

SRLTVDKSRW QEGNVFSCSV MHEALHNHYT QKSLSLSLGK
```

In some embodiments, a targeting moiety comprises an amino acid sequence having at least about 80%, 85%, 90%, 91%, 92% 93%, 94%, 95%, 96%, 97% 98% or 99% sequence identity to SEQ ID NO: 52. In some embodiments, a targeting moiety comprises an amino acid sequence identical to SEQ ID NO: 52.

In some embodiments, a targeting moiety comprises a heavy chain CDR1 sequence of GITFSNSG (SEQ ID NO: 53), a heavy chain CDR2 sequence of VIWYDGSKRYYADSVKG (SEQ ID NO: 54), and a heavy chain CDR3 sequence of

```
                                          (SEQ ID NO: 55)
            ATNDDY.
```

In some embodiments, a targeting moiety comprises a light chain variable region of

```
                                          (SEQ ID NO: 56)
EIVLTQSPATLSLSPGERATLSCRASQSVSSYLAWYQQKPGQAP

RLLIYDASNRATGIPARFSGSGSGTDFTLTISSLEPEDFAVYYC

QQSSNWPRTFGQGTKVEIK.
```

In some embodiments, a targeting moiety comprises an amino acid sequence having at least about 80%, 85%, 90%, 91%, 92% 93%, 94%, 95%, 96%, 97% 98% or 99% sequence identity to SEQ ID NO: 56. In some embodiments, a targeting moiety comprises an amino acid sequence identical to SEQ ID NO: 56.

In some embodiments, a targeting moiety comprises a light chain of

```
                                          (SEQ ID NO: 57)
EIVLTQSPAT LSLSPGERAT LSCRASQSVS SYLAWYQQKP

GQAPRLLIYD ASNRATGIPA RFSGSGSGTD FTLTISSLEP

EDFAVYYCQQ SSNWPRTFGQ GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGE.
```

In some embodiments, a targeting moiety comprises an amino acid sequence having at least about 80%, 85%, 90%, 91%, 92% 93%, 94%, 95%, 96%, 97% 98% or 99% sequence identity to SEQ ID NO: 57. In some embodiments, a targeting moiety comprises an amino acid sequence having identical to SEQ ID NO: 57.

In some embodiments, a targeting moiety comprises a light chain CDR1 sequence of QSVSSY (SEQ ID NO: 58), a light chain CDR2 sequence of DAS (SEQ ID NO: 59), a light chain CDR3 sequence of QQSSNWPRT (SEQ ID NO: 60).

In some embodiments, a targeting moiety comprises a heavy chain CDR1 sequence of GITFSNSG (SEQ ID NO: 53), a heavy chain CDR2 sequence of VIWYDGSKRYYADSVKG (SEQ ID NO: 54), a heavy chain CDR3 sequence of ATNDDY (SEQ ID NO: 55), a light chain CDR1 sequence of QSVSSY (SEQ ID NO: 58), a light chain CDR2 sequence of DAS (SEQ ID NO: 59), a light chain CDR3 sequence of QQSSNWPRT (SEQ ID NO: 60).

In some embodiments, a targeting domain is fused to an Fc polypeptide. In some embodiments, the C-terminus of a targeting domain is fused to the N-terminus of an Fc polypeptide. In some embodiments, the heavy chain of a Fab is fused to an Fc polypeptide. In some embodiments, the C-terminus of the heavy chain of a Fab is fused to the N-terminus of an Fc polypeptide. In some embodiments, an Fc polypeptide comprises a cleavage site.

In some embodiments, the targeting moiety comprises a heavy chain variable region, a light chain variable region and a CH1 domain. In some embodiments, the CH1 domain is derived from IgG1, IgG2, IgG3 or IgG4. In some embodiments, the CH1 domain is derived from IgG1. In some embodiments, the CH1 domain is derived from IgG4.

Exemplary Masked Cytokines

The present invention provides, among other things, a masked cytokine which comprises an IL-2 polypeptide or variant thereof, a masking moiety, and an engineered Fc domain. Masked IL-2 cytokines of the present invention become active at the tumor site of through tumor specific protease cleavage of a cleavage peptide located within the Fc domain of the masked cytokine that releases the IL-2 polypeptide upon cleavage.

In accordance with the present disclosure, the anti-IL-2 VHH antibody described herein can be utilized in any masked IL-2 cytokine. In some embodiments, the masked cytokine comprises a carrier moiety, a masking moiety, and a cytokine. In some embodiments, the masked cytokine comprises a carrier moiety, an IL-2 polypeptide as the cytokine, and an anti-IL-2 VHH antibody as the masking moiety.

In particular, the masked cytokine or targeted cytokine comprising VHH masking moieties of the present invention is characterized with (1) effective masking efficiency such that IL-2 cytokine's function is inhibited in undesired targets; (2) efficient IL-2 activation by protease to release the VHH masking moiety; (3) selective IL-2 activation in tumor, and not in plasma; and (4) in vivo efficacy (e.g., high tumor growth inhibition).

In some embodiments, a masked cytokine comprises an IL-2 polypeptide, a VHH masking moiety, an anti-PD1 targeting moiety, and an engineered Fc domain comprising a tumor-associated protease cleavage site.

In some embodiments, a masked cytokine comprises an IL-2 polypeptide, a masking moiety, a targeting moiety, and an engineered Fc domain comprising a tumor-associated protease cleavage site between positions 438-447 by EU numbering.

comprising a CDR1 of sequence GSIFSINVMG (SEQ ID NO: 14), a CDR2 of sequence AISSGGSTNYADSVKG (SEQ ID NO: 15), and a CDR3 of sequence ASSWYEDE-TDY (SEQ ID NO: 16), an anti-PD1 targeting moiety, and an engineered Fc domain comprising amino acid substitution of S442G, L443G, S444P, P445L and G447L.

In some embodiments, a masked cytokine comprises an attenuated IL-2 polypeptide comprising an amino acid substitution of F42E and C125A, a VHH masking moiety comprising a CDR1 of sequence GSIFSINVMG (SEQ ID NO: 14), a CDR2 of sequence AISSGGSTNYADSVKG (SEQ ID NO: 15), and a CDR3 of sequence ASSWYEDE-TDY (SEQ ID NO: 16), an anti-PD1 targeting moiety, and an engineered Fc domain comprising amino acid substitution of S444P, P445L and G447L.

In some embodiments, a masked cytokine comprises any one of constructs shown in Table D.

TABLE D

| Construct | IL-2 | Masking moiety | Cleavage substrate in Fc domain | Targeting moiety |
|-----------|------|----------------|---------------------------------|------------------|
| | | Exemplary Masked Cytokines of the Present Invention | | |
| UCM1 | Wild-type (C125A) | SEQ ID NO: 19 | SL-PLGL (SEQ ID NO: 2) | PD-1 |
| UCM2 | Not-alpha (R38A, F42A, Y45A, E62A, C125A) | SEQ ID NO: 19 | SL-PLGL (SEQ ID NO: 2) | PD-1 |
| UCM3 | Attenuated (F42E, C125A) | SEQ ID NO: 19 | SL-PLGL (SEQ ID NO: 2) | PD-1 |
| UCM4 | Not-alpha (R38A, F42A, Y45A, E62A, C125A) | SEQ ID NO: 19 | MPYDLYHP (SEQ ID NO: 5) | PD-1 |
| UCM5 | Not-alpha (R38A, F42A, Y45A, E62A, C125A) | SEQ ID NO: 19 | APAGLIVPYN (SEQ ID NO: 7) | PD-1 |
| UCM6 | Not-alpha (R38A, F42A, Y45A, E62A, C125A) | SEQ ID NO: 19 | PANLVAPDP (SEQ ID NO: 9) | PD-1 |
| UCM7 | Not-alpha (R38A, F42A, Y45A, E62A, C125A) | SEQ ID NO: 19 | GG-PLGL (SEQ ID NO: 3) | PD-1 |
| UCM8 | Not-alpha (R38A, F42A, Y45A, E62A, C125A) | SEQ ID NO: 19 | SL-PLGL (SEQ ID NO: 2) | PD-1 |
| UCM9 | Attenuated (F42E, C125A) | SEQ ID NO: 20 | SL-PLGL (SEQ ID NO: 2) | PD-1 |
| UCM10 | Attenuated (F42E, C125A) | SEQ ID NO: 20 | GG-PLGL (SEQ ID NO: 3) | PD-1 |
| UCM11 | Attenuated (F42E, C125A) | SEQ ID NO: 19 | GG-PLGL (SEQ ID NO: 3) | PD-1 |
| UCM12 | Attenuated (F42E, C125A) | SEQ ID NO: 21 | GG-PLGL (SEQ ID NO: 3) | PD-1 |

In some embodiments, a masked cytokine comprises an attenuated IL-2 polypeptide, a masking moiety, a targeting moiety, and an engineered Fc domain comprising a tumor-associated protease cleavage site between positions 438-447 by EU numbering.

In some embodiments, a masked cytokine comprises an attenuated IL-2 polypeptide comprising an amino acid substitution of F42E and C125A, a VHH masking moiety In some embodiments, a masked cytokine comprises an IL-2 polypeptide comprising an amino acid substitution of C125A, a VHH masking moiety comprising a CDR1 of sequence GSIFSINVMG (SEQ ID NO: 14), a CDR2 of sequence AISSGGSTNYADSVKG (SEQ ID NO: 15), and a CDR3 of sequence ASSWYEDETDY (SEQ ID NO: 16), an anti-PD1 targeting moiety comprising a HCDR1 of sequence GYTFTNYY (SEQ ID NO: 43), a HCDR2 of sequence INPSNGGT (SEQ ID NO: 44), a HCDR3 of sequence ARRDYRFDMGEDY (SEQ ID NO: 45), a LCDR1 of sequence KGVSTSGYSY (SEQ ID NO: 46), a LCDR2 of sequence LAS (SEQ ID NO: 47), a LCDR3 of sequence QHSRDLPLT (SEQ ID NO: 48), and an engineered Fc domain comprising amino acid substitutions of S444P, P445L and G447L.

In some embodiments, a masked cytokine comprises an IL-2 polypeptide comprising an amino acid substitutions of R38A, F42A, Y45A, E62A, and C125A, a VHH masking moiety comprising a CDR1 of sequence GSIFSINVMG (SEQ ID NO: 14), a CDR2 of sequence AISSGGSTNY-ADSVKG (SEQ ID NO: 15), and a CDR3 of sequence ASSWYEDETDY (SEQ ID NO: 16), an anti-PD1 targeting moiety comprising a HCDR1 of sequence GYTFTNYY (SEQ ID NO: 43), a HCDR2 of sequence INPSNGGT (SEQ ID NO: 44), a HCDR3 of sequence ARRDYRFDMGFDY (SEQ ID NO: 45), a LCDR1 of sequence KGVSTSGYSY (SEQ ID NO: 46), a LCDR2 of sequence LAS (SEQ ID NO: 47), a LCDR3 of sequence QHSRDLPLT (SEQ ID NO: 48), and an engineered Fc domain comprising amino acid substitutions of S444P, P445L and G447L.

In some embodiments, a masked cytokine comprises an IL-2 polypeptide comprising an amino acid substitutions of F42E, and C125A, a VHH masking moiety comprising a CDR1 of sequence GSIFSINVMG (SEQ ID NO: 14), a CDR2 of sequence AISSGGSTNYADSVKG (SEQ ID NO: 15), and a CDR3 of sequence ASSWYEDETDY (SEQ ID NO: 16), an anti-PD1 targeting moiety comprising a HCDR1 of sequence GYTFTNYY (SEQ ID NO: 43), a HCDR2 of sequence INPSNGGT (SEQ ID NO: 44), a HCDR3 of sequence ARRDYRFDMGFDY (SEQ ID NO: 45), a LCDR1 of sequence KGVSTSGYSY (SEQ ID NO: 46), a LCDR2 of sequence LAS (SEQ ID NO: 47), a LCDR3 of sequence QHSRDLPLT (SEQ ID NO: 48), and an engineered Fc domain comprising amino acid substitutions of S444P, P445L and G447L.

In some embodiments, a masked cytokine comprises an IL-2 polypeptide comprising an amino acid substitutions of R38A, F42A, Y45A, E62A, and C125A, a VHH masking moiety comprising a CDR1 of sequence GSIFSINVMG (SEQ ID NO: 14), a CDR2 of sequence AISSGGSTNY-ADSVKG (SEQ ID NO: 15), and a CDR3 of sequence ASSWYEDETDY (SEQ ID NO: 16), an anti-PD1 targeting moiety comprising a HCDR1 of sequence GYTFTNYY (SEQ ID NO: 43), a HCDR2 of sequence INPSNGGT (SEQ ID NO: 44), a HCDR3 of sequence ARRDYRFDMGEDY (SEQ ID NO: 45), a LCDR1 of sequence KGVSTSGYSY (SEQ ID NO: 46), a LCDR2 of sequence LAS (SEQ ID NO: 47), a LCDR3 of sequence QHSRDLPLT (SEQ ID NO: 48), and an engineered Fc domain comprising amino acid substitutions of S440M, L441P, S442Y, L443D, S444L, P445Y, G446H and G447P.

In some embodiments, a masked cytokine comprises an IL-2 polypeptide comprising an amino acid substitutions of R38A, F42A, Y45A, E62A, and C125A, a VHH masking moiety comprising a CDR1 of sequence GSIFSINVMG (SEQ ID NO: 14), a CDR2 of sequence AISSGGSTNY-ADSVKG (SEQ ID NO: 15), and a CDR3 of sequence ASSWYEDETDY (SEQ ID NO: 16), an anti-PD1 targeting moiety comprising a HCDR1 of sequence GYTFTNYY (SEQ ID NO: 43), a HCDR2 of sequence INPSNGGT (SEQ ID NO: 44), a HCDR3 of sequence ARRDYRFDMGFDY (SEQ ID NO: 45), a LCDR1 of sequence KGVSTSGYSY (SEQ ID NO: 46), a LCDR2 of sequence LAS (SEQ ID NO: 47), a LCDR3 of sequence QHSRDLPLT (SEQ ID NO: 48), and an engineered Fc domain comprising amino acid substitutions of Q438A, K439P, S440A, L441G, S442L, L443I, S444V, G446Y, and G447N.

In some embodiments, a masked cytokine comprises an IL-2 polypeptide comprising an amino acid substitutions of R38A, F42A, Y45A, E62A, and C125A, a VHH masking moiety comprising a CDR1 of sequence GSIFSINVMG (SEQ ID NO: 14), a CDR2 of sequence AISSGGSTNY-ADSVKG (SEQ ID NO: 15), and a CDR3 of sequence ASSWYEDETDY (SEQ ID NO: 16), an anti-PD1 targeting moiety comprising a HCDR1 of sequence GYTFTNYY (SEQ ID NO: 43), a HCDR2 of sequence INPSNGGT (SEQ ID NO: 44), a HCDR3 of sequence ARRDYRFDMGFDY (SEQ ID NO: 45), a LCDR1 of sequence KGVSTSGYSY (SEQ ID NO: 46), a LCDR2 of sequence LAS (SEQ ID NO: 47), a LCDR3 of sequence QHSRDLPLT (SEQ ID NO: 48), and an engineered Fc domain comprising amino acid substitutions Q438P, K439A, S440N, S442V, LA43A, S444P, P445D, and G446P.

In some embodiments, a masked cytokine comprises an IL-2 polypeptide comprising an amino acid substitutions of R38A, F42A, Y45A, E62A, and C125A, a VHH masking moiety comprising a CDR1 of sequence GSIFSINVMG (SEQ ID NO: 14), a CDR2 of sequence AISSGGSTNY-ADSVKG (SEQ ID NO: 15), and a CDR3 of sequence ASSWYEDETDY (SEQ ID NO: 16), an anti-PD1 targeting moiety comprising a HCDR1 of sequence GYTFTNYY (SEQ ID NO: 43), a HCDR2 of sequence INPSNGGT (SEQ ID NO: 44), a HCDR3 of sequence ARRDYRFDMGFDY (SEQ ID NO: 45), a LCDR1 of sequence KGVSTSGYSY (SEQ ID NO: 46), a LCDR2 of sequence LAS (SEQ ID NO: 47), a LCDR3 of sequence QHSRDLPLT (SEQ ID NO: 48), and an engineered Fc domain comprising amino acid substitutions S442G, L443G, S444P, P445L, and G447L.

In some embodiments, a masked cytokine comprises an IL-2 polypeptide comprising an amino acid substitutions of R38A, F42A, Y45A, E62A, and C125A, a VHH masking moiety comprising a CDR1 of sequence GSIFSINVMG (SEQ ID NO: 14), a CDR2 of sequence AISSGGSTNY-ADSVKG (SEQ ID NO: 15), and a CDR3 of sequence ASSWYEDETDY (SEQ ID NO: 16), an anti-PD1 targeting moiety comprising a HCDR1 of sequence GYTFTNYY (SEQ ID NO: 43), a HCDR2 of sequence INPSNGGT (SEQ ID NO: 44), a HCDR3 of sequence ARRDYRFDMGFDY (SEQ ID NO: 45), a LCDR1 of sequence KGVSTSGYSY (SEQ ID NO: 46), a LCDR2 of sequence LAS (SEQ ID NO: 47), a LCDR3 of sequence QHSRDLPLT (SEQ ID NO: 48), and an engineered Fc domain comprising amino acid substitutions S444P, P445L, and G447L.

In some embodiments, a masked cytokine comprises an IL-2 polypeptide comprising an amino acid substitutions of F42E, and C125A, a VHH masking moiety comprising a CDR1 of sequence GSIFSINVMG (SEQ ID NO: 14), a CDR2 of sequence AISSGGSTNYADSVKG (SEQ ID NO: 15), and a CDR3 of sequence ASSFYEDETDY (SEQ ID NO: 17), an anti-PD1 targeting moiety comprising a HCDR1 of sequence GYTFTNYY (SEQ ID NO: 43), a HCDR2 of sequence INPSNGGT (SEQ ID NO: 44), a HCDR3 of sequence ARRDYRFDMGFDY (SEQ ID NO: 45), a LCDR1 of sequence KGVSTSGYSY (SEQ ID NO: 46), a LCDR2 of sequence LAS (SEQ ID NO: 47), a LCDR3 of sequence QHSRDLPLT (SEQ ID NO: 48), and an engineered Fc domain comprising amino acid substitutions S444P, P445L, and G447L.

In some embodiments, a masked cytokine comprises an IL-2 polypeptide comprising an amino acid substitutions of F42E, and C125A, a VHH masking moiety comprising a CDR1 of sequence GSIFSINVMG (SEQ ID NO: 14), a CDR2 of sequence AISSGGSTNYADSVKG (SEQ ID NO: 15), and a CDR3 of sequence ASSFYEDETDY (SEQ ID NO: 17), an anti-PD1 targeting moiety comprising a HCDR1 of sequence GYTFTNYY (SEQ ID NO: 43), a HCDR2 of sequence INPSNGGT (SEQ ID NO: 44), a HCDR3 of sequence ARRDYRFDMGFDY (SEQ ID NO: 45), a LCDR1 of sequence KGVSTSGYSY (SEQ ID NO: 46), a LCDR2 of sequence LAS (SEQ ID NO: 47), a LCDR3 of sequence QHSRDLPLT (SEQ ID NO: 48), and an engineered Fc domain comprising amino acid substitutions S442G, L443G, S444P, P445L, and G447L.

In some embodiments, a masked cytokine comprises an IL-2 polypeptide comprising an amino acid substitutions of F42E, and C125A, a VHH masking moiety comprising a CDR1 of sequence GSIFSINVMG (SEQ ID NO: 14), a CDR2 of sequence AISSGGSTNYADSVKG (SEQ ID NO: 15), and a CDR3 of sequence ASSWYEDETDY (SEQ ID NO: 16), an anti-PD1 targeting moiety comprising a HCDR1 of sequence GYTFTNYY (SEQ ID NO: 43), a HCDR2 of sequence INPSNGGT (SEQ ID NO: 44), a HCDR3 of sequence ARRDYRFDMGFDY (SEQ ID NO: 45), a LCDR1 of sequence KGVSTSGYSY (SEQ ID NO: 46), a LCDR2 of sequence LAS (SEQ ID NO: 47), a LCDR3 of sequence QHSRDLPLT (SEQ ID NO: 48), and an engineered Fc domain comprising amino acid substitutions S442G, L443G, S444P, P445L, and G447L.

In some embodiments, a masked cytokine comprises an IL-2 polypeptide comprising an amino acid sequence of SEQ ID NO: 11, a VHH masking moiety comprising an amino acid sequence of SEQ ID NO: 19, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 23.

In some embodiments, a masked cytokine comprises an IL-2 polypeptide comprising an amino acid sequence of SEQ ID NO: 12, a VHH masking moiety comprising an amino acid sequence of SEQ ID NO: 19, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 23.

In some embodiments, a masked cytokine comprises an IL-2 polypeptide comprising an amino acid sequence of SEQ ID NO: 13, a VHH masking moiety comprising an amino acid sequence of SEQ ID NO: 19, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 23.

In some embodiments, a masked cytokine comprises an IL-2 polypeptide comprising an amino acid sequence of SEQ ID NO: 12, a VHH masking moiety comprising an amino acid sequence of SEQ ID NO: 19, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 24.

In some embodiments, a masked cytokine comprises an IL-2 polypeptide comprising an amino acid sequence of SEQ ID NO: 12, a VHH masking moiety comprising an amino acid sequence of SEQ ID NO: 19, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 25.

In some embodiments, a masked cytokine comprises an IL-2 polypeptide comprising an amino acid sequence of SEQ ID NO: 12, a VHH masking moiety comprising an amino acid sequence of SEQ ID NO: 19, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 26.

In some embodiments, a masked cytokine comprises an IL-2 polypeptide comprising an amino acid sequence of SEQ ID NO: 12, a VHH masking moiety comprising an amino acid sequence of SEQ ID NO: 19, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 27.

In some embodiments, a masked cytokine comprises an IL-2 polypeptide comprising an amino acid sequence of SEQ ID NO: 13, a VHH masking moiety comprising an amino acid sequence of SEQ ID NO: 20, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 23.

In some embodiments, a masked cytokine comprises an IL-2 polypeptide comprising an amino acid sequence of SEQ ID NO: 13, a VHH masking moiety comprising an amino acid sequence of SEQ ID NO: 20, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 27.

In some embodiments, a masked cytokine comprises an IL-2 polypeptide comprising an amino acid sequence of SEQ ID NO: 13, a VHH masking moiety comprising an amino acid sequence of SEQ ID NO: 19, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 27.

In some embodiments, a masked cytokine comprises an IL-2 polypeptide comprising an amino acid sequence of SEQ ID NO: 13, a VHH masking moiety comprising an amino acid sequence of SEQ ID NO: 21, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 27.

In some embodiments, a masked cytokine comprises an IL-2 polypeptide comprising an amino acid sequence of SEQ ID NO: 11, a VHH masking moiety comprising an amino acid sequence of SEQ ID NO: 19, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 23, wherein the IL-2 polypeptide is linked to the first Fc polypeptide, and the VHH masking moiety is linked to the second Fc polypeptide.

In some embodiments, a masked cytokine comprises an IL-2 polypeptide comprising an amino acid sequence of SEQ ID NO: 12, a VHH masking moiety comprising an amino acid sequence of SEQ ID NO: 19, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 23, wherein the IL-2 polypeptide is linked to the first Fc polypeptide, and the VHH masking moiety is linked to the second Fc polypeptide.

In some embodiments, a masked cytokine comprises an IL-2 polypeptide comprising an amino acid sequence of SEQ ID NO: 13, a VHH masking moiety comprising an amino acid sequence of SEQ ID NO: 19, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 23, wherein the IL-2 polypeptide is linked to the first Fc polypeptide, and the VHH masking moiety is linked to the second Fc polypeptide.

In some embodiments, a masked cytokine comprises an IL-2 polypeptide comprising an amino acid sequence of SEQ ID NO: 12, a VHH masking moiety comprising an amino acid sequence of SEQ ID NO: 19, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 24, wherein the IL-2 polypeptide is linked to the first Fc polypeptide, and the VHH masking moiety is linked to the second Fc polypeptide.

In some embodiments, a masked cytokine comprises an IL-2 polypeptide comprising an amino acid sequence of SEQ ID NO: 12, a VHH masking moiety comprising an amino acid sequence of SEQ ID NO: 19, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 25, wherein the IL-2 polypeptide is linked to the first Fc polypeptide, and the VHH masking moiety is linked to the second Fc polypeptide.

In some embodiments, a masked cytokine comprises an IL-2 polypeptide comprising an amino acid sequence of SEQ ID NO: 12, a VHH masking moiety comprising an amino acid sequence of SEQ ID NO: 19, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 26, wherein the IL-2 polypeptide is linked to the first Fc polypeptide, and the VHH masking moiety is linked to the second Fc polypeptide.

In some embodiments, a masked cytokine comprises an IL-2 polypeptide comprising an amino acid sequence of SEQ ID NO: 12, a VHH masking moiety comprising an amino acid sequence of SEQ ID NO: 19, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 27, wherein the IL-2 polypeptide is linked to the first Fc polypeptide, and the VHH masking moiety is linked to the second Fc polypeptide.

In some embodiments, a masked cytokine comprises an IL-2 polypeptide comprising an amino acid sequence of SEQ ID NO: 13, a VHH masking moiety comprising an amino acid sequence of SEQ ID NO: 20, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 23, wherein the IL-2 polypeptide is linked to the first Fc polypeptide, and the VHH masking moiety is linked to the second Fc polypeptide.

In some embodiments, a masked cytokine comprises an IL-2 polypeptide comprising an amino acid sequence of SEQ ID NO: 13, a VHH masking moiety comprising an amino acid sequence of SEQ ID NO: 20, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 27, wherein the IL-2 polypeptide is linked to the first Fc polypeptide, and the VHH masking moiety is linked to the second Fc polypeptide.

In some embodiments, a masked cytokine comprises an IL-2 polypeptide comprising an amino acid sequence of SEQ ID NO: 13, a VHH masking moiety comprising an amino acid sequence of SEQ ID NO: 19, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 27, wherein the IL-2 polypeptide is linked to the first Fc polypeptide, and the VHH masking moiety is linked to the second Fc polypeptide.

In some embodiments, a masked cytokine comprises an IL-2 polypeptide comprising an amino acid sequence of SEQ ID NO: 13, a VHH masking moiety comprising an amino acid sequence of SEQ ID NO: 21, an anti-PD1 targeting moiety comprising amino acid sequences of SEQ ID NOs: 41 and 42, and an engineered Fc domain comprising a first Fc polypeptide of SEQ ID NO: 33 and a second Fc polypeptide of SEQ ID NO: 27, wherein the IL-2 polypeptide is linked to the first Fc polypeptide, and the VHH masking moiety is linked to the second Fc polypeptide.

In some embodiments, a masked cytokine comprises a first polypeptide comprising an amino acid sequence of SEQ ID NO: 63, SEQ ID NO: 64, or SEQ ID NO: 65, a second polypeptide comprising an amino acid sequence of SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, or SEQ ID NO: 74, and a third polypeptide comprising an amino acid sequence of SEQ ID NO: 50.

In some embodiments, an IL-2 polypeptide is fused to a first Fc polypeptide via a GS linker. In some embodiments, an IL-2 polypeptide is fused to a first Fc polypeptide via a GGGGS (SEQ ID NO: 61) linker. In some embodiments, an IL-2 polypeptide is fused to a first Fc polypeptide via a GGGGSGGGGSGGGGS (SEQ ID NO: 62) linker.

In some embodiments, a VHH masking moiety is fused to a second Fc polypeptide via a GS linker. In some embodiments, a VHH masking moiety is fused to a second Fc polypeptide via a GGGGS (SEQ ID NO: 61) linker. In some embodiments, a VHH masking moiety is fused to a second Fc polypeptide via a GGGGSGGGGSGGGGS (SEQ ID NO: 62) linker.

SEQ ID NO: 63 comprises a variable heavy chain that binds to PD1, a non-cleavable Fc polypeptide, and an attenuated IL-2 from N- to C-terminus:

```
                                  (SEQ ID NO: 63)
QVQLVQSGVEVKKPGASVKVSCKASGYTFTNYYMYWVRQAPGQGL

EWMGGINPSNGGTNFNEKFKNRVTLTTDSSTTTAYMELKSLQFDD
```

-continued

TAVYYCARRDYRFDMGFDYWGQGTTVTVSSASTKGPSVFPLAPSS

KSTSGGTAALGCLVKDYFPEPVTVSWNSGALTSGVHTFPAVLQSS

GLYSLSSVVTVPSSSLGTQTYICNVNHKPSNTKVDKKVEPKSCDK

THTCPPCPAPELLGGPSVFLFPPKPKDTLMISRTPEVTCVVVDVS

HEDPEVKFNWYVDGVEVHNAKTKPREEQYASTYRVVSVLTVLHQD

WLNGKEYKCKVSNKALPAPIEKTISKAKGQPREPQVYTLPPCRDE

LTKNQVSLWCLVKGFYPSDIAVEWESNGQPENNYKTTPPVLDSDG

SFFLYSKLTVDKSRWQQGNVFSCSVMHEALHNRFTQKSLSLSPGG

GSSPPGGGSSGGGSGPAPTSSSTKKTQLQLEHLLLDLQMILNGIN

NYKNPKLTRMLTEKFYMPKKATELKHLQCLEEELKPLEEVLNLAQ

SKNFHLRPRDLISNINVIVLELKGSETTFMCEYADETATIVEFLN

RWITFAQSIISTLT

SEQ ID NO: 64 comprises a variable heavy chain that binds to PD1, a non-cleavable Fc polypeptide, and a wild-type IL-2 from N- to C-terminus:

(SEQ ID NO: 64)
QVQLVQSGVEVKKPGASVKVSCKASGYTFTNYYMYWVRQAPGQGL

EWMGGINPSNGGTNFNEKFKNRVTLTTDSSTTTAYMELKSLQFDD

TAVYYCARRDYRFDMGFDYWGQGTTVTVSSASTKGPSVFPLAPSS

KSTSGGTAALGCLVKDYFPEPVTVSWNSGALTSGVHTFPAVLQSS

GLYSLSSVVTVPSSSLGTQTYICNVNHKPSNTKVDKKVEPKSCDK

THTCPPCPAPELLGGPSVFLFPPKPKDTLMISRTPEVTCVVVDVS

HEDPEVKFNWYVDGVEVHNAKTKPREEQYASTYRVVSVLTVLHQD

WLNGKEYKCKVSNKALPAPIEKTISKAKGQPREPQVYTLPPCRDE

LTKNQVSLWCLVKGFYPSDIAVEWESNGQPENNYKTTPPVLDSDG

SFFLYSKLTVDKSRWQQGNVFSCSVMHEALHNRFTQKSLSLSPGG

GSSPPGGGSSGGGSGPAPTSSSTKKTQLQLEHLLLDLQMILNGIN

NYKNPKLTRMLTFKFYMPKKATELKHLQCLEEELKPLEEVLNLAQ

SKNFHLRPRDLISNINVIVLELKGSETTFMCEYADETATIVEFLN

RWITFAQSIISTLT

SEQ ID NO: 65 comprises a variable heavy chain that binds to PD1, a non-cleavable Fc polypeptide, and a not-alpha IL-2 from N- to C-terminus:

(SEQ ID NO: 65)
QVQLVQSGVEVKKPGASVKVSCKASGYTFTNYYMYWVRQAPGQGL

EWMGGINPSNGGTNFNEKFKNRVTLTTDSSTTTAYMELKSLQFDD

TAVYYCARRDYRFDMGFDYWGQGTTVTVSSASTKGPSVFPLAPSS

KSTSGGTAALGCLVKDYFPEPVTVSWNSGALTSGVHTFPAVLQSS

GLYSLSSVVTVPSSSLGTQTYICNVNHKPSNTKVDKKVEPKSCDK

THTCPPCPAPELLGGPSVFLFPPKPKDTLMISRTPEVTCVVVDVS

HEDPEVKFNWYVDGVEVHNAKTKPREEQYASTYRVVSVLTVLHQD

WLNGKEYKCKVSNKALPAPIEKTISKAKGQPREPQVYTLPPCRDE

-continued

LTKNQVSLWCLVKGFYPSDIAVEWESNGQPENNYKTTPPVLDSDG

SFFLYSKLTVDKSRWQQGNVFSCSVMHEALHNRFTQKSLSLSPGG

GSSPPGGGSSGGGSGPAPTSSSTKKTQLQLEHLLLDLQMILNGIN

NYKNPKLTAMLTAKFAMPKKATELKHLQCLEEALKPLEEVLNLAQ

SKNFHLRPRDLISNINVIVLELKGSETTFMCEYADETATIVEFLN

RWITFAQSIISTLT

SEQ ID NO: 66 comprises a variable heavy chain that binds to PD1, an Fc polypeptide comprising SLPLGL (SEQ ID NO: 2) cleavage substrate, and a VHH masking moiety from N- to C-terminus:

(SEQ ID NO: 66)
QVQLVQSGVEVKKPGASVKVSCKASGYTFTNYYMYWVRQAPGQGL

EWMGGINPSNGGTNFNEKFKNRVTLTTDSSTTTAYMELKSLQFDD

TAVYYCARRDYRFDMGFDYWGQGTTVTVSSASTKGPSVFPLAPSS

KSTSGGTAALGCLVKDYFPEPVTVSWNSGALTSGVHTFPAVLQSS

GLYSLSSVVTVPSSSLGTQTYICNVNHKPSNTKVDKKVEPKSCDK

THTCPPCPAPELLGGPSVFLFPPKPKDTLMISRTPEVTCVVVDVS

HEDPEVKFNWYVDGVEVHNAKTKPREEQYASTYRVVSVLTVLHQD

WLNGKEYKCKVSNKALPAPIEKTISKAKGQPREPQVCTLPPSRDE

LTKNQVSLSCAVKGFYPSDIAVEWESNGQPENNYKTTPPVLDSDG

SFFLVSKLTVDKSRWQQGNVFSCSVMHEALHNHYTQKSLSLPLGL

GGSSGSGGSGGGSGSGGGEVQLVESGGGLVQPGGSLRLSCAASGS

IFSINVMGWYRQAPGKQRELVAAISSGGSTNYADSVKGRFTISRD

NAKNTVYLQMNSLKPEDTAVYYCMYASSWYEDETDYWGQGTQVTV

SS

SEQ ID NO: 67 comprises a variable heavy chain that binds to PD1, an Fc polypeptide comprising GGPLGL (SEQ ID NO: 3) cleavage substrate, and a VHH masking moiety from N- to C-terminus:

(SEQ ID NO: 67)
QVQLVQSGVEVKKPGASVKVSCKASGYTFTNYYMYWVRQAPGQGL

EWMGGINPSNGGTNFNEKFKNRVTLTTDSSTTTAYMELKSLQFDD

TAVYYCARRDYRFDMGFDYWGQGTTVTVSSASTKGPSVFPLAPSS

KSTSGGTAALGCLVKDYFPEPVTVSWNSGALTSGVHTFPAVLQSS

GLYSLSSVVTVPSSSLGTQTYICNVNHKPSNTKVDKKVEPKSCDK

THTCPPCPAPELLGGPSVFLFPPKPKDTLMISRTPEVTCVVVDVS

HEDPEVKFNWYVDGVEVHNAKTKPREEQYASTYRVVSVLTVLHQD

WLNGKEYKCKVSNKALPAPIEKTISKAKGQPREPQVCTLPPSRDE

LTKNQVSLSCAVKGFYPSDIAVEWESNGQPENNYKTTPPVLDSDG

SFFLVSKLTVDKSRWQQGNVFSCSVMHEALHNHYTQKSLGGPLGL

GGSSGSGGSGGGSGSGGGEVQLVESGGGLVQPGGSLRLSCAASGS

IFSINVMGWYRQAPGKQRELVAAISSGGSTNYADSVKGRFTISRD

-continued

NAKNTVYLQMNSLKPEDTAVYYCMYASSWYEDETDYWGQGTQVTV

SS

SEQ ID NO: 68 comprises a variable heavy chain that binds to PD1, an Fc polypeptide comprising MPYDLYHP (SEQ ID NO: 5) cleavage substrate, and a VHH masking moiety from N- to C-terminus:

(SEQ ID NO: 68)

QVQLVQSGVEVKKPGASVKVSCKASGYTFTNYYMYWVRQAPGQGL

EWMGGINPSNGGTNFNEKFKNRVTLTTDSSTTTAYMELKSLQFDD

TAVYYCARRDYRFDMGFDYWGQGTTVTVSSASTKGPSVFPLAPSS

KSTSGGTAALGCLVKDYFPEPVTVSWNSGALTSGVHTFPAVLQSS

GLYSLSSVVTVPSSSLGTQTYICNVNHKPSNTKVDKKVEPKSCDK

THTCPPCPAPELLGGPSVFLFPPKPKDTLMISRTPEVTCVVVDVS

HEDPEVKFNWYVDGVEVHNAKTKPREEQYASTYRVVSVLTVLHQD

WLNGKEYKCKVSNKALPAPIEKTISKAKGQPREPQVCTLPPSRDE

LTKNQVSLSCAVKGFYPSDIAVEWESNGQPENNYKTTPPVLDSDG

SFFLVSKLTVDKSRWQQGNVFSCSVMHEALHNHYTQKMPYDLYHP

GGSSGSGGSGGGSGSGGGEVQLVESGGGLVQPGGSLRLSCAASGS

IFSINVMGWYRQAPGKQRELVAAISSGGSTNYADSVKGRFTISRD

NAKNTVYLQMNSLKPEDTAVYYCMYASSWYEDETDYWGQGTQVTV

SS

SEQ ID NO: 69 comprises a variable heavy chain that binds to PD1, an Fc polypeptide comprising APAGLIVPYN (SEQ ID NO: 7) cleavage substrate, and a VHH masking moiety from N- to C-terminus:

(SEQ ID NO: 69)

QVQLVQSGVEVKKPGASVKVSCKASGYTFTNYYMYWVRQAPGQGL

EWMGGINPSNGGTNFNEKFKNRVTLTTDSSTTTAYMELKSLQFDD

TAVYYCARRDYRFDMGFDYWGQGTTVTVSSASTKGPSVFPLAPSS

KSTSGGTAALGCLVKDYFPEPVTVSWNSGALTSGVHTFPAVLQSS

GLYSLSSVVTVPSSSLGTQTYICNVNHKPSNTKVDKKVEPKSCDK

THTCPPCPAPELLGGPSVFLFPPKPKDTLMISRTPEVTCVVVDVS

HEDPEVKFNWYVDGVEVHNAKTKPREEQYASTYRVVSVLTVLHQD

WLNGKEYKCKVSNKALPAPIEKTISKAKGQPREPQVCTLPPSRDE

LTKNQVSLSCAVKGFYPSDIAVEWESNGQPENNYKTTPPVLDSDG

SFFLVSKLTVDKSRWQQGNVFSCSVMHEALHNHYTAPAGLIVPYN

GGSSGSGGSGGGSGSGGGEVQLVESGGGLVQPGGSLRLSCAASGS

IFSINVMGWYRQAPGKQRELVAAISSGGSTNYADSVKGRFTISRD

NAKNTVYLQMNSLKPEDTAVYYCMYASSWYEDETDYWGQGTQVTV

SS

SEQ ID NO: 70 comprises a variable heavy chain that binds to PD1, an Fc polypeptide comprising PANLVAPDP (SEQ ID NO: 9) cleavage substrate, and a VHH masking moiety from N- to C-terminus:

(SEQ ID NO: 70)

QVQLVQSGVEVKKPGASVKVSCKASGYTFTNYYMYWVRQAPGQGL

EWMGGINPSNGGTNFNEKFKNRVTLTTDSSTTTAYMELKSLQFDD

TAVYYCARRDYRFDMGFDYWGQGTTVTVSSASTKGPSVFPLAPSS

KSTSGGTAALGCLVKDYFPEPVTVSWNSGALTSGVHTFPAVLQSS

GLYSLSSVVTVPSSSLGTQTYICNVNHKPSNTKVDKKVEPKSCDK

THTCPPCPAPELLGGPSVFLFPPKPKDTLMISRTPEVTCVVVDVS

HEDPEVKFNWYVDGVEVHNAKTKPREEQYASTYRVVSVLTVLHQD

WLNGKEYKCKVSNKALPAPIEKTISKAKGQPREPQVCTLPPSRDE

LTKNQVSLSCAVKGFYPSDIAVEWESNGQPENNYKTTPPVLDSDG

SFFLVSKLTVDKSRWQQGNVFSCSVMHEALHNHYTPANLVAPDPG

GGSSGSGGSGGGSGSGGGEVQLVESGGGLVQPGGSLRLSCAASGS

IFSINVMGWYRQAPGKQRELVAAISSGGSTNYADSVKGRFTISRD

NAKNTVYLQMNSLKPEDTAVYYCMYASSWYEDETDYWGQGTQVTV

SS

SEQ ID NO: 71 comprises a variable heavy chain that binds to PD1, an Fc polypeptide comprising SLPLGL (SEQ ID NO: 2) cleavage substrate, and a VHH masking moiety from N- to C-terminus:

(SEQ ID NO: 71)

QVQLVQSGVEVKKPGASVKVSCKASGYTFTNYYMYWVRQAPGQGL

EWMGGINPSNGGTNFNEKFKNRVTLTTDSSTTTAYMELKSLQFDD

TAVYYCARRDYRFDMGFDYWGQGTTVTVSSASTKGPSVFPLAPSS

KSTSGGTAALGCLVKDYFPEPVTVSWNSGALTSGVHTFPAVLQSS

GLYSLSSVVTVPSSSLGTQTYICNVNHKPSNTKVDKKVEPKSCDK

THTCPPCPAPELLGGPSVFLFPPKPKDTLMISRTPEVTCVVVDVS

HEDPEVKFNWYVDGVEVHNAKTKPREEQYASTYRVVSVLTVLHQD

WLNGKEYKCKVSNKALPAPIEKTISKAKGQPREPQVCTLPPSRDE

LTKNQVSLSCAVKGFYPSDIAVEWESNGQPENNYKTTPPVLDSDG

SFFLVSKLTVDKSRWQQGNVFSCSVMHEALHNHYTQKSLSLPLGL

GGSSGSGGSGGGSGSGGGSGGSGGEVQLVESGGGLVQPGGSLRLS

CAASGSIFSINVMGWYRQAPGKQRELVAAISSGGSTNYADSVKGR

FTISRDNAKNTVYLQMNSLKPEDTAVYYCMYASSWYEDETDYWGQ

GTQVTVSS

SEQ ID NO: 72 comprises a variable heavy chain that binds to PD1, an Fc polypeptide comprising SLPLGL (SEQ ID NO: 2) cleavage substrate, and a VHH masking moiety from N- to C-terminus:

(SEQ ID NO: 72)

QVQLVQSGVEVKKPGASVKVSCKASGYTFTNYYMYWVRQAPGQGL

EWMGGINPSNGGTNFNEKFKNRVTLTTDSSTTTAYMELKSLQFDD

TAVYYCARRDYRFDMGFDYWGQGTTVTVSSASTKGPSVFPLAPSS

KSTSGGTAALGCLVKDYFPEPVTVSWNSGALTSGVHTFPAVLQSS

-continued

```
GLYSLSSVVTVPSSSLGTQTYICNVNHKPSNTKVDKKVEPKSCDK

THTCPPCPAPELLGGPSVFLFPPKPKDTLMISRTPEVTCVVVDVS

HEDPEVKFNWYVDGVEVHNAKTKPREEQYASTYRVVSVLTVLHQD

WLNGKEYKCKVSNKALPAPIEKTISKAKGQPREPQVCTLPPSRDE

LTKNQVSLSCAVKGFYPSDIAVEWESNGQPENNYKTTPPVLDSDG

SFFLVSKLTVDKSRWQQGNVFSCSVMHEALHNHYTQKSLSLPLGL

GGSSGSGGSGGGGSGSGGGEVQLVESGGGLVQPGGSLRLSCAASGS

IFSINVMGWYRQAPGKGRELVAAISSGGSTNYADSVKGRFTISRD

NAKNTVYLQMNSLKPEDTAVYYCAYASSYYEDETDYWGQGTQVTV

SS
```

SEQ ID NO: 73 comprises a variable heavy chain that binds to PD1, an Fc polypeptide comprising GGPLGL (SEQ ID NO: 3) cleavage substrate, and a VHH masking moiety from N- to C-terminus:

```
                                      (SEQ ID NO: 73)
QVQLVQSGVEVKKPGASVKVSCKASGYTFTNYYMYWVRQAPGQGL

EWMGGINPSNGGTNFNEKFKNRVTLTTDSSTTTAYMELKSLQFDD

TAVYYCARRDYRFDMGFDYWGQGTTVTVSSASTKGPSVFPLAPSS

KSTSGGTAALGCLVKDYFPEPVTVSWNSGALTSGVHTFPAVLQSS

GLYSLSSVVTVPSSSLGTQTYICNVNHKPSNTKVDKKVEPKSCDK

THTCPPCPAPELLGGPSVFLFPPKPKDTLMISRTPEVTCVVVDVS

HEDPEVKFNWYVDGVEVHNAKTKPREEQYASTYRVVSVLTVLHQD

WLNGKEYKCKVSNKALPAPIEKTISKAKGQPREPQVCTLPPSRDE

LTKNQVSLSCAVKGFYPSDIAVEWESNGQPENNYKTTPPVLDSDG

SFFLVSKLTVDKSRWQQGNVFSCSVMHEALHNHYTQKSLGGPLGL

GGSSGSGGSGGGGSGSGGGEVQLVESGGGLVQPGGSLRLSCAASGS

IFSINVMGWYRQAPGKGRELVAAISSGGSTNYADSVKGRFTISRD

NAKNTVYLQMNSLKPEDTAVYYCAYASSYYEDETDYWGQGTQVTV

SS
```

SEQ ID NO: 74 comprises a variable heavy chain that binds to PD1, an Fc polypeptide comprising GGPLGL (SEQ ID NO: 3) cleavage substrate, and a VHH masking moiety with alanine extension from N- to C-terminus:

```
                                      (SEQ ID NO: 74)
QVQLVQSGVEVKKPGASVKVSCKASGYTFTNYYMYWVRQAPGQGL

EWMGGINPSNGGTNFNEKFKNRVTLTTDSSTTTAYMELKSLQFDD

TAVYYCARRDYRFDMGFDYWGQGTTVTVSSASTKGPSVFPLAPSS

KSTSGGTAALGCLVKDYFPEPVTVSWNSGALTSGVHTFPAVLQSS

GLYSLSSVVTVPSSSLGTQTYICNVNHKPSNTKVDKKVEPKSCDK

THTCPPCPAPELLGGPSVFLFPPKPKDTLMISRTPEVTCVVVDVS

HEDPEVKFNWYVDGVEVHNAKTKPREEQYASTYRVVSVLTVLHQD

WLNGKEYKCKVSNKALPAPIEKTISKAKGQPREPQVCTLPPSRDE

LTKNQVSLSCAVKGFYPSDIAVEWESNGQPENNYKTTPPVLDSDG
```

```
SFFLVSKLTVDKSRWQQGNVFSCSVMHEALHNHYTQKSLGGPLGL

GGSSGSGGSGGGGSGSGGGEVQLVESGGGLVQPGGSLRLSCAASGS

IFSINVMGWYRQAPGKQRELVAAISSGGSTNYADSVKGRFTISRD

NAKNTVYLQMNSLKPEDTAVYYCMYASSWYEDETDYWGQGTQVTV

SSAAA
```

SEQ ID NO: 75 comprises a variable heavy chain that binds to PD1, and an Fc polypeptide from N- to C-terminus:

```
                                      (SEQ ID NO: 75)
QVQLVQSGVEVKKPGASVKVSCKASGYTFTNYYMYWVRQAPGQGL

EWMGGINPSNGGTNFNEKFKNRVTLTTDSSTTTAYMELKSLQFDD

TAVYYCARRDYRFDMGFDYWGQGTTVTVSSASTKGPSVFPLAPSS

KSTSGGTAALGCLVKDYFPEPVTVSWNSGALTSGVHTFPAVLQSS

GLYSLSSVVTVPSSSLGTQTYICNVNHKPSNTKVDKKVEPKSCDK

THTCPPCPAPELLGGPSVFLFPPKPKDTLMISRTPEVTCVVVDVS

HEDPEVKFNWYVDGVEVHNAKTKPREEQYASTYRVVSVLTVLHQD

WLNGKEYKCKVSNKALPAPIEKTISKAKGQPREPQVCTLPPSRDE

LTKNQVSLSCAVKGFYPSDIAVEWESNGQPENNYKTTPPVLDSDG

SFFLVSKLTVDKSRWQQGNVFSCSVMHEALHNHYTQKSLSLSPG
```

In some embodiments, a masked cytokine comprises a first polypeptide comprising an amino acid sequence of SEQ ID NO: 64, a second polypeptide comprising an amino acid sequence of SEQ ID NO: 66, and a third polypeptide comprising an amino acid sequence of SEQ ID NO: 50.

In some embodiments, a masked cytokine comprises a first polypeptide comprising an amino acid sequence of SEQ ID NO: 65, a second polypeptide comprising an amino acid sequence of SEQ ID NO: 66, and a third polypeptide comprising an amino acid sequence of SEQ ID NO: 50.

In some embodiments, a masked cytokine comprises a first polypeptide comprising an amino acid sequence of SEQ ID NO: 63, a second polypeptide comprising an amino acid sequence of SEQ ID NO: 66, and a third polypeptide comprising an amino acid sequence of SEQ ID NO: 50.

In some embodiments, a masked cytokine comprises a first polypeptide comprising an amino acid sequence of SEQ ID NO: 65, a second polypeptide comprising an amino acid sequence of SEQ ID NO: 68, and a third polypeptide comprising an amino acid sequence of SEQ ID NO: 50.

In some embodiments, a masked cytokine comprises a first polypeptide comprising an amino acid sequence of SEQ ID NO: 65, a second polypeptide comprising an amino acid sequence of SEQ ID NO: 69, and a third polypeptide comprising an amino acid sequence of SEQ ID NO: 50.

In some embodiments, a masked cytokine comprises a first polypeptide comprising an amino acid sequence of SEQ ID NO: 65, a second polypeptide comprising an amino acid sequence of SEQ ID NO: 70, and a third polypeptide comprising an amino acid sequence of SEQ ID NO: 50.

In some embodiments, a masked cytokine comprises a first polypeptide comprising an amino acid sequence of SEQ ID NO: 65, a second polypeptide comprising an amino acid sequence of SEQ ID NO: 67, and a third polypeptide comprising an amino acid sequence of SEQ ID NO: 50.

In some embodiments, a masked cytokine comprises a first polypeptide comprising an amino acid sequence of SEQ ID NO: 65, a second polypeptide comprising an amino acid sequence of SEQ ID NO: 71, and a third polypeptide comprising an amino acid sequence of SEQ ID NO: 50.

In some embodiments, a masked cytokine comprises a first polypeptide comprising an amino acid sequence of SEQ ID NO: 63, a second polypeptide comprising an amino acid sequence of SEQ ID NO: 72, and a third polypeptide comprising an amino acid sequence of SEQ ID NO: 50.

In some embodiments, a masked cytokine comprises a first polypeptide comprising an amino acid sequence of SEQ ID NO: 63, a second polypeptide comprising an amino acid sequence of SEQ ID NO: 73, and a third polypeptide comprising an amino acid sequence of SEQ ID NO: 50.

In some embodiments, a masked cytokine comprises a first polypeptide comprising an amino acid sequence of SEQ ID NO: 63, a second polypeptide comprising an amino acid sequence of SEQ ID NO: 67, and a third polypeptide comprising an amino acid sequence of SEQ ID NO: 50.

In some embodiments, a masked cytokine comprises a first polypeptide comprising an amino acid sequence of SEQ ID NO: 65, a second polypeptide comprising an amino acid sequence of SEQ ID NO: 74, and a third polypeptide comprising an amino acid sequence of SEQ ID NO: 50.

EXAMPLES

While certain compounds, compositions and methods of the present invention have been described with specificity in accordance with certain embodiments, the following examples serve only to illustrate the compounds of the invention and are not intended to limit the same.

Example 1. IL-2 Cytokines in Masked Cytokine Constructs are Effectively Masked by VHH Masking Moieties This example illustrates that masked IL-2 cytokines with a cleavable Fc domain are effectively masked by the VHH masking moieties and can be successfully cleaved by tumor-specific protease, restoring the potency of the IL-2 cytokine.

Various masked and targeted IL-2 cytokines shown in Table 1 are prepared. Each masked and targeted cytokine is made up of three chains: chain 1 containing PD-1 targeting VH+ uncleavable Fc domain+IL-2 cytokine; chain 2 containing PD-1 targeting VH+cleavable Fc domain+VHH masking moiety, and chain 3 containing PD-1 targeting VL. An exemplary construct is illustrated in FIG. 1. Recombinant human IL-2 (rhIL-2) and Control UCMs, which do not comprise a masking moiety, are used as controls.

TABLE 1

| | | | | | | | |
|---|---|---|---|---|---|---|---|
| Exemplary Targeted and Masked IL-2 Cytokines with Cleavable Fc Domain | | | | | | | |
| Construct | IL-2 | Masking Moiety | Targeting Moiety | Cleavable substrate in Fc | Chain 1 SEQ ID NO | Chain 2 SEQ ID NO | Chain 3 SEQ ID NO |
| UCM1 | C125A (SEQ ID NO: 11) | VHH (SEQ ID NO: 19) | PD-1 targeting moiety | PLGL (SEQ ID NO: 1) | 64 | 66 | 50 |
| UCM2 | R38A, F42A, Y45A, E62A, C125A (SEQ ID NO: 12) | VHH (SEQ ID NO: 19) | PD-1 targeting moiety | PLGL (SEQ ID NO: 1) | 65 | 66 | 50 |
| UCM3 | F42E, C125A (SEQ ID NO: 13) | VHH (SEQ ID NO: 19) | PD-1 targeting moiety | PLGL (SEQ ID NO: 1) | 63 | 66 | 50 |
| UCM4 | R38A, F42A, Y45A, E62A, C125A (SEQ ID NO: 12) | VHH (SEQ ID NO: 19) | PD-1 targeting moiety | MPY (SEQ ID NO: 4) | 65 | 68 | 50 |
| UCM5 | R38A, F42A, Y45A, E62A, C125A (SEQ ID NO: 12) | VHH (SEQ ID NO: 19) | PD-1 targeting moiety | APAG (SEQ ID NO: 6) | 65 | 69 | 50 |
| UCM6 | R38A, F42A, Y45A, E62A, C125A (SEQ ID NO: 12) | VHH (SEQ ID NO: 19) | PD-1 targeting moiety | PAN (SEQ ID NO: 8) | 65 | 70 | 50 |
| UCM7 | R38A, F42A, Y45A, E62A, C125A (SEQ ID NO: 12) | VHH (SEQ ID NO: 19) | PD-1 targeting moiety | PLGL (SEQ ID NO: 1) | 65 | 67 | 50 |
| UCM8 | R38A, F42A, Y45A, E62A, C125A (SEQ ID NO: 12) | VHH (SEQ ID NO: 19) | PD-1 targeting moiety | PLGL (SEQ ID NO: 1) | 65 | 71 | 50 |
| UCM9 | F42E, C125A (SEQ ID NO: 13) | VHH (SEQ ID NO: 20) | PD-1 targeting moiety | PLGL (SEQ ID NO: 1) | 63 | 72 | 50 |

TABLE 1-continued

Exemplary Targeted and Masked IL-2 Cytokines with Cleavable Fc Domain

| Construct | IL-2 | Masking Moiety | Targeting Moiety | Cleavable substrate in Fc | Chain 1 SEQ ID NO | Chain 2 SEQ ID NO | Chain 3 SEQ ID NO |
|---|---|---|---|---|---|---|---|
| UCM10 | F42E, C125A (SEQ ID NO: 13) | VHH (SEQ ID NO: 20) (SEQ ID NO: 13) | PD-1 targeting moiety | PLGL (SEQ ID NO: 1) | 63 | 73 | 50 |
| UCM11 | F42E, C125A (SEQ ID NO: 13) | VHH (SEQ ID NO: 19) | PD-1 targeting moiety | PLGL (SEQ ID NO: 1) | 63 | 67 | 50 |
| UCM12 | F42E, C125A (SEQ ID NO: 13) | VHH (SEQ ID NO: 21) | PD-1 targeting moiety | PLGL (SEQ ID NO: 1) | 63 | 74 | 50 |
| Control UCM1 | F42E, C125A (SEQ ID NO: 13) | N/A | PD-1 targeting moiety | N/A | 63 | 75 | 50 |
| Control UCM2 | C125A (SEQ ID NO: 11) | N/A | PD-1 targeting moiety | N/A | 64 | 75 | 50 |
| Control UCM3 | R38A, F42A, Y45A, E62A, C125A (SEQ ID NO: 12) | N/A | PD-1 targeting moiety | N/A | 65 | 75 | 50 |

Figure 2A:
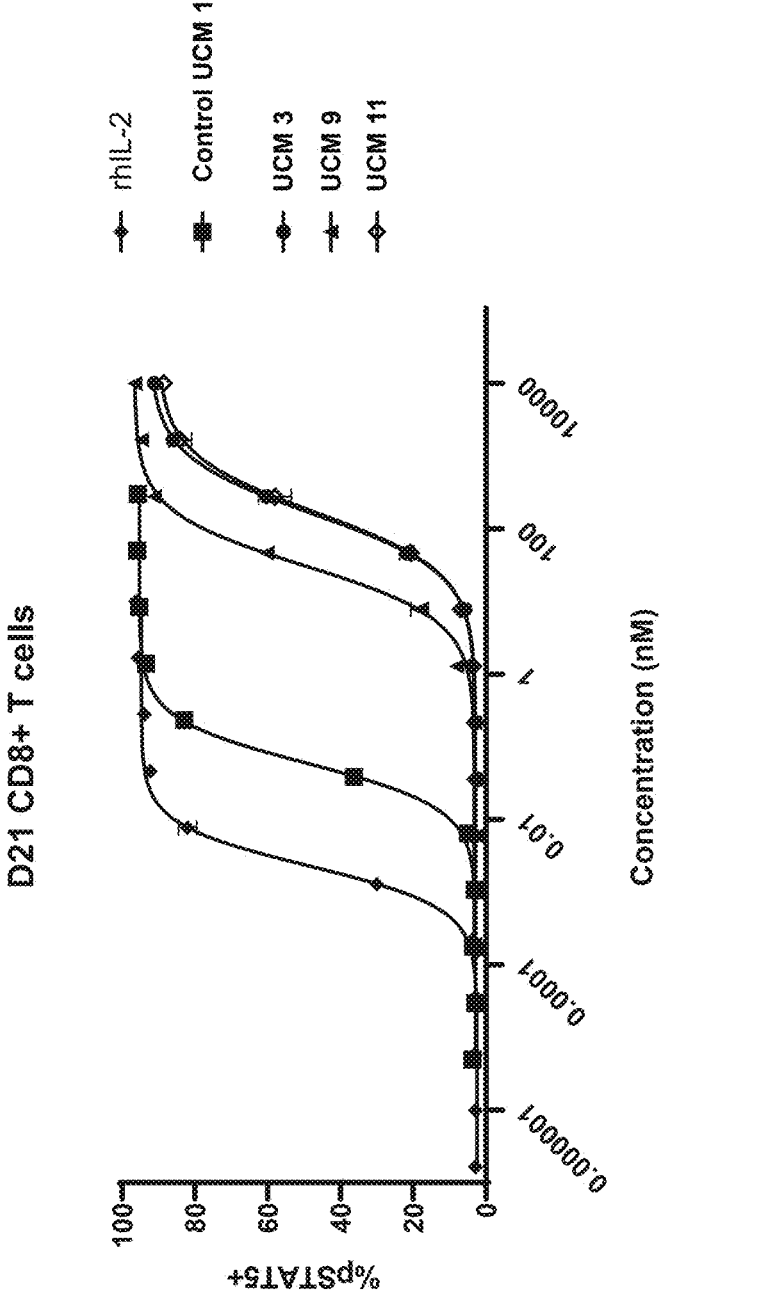
FIGS. 2A and 2B are exemplary graphs illustrating percentage of STAT5 phosphorylation which indicates the effectiveness of masking of IL-2 cytokines by the VHH masking moieties.
Figure 2B:
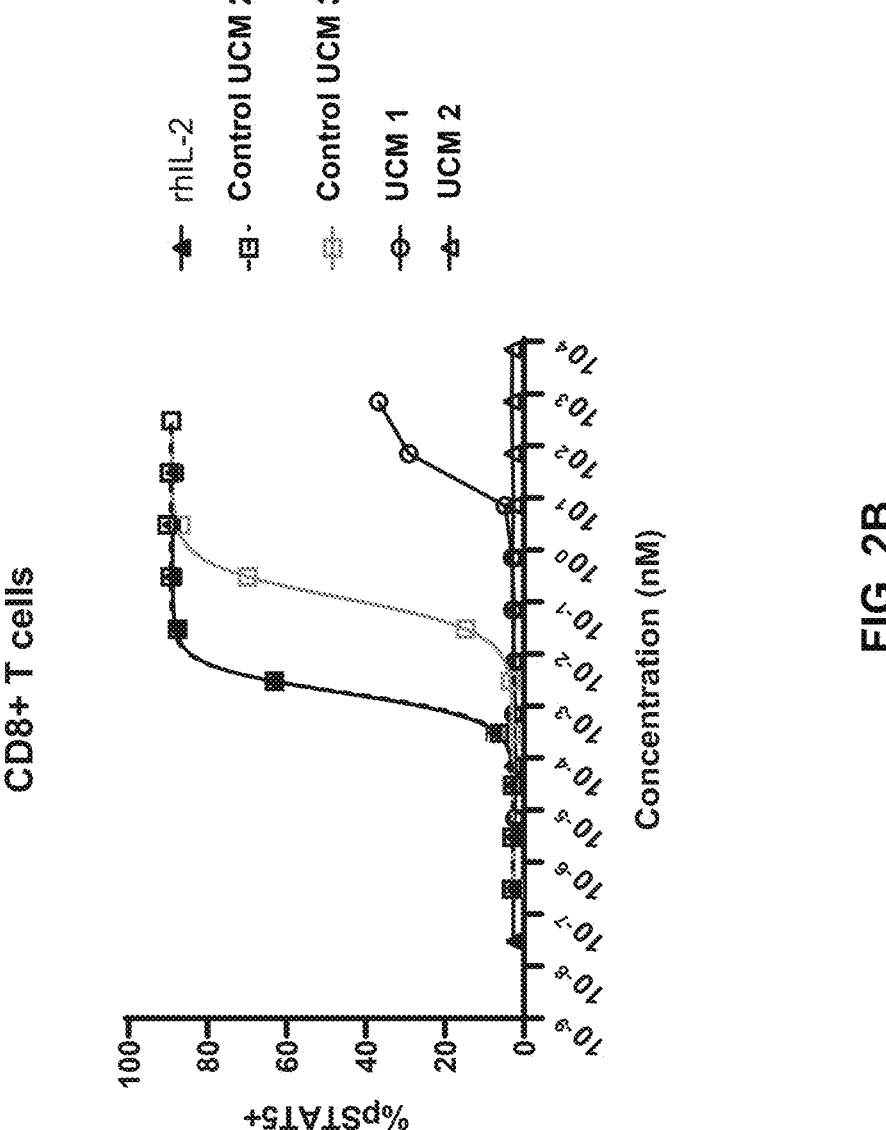

Percentage of STAT5 phosphorylation was measured to determine the effectiveness of masking of IL-2 cytokines by the VHH masking moieties. Briefly, primary human peripheral blood mononuclear cells (PBMCs) were preactivated to upregulate PD-1 expression. Preactivated PBMCs were incubated with varying doses of exemplary constructs in Table 1 for 12 minutes followed by evaluation for STAT5 phosphorylation. Constructs with VHH masking moieties exhibited minimal activity on hPBMCs while unmasked control constructs exhibited potent signaling on CD8+ T cells. Results for UCM Control 1, UCM3, UCM9, and UCM11 are shown in FIG. 2A, and results for UCM Controls 2 and 3, UCM1, and UCM2 are shown in FIG. 2B.

Example 2. Ex Vivo Cleavage of Masked IL-2 Cytokines with Cleavable Fc Domains

This example illustrates that masked IL-2 cytokines comprising cleavable Fc domains can be cleaved by human tumors but not by plasma.

Frozen cells extracted from fresh tumor tissues (X-FACT assay) and human plasma, were used for ex vivo cleavage of masked cytokines with cleavable Fc domains. Cells from five different indications: Melanoma, HNC (Head and Neck cancer), Lung cancer, Colon cancer, Renal cell carcinoma (RCC) were used for the cleavage assay. UCM2, UCM3, UCM4, UCM5, UCM6, UCM7, UCM8, UCM9, and UCM 11 shown in Table 1, and non-cleavable control molecules were incubated with frozen tumor cells, or in human plasma derived from healthy donors and patients with Melanoma, HNC, Lung tumor, colon tumors, and RCC.

Figure 3A:
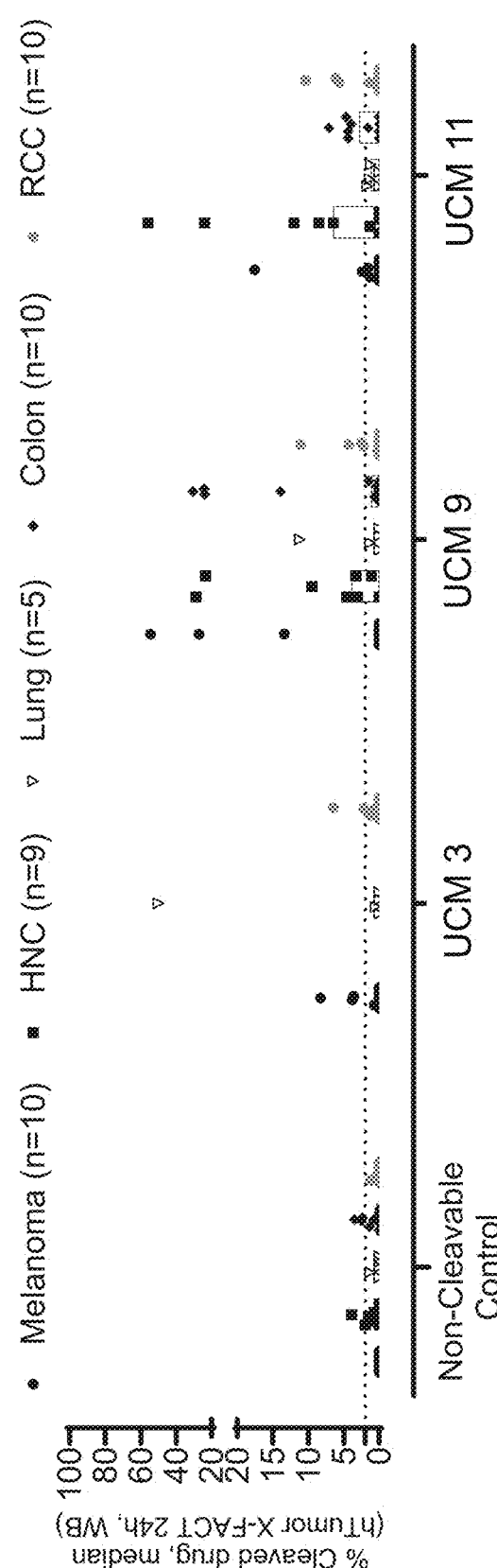
FIG. 3A shows % of cleaved masked IL-2 cytokines (UCM3, UCM9, and UCM11) by human tumors ex vivo.
Figure 3B:
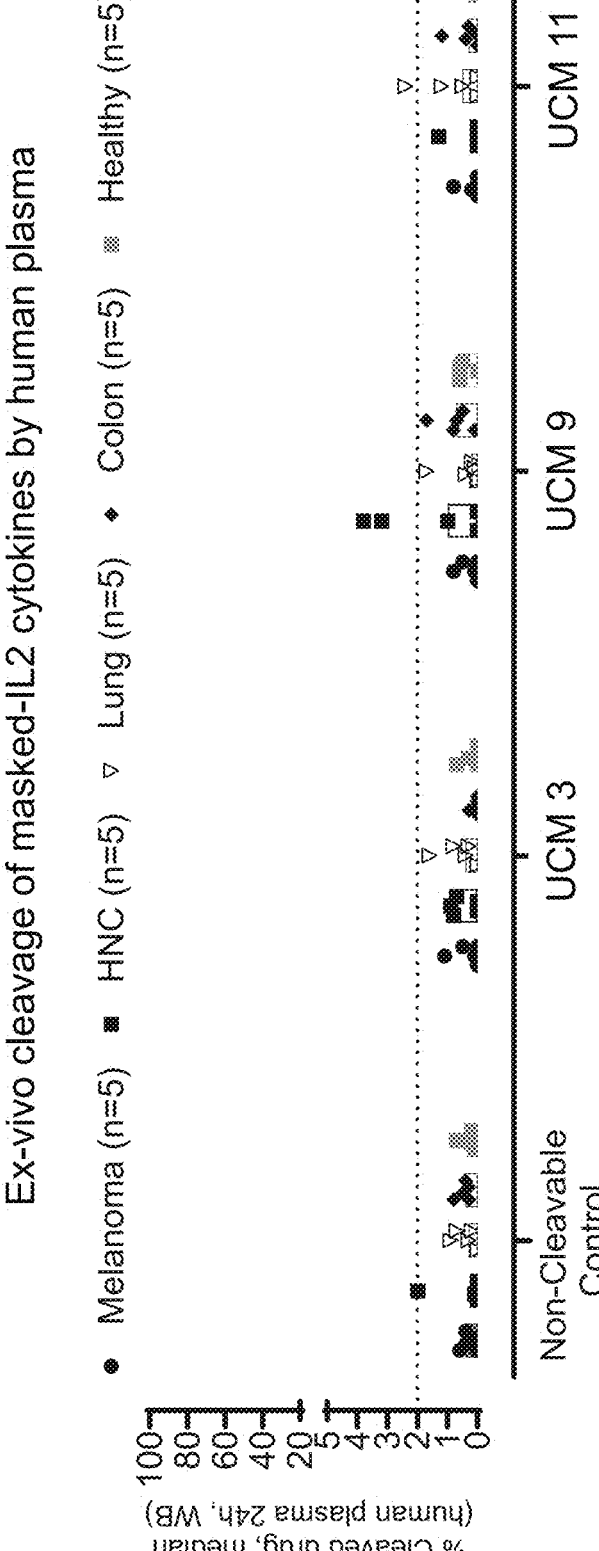
FIG. 3B shows % of cleaved masked IL-2 cytokines (UCM3, UCM9, and UCM11) by human plasma.
Figure 3C:
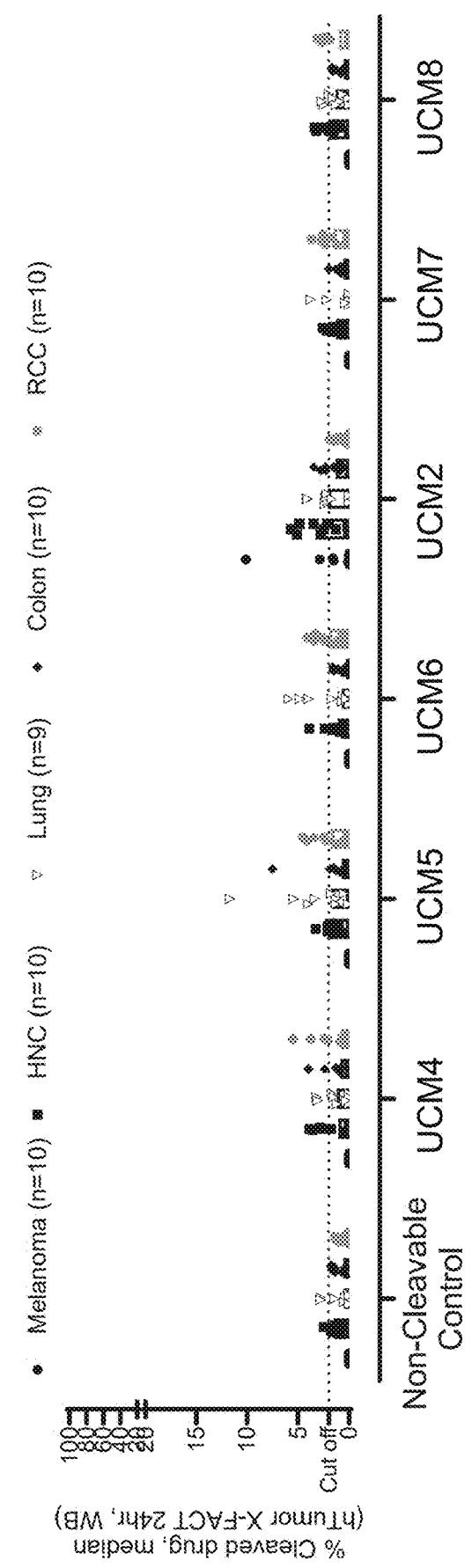
FIG. 3C shows % of cleaved masked IL-2 cytokines (UCM4, UCM5, UCM6, UCM2, UCM7, and UCM8) by human tumors ex vivo.
Figure 3D:
FIG. 3D shows % of cleaved masked IL-2 cytokines (UCM4, UCM5, UCM6, UCM2, UCM7, and UCM8) by human plasma.

The cleavage results were analysed by western blotting. The results for UCM3, UCM9, and UCM9 are shown in FIG. 3A and FIG. 3B, and the results for UCM2, UCM3, UCM4, UCM5, UCM6, UCM7, and UCM8 are shown in FIG. 3C and FIG. 3D. All masked IL-2 cytokines were cleaved by human tumors ex vivo, as shown in FIG. 3A and FIG. 3C. On the other hand, the masked cytokines were not cleaved by human plasma, indicating specific cleavage by tumors as desired (FIG. 3B and FIG. 3D).

Figure 3E:
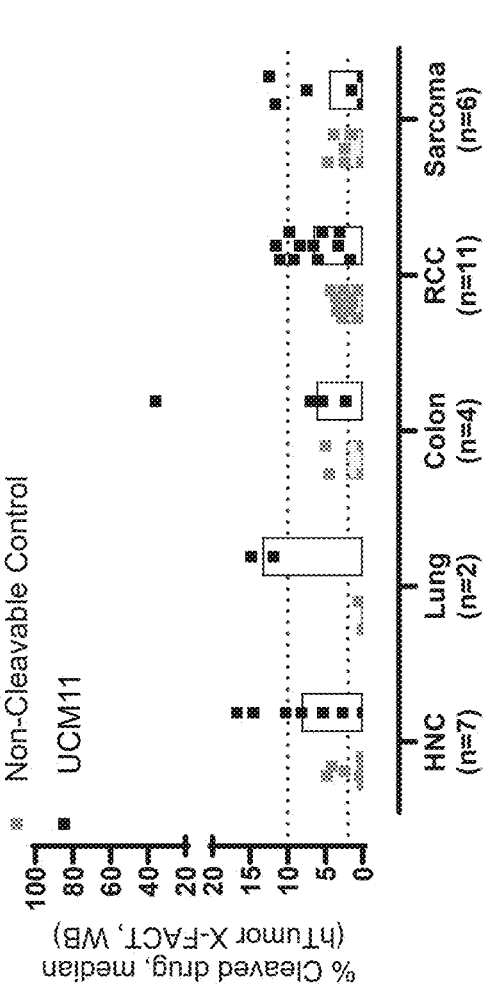
FIG. 3E shows % of cleaved masked IL-2 cytokine UCM11 by fresh human tumor cells ex vivo.

Next, fresh tumor cells from five different indications, HNC (Head and Neck cancer), Lung cancer, Colon cancer, Renal cell carcinoma (RCC), and sarcoma were used for the cleavage assay. UCM11 was tested and compared to non-cleavable control. As shown in FIG. 3E, UCM11 had significantly higher % cleaved as compared to the non-cleavable control. Non-cleavable control had less than about 3% cleavage, whereas UCM had at least greater than 4% and up to 13.4%, indicative of significant cleavage.

Figure 3F:
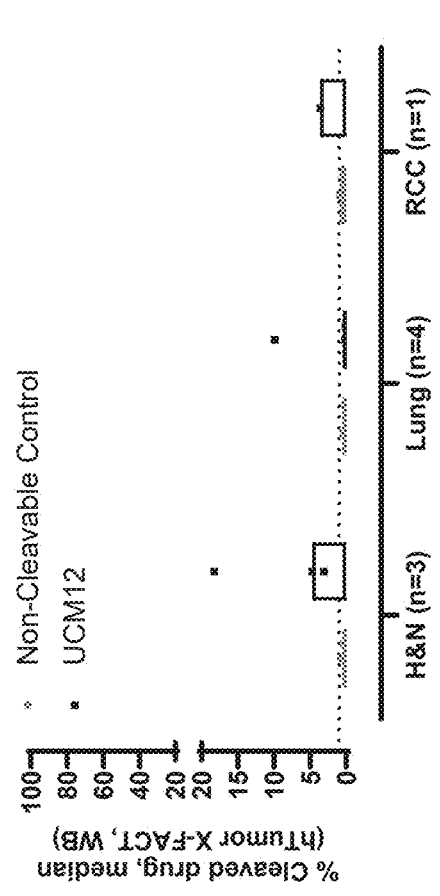
FIG. 3F shows % of cleaved masked IL-2 cytokine UCM12 by fresh human tumor cells ex vivo.

Next, fresh tumor cells from three different indications, HNC (Head and Neck cancer), Lung cancer, and Renal cell carcinoma (RCC) were used for the cleavage assay. UCM12 was tested and compared to non-cleavable control. As shown in FIG. 3F, UCM12 had significantly higher % cleavage as compared to the non-cleavable control. Non-cleavable control had less than 1% cleavage, whereas UCM12 had up to 4.7% cleavage, consistent with tumor mediated cleavage of UCM12.

Example 3. In Vivo Efficacy of Masked Cytokines with Cleavable Fc Domains

This example illustrates the targeted and masked IL-2 cytokines containing a cleavable Fc domain are efficacious in vivo. In this particular study, human PD-1 transgenic mice bearing murine tumors were used.

In one study, C57BL/6-B-hPD1 mice were implanted subcutaneously with MC38 tumor cells and received two intravenous injections of 8 mg/kg UCM3, UCM9 or UCM11 (N=8), and 0.75 mg/kg of Control UCM1 (N=8), or vehicle (N=8). Tumor and body weight measurements were taken two or three times a week.

Figure 4A:
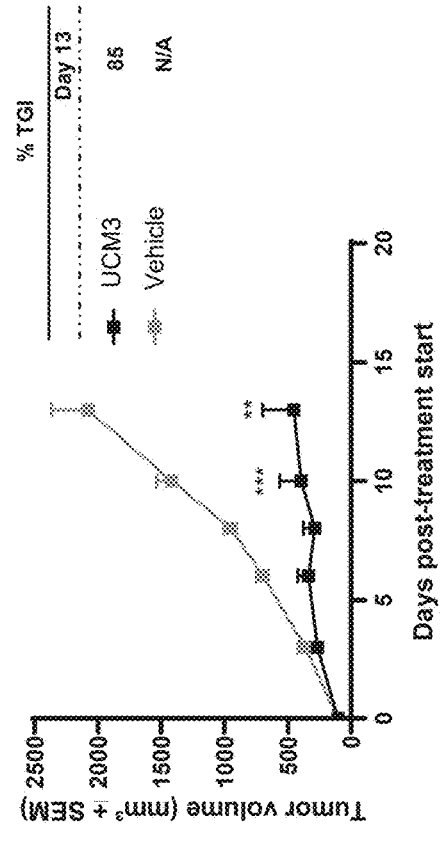
FIG. 4A is a series of exemplary graphs illustrating changes in tumor volume over time after treatment with targeted IL-2 cytokines of the present invention (UCM9, UCM11, and UCM3). % TGI represents tumor growth inhibition.
Figure 4A:
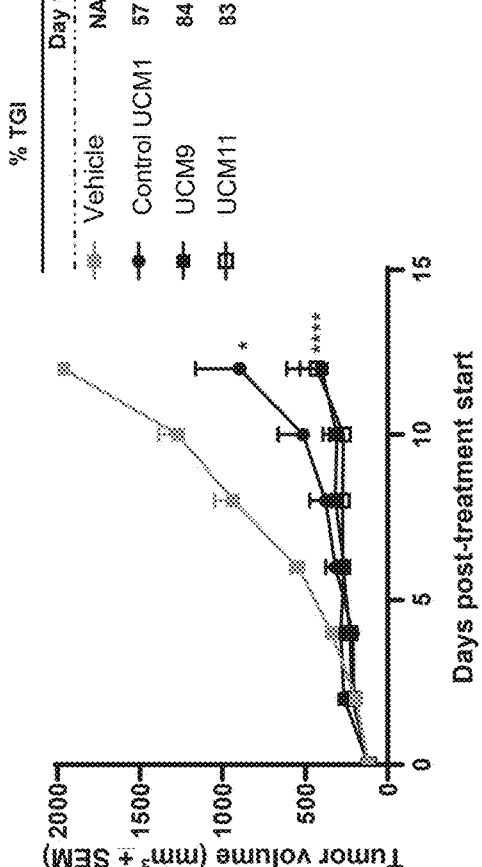
Figure 4B:
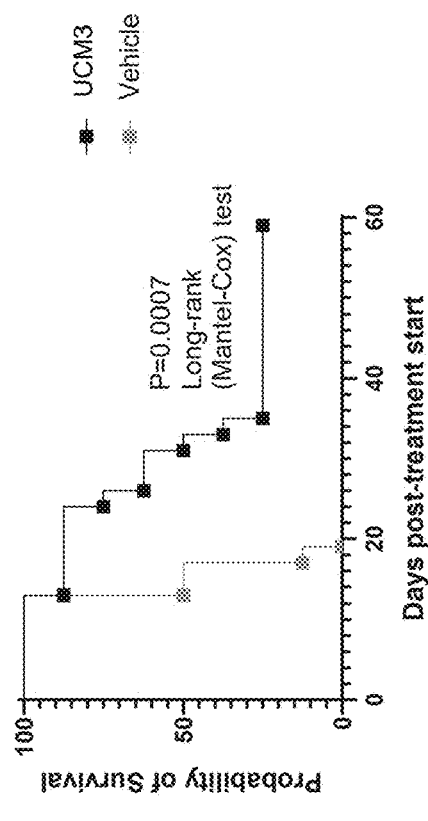
FIG. 4B is a series of exemplary graphs illustrating overall survival following treatment with targeted IL-2 cytokines of the present invention (UCM9, UCM11, and UCM3).
Figure 4B:
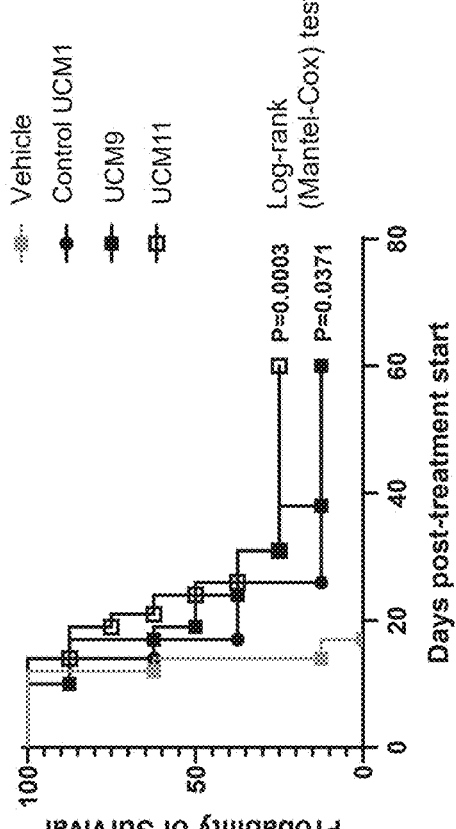

The results for are shown in FIG. 4A and FIG. 4B. Overall, the data shows that the masking moiety in the targeted IL-2 cytokine with an engineered cleavable Fc domain is effectively cleaved in vivo, activating the IL-2 activity. The activated targeted cytokine was effective in inhibiting tumor growth as compared to vehicle (FIG. 4A). Additionally, overall survival probability of the treated mice increased (FIG. 4B).

Figure 4C:
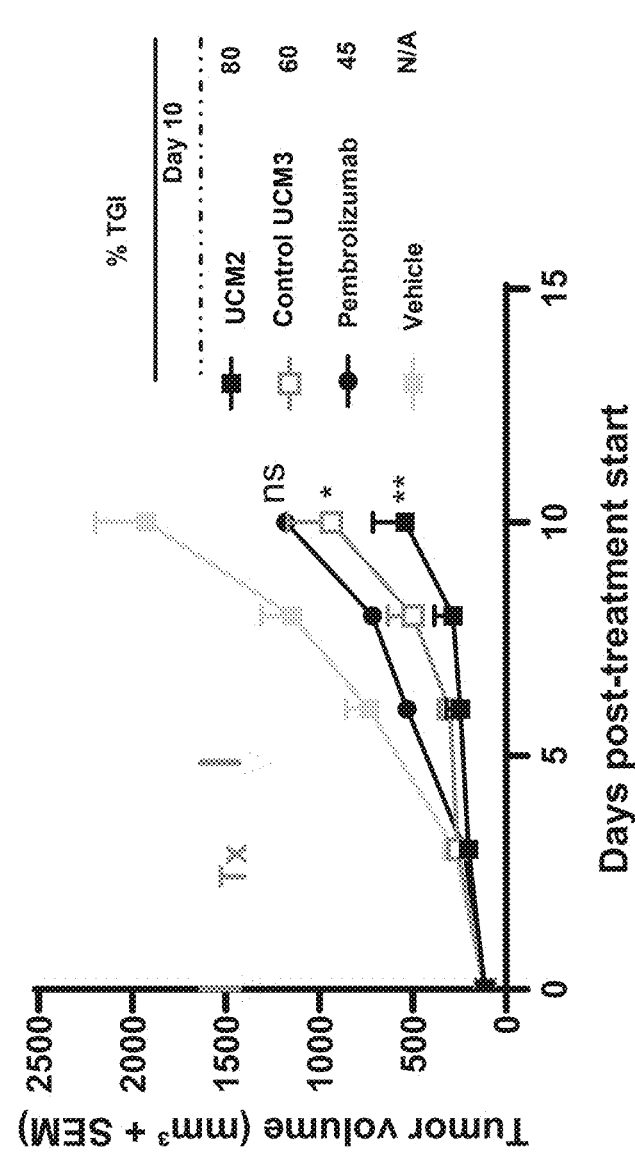
FIG. 4C is an exemplary graph illustrating changes in tumor volume over time after treatment with targeted IL-2 cytokines of the present invention (UCM2). % TGI represents tumor growth inhibition.
Figure 4D:
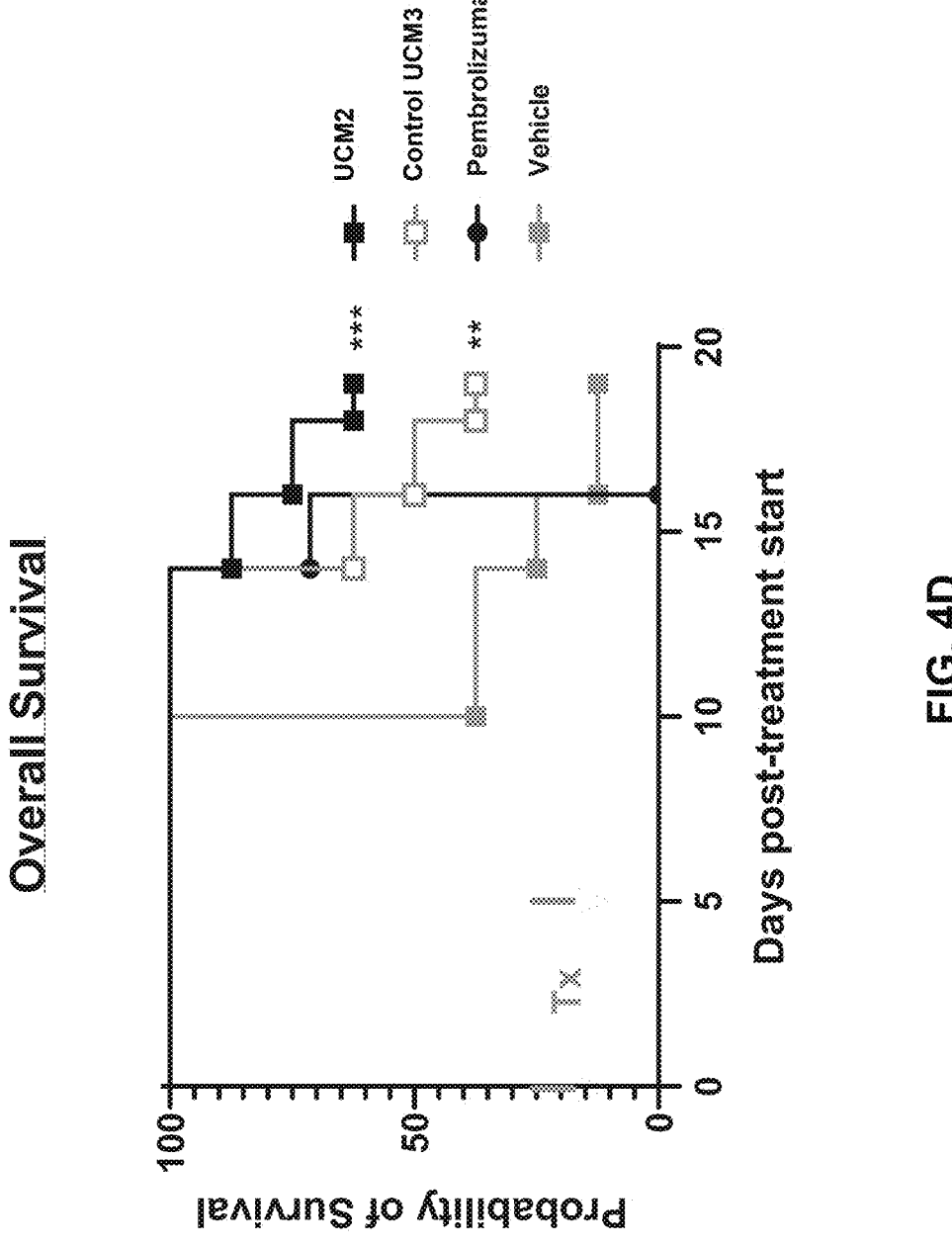
FIG. 4D is an exemplary graph illustrating overall survival following treatment with targeted IL-2 cytokines of the present invention (UCM2).

In another study, the in vivo efficacy of UCM2 was also assessed by the same methods explained above. The Control UCM3 and a reference PD-1 antibody were used as controls. Overall, the data shows that the masking moiety in the targeted IL-2 cytokine with an engineered cleavable Fc domain is effectively cleaved in vivo, activating the IL-2 activity. The activated targeted cytokine was effective in inhibiting tumor growth as compared to vehicle (FIG. 4C). Additionally, overall survival probability of the treated mice increased (FIG. 4D).

In another study, the in vivo efficacy of UCM12 was also assessed by the same methods explained herein in the bladder murine model MB49. In particular, C57BL/6-hPD1 mice were implanted subcutaneously with MB49 tumor cells and received two intravenous injections of 10 or 3 mg/kg UCM12 (N=9) or Vehicle (N=9). Equal molar dose of Pembrolizumab (N=9) was also as a control. Tumor and body weights measurements were taken two or three times a week.

Figure 4E:
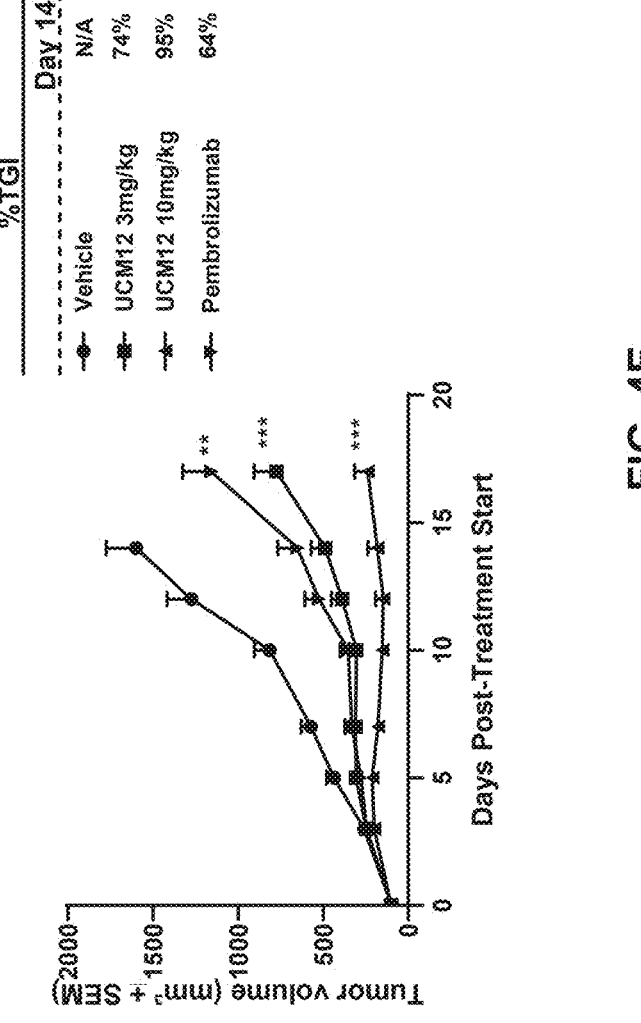
FIG. 4E is an exemplary graph illustrating changes in tumor volume over time after treatment with targeted IL-2 cytokines of the present invention (UCM12). % TGI represents tumor growth inhibition.
Figure 4F:
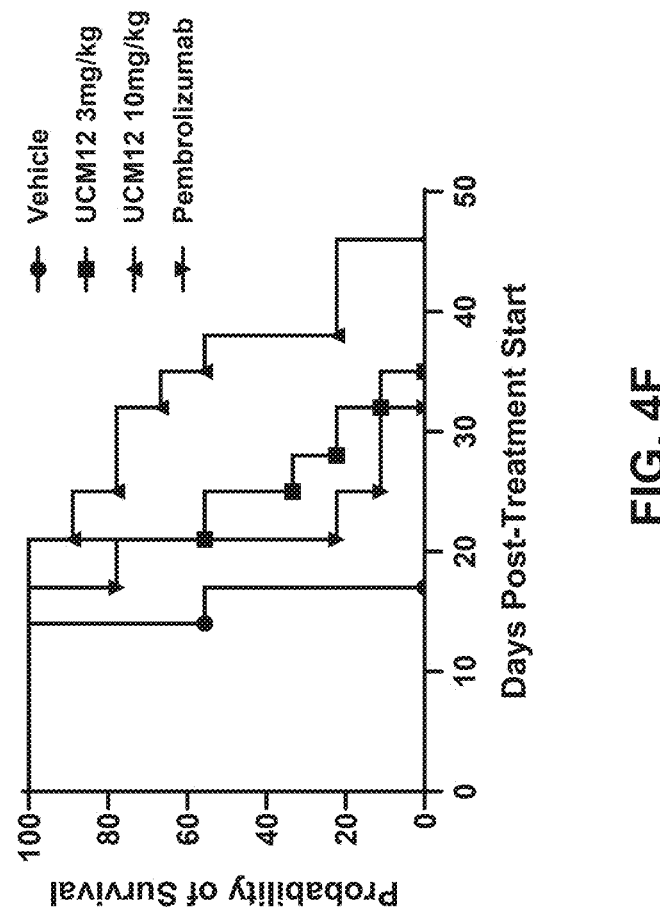
FIG. 4F is an exemplary graph illustrating overall survival following treatment with targeted IL-2 cytokines of the present invention (UCM12).

The results for UCM12 are shown in FIG. 4E and FIG. 4F. Overall, the data shows that the masking moiety in the targeted IL-2 cytokine with an engineered cleavable Fc domain is effectively cleaved in vivo, activating the IL-2 activity. The activated targeted cytokine was effective in inhibiting tumor growth as compared to vehicle (FIG. 4E). Additionally, overall survival probability of the treated mice increased (FIG. 4F).

Example 4. Validation of In Vivo Efficacy of Masked Cytokines with Cleavable Fc Domains This example validates that the targeted and masked IL-2 cytokines containing a cleavable Fc domain are efficacious in vivo. In this study, human PD-1 transgenic mice bearing murine tumors were used.

C57BL/6-hPD1 mice were implanted subcutaneously with MC38 tumor cells and received two intravenous injection of 7.5 mg/kg UCM4, UCM6, UCM7 or UCM8 (N=8) or vehicle (N=8). Tumor and body weight measurements were taken two or three times a week.

Figure 5A:
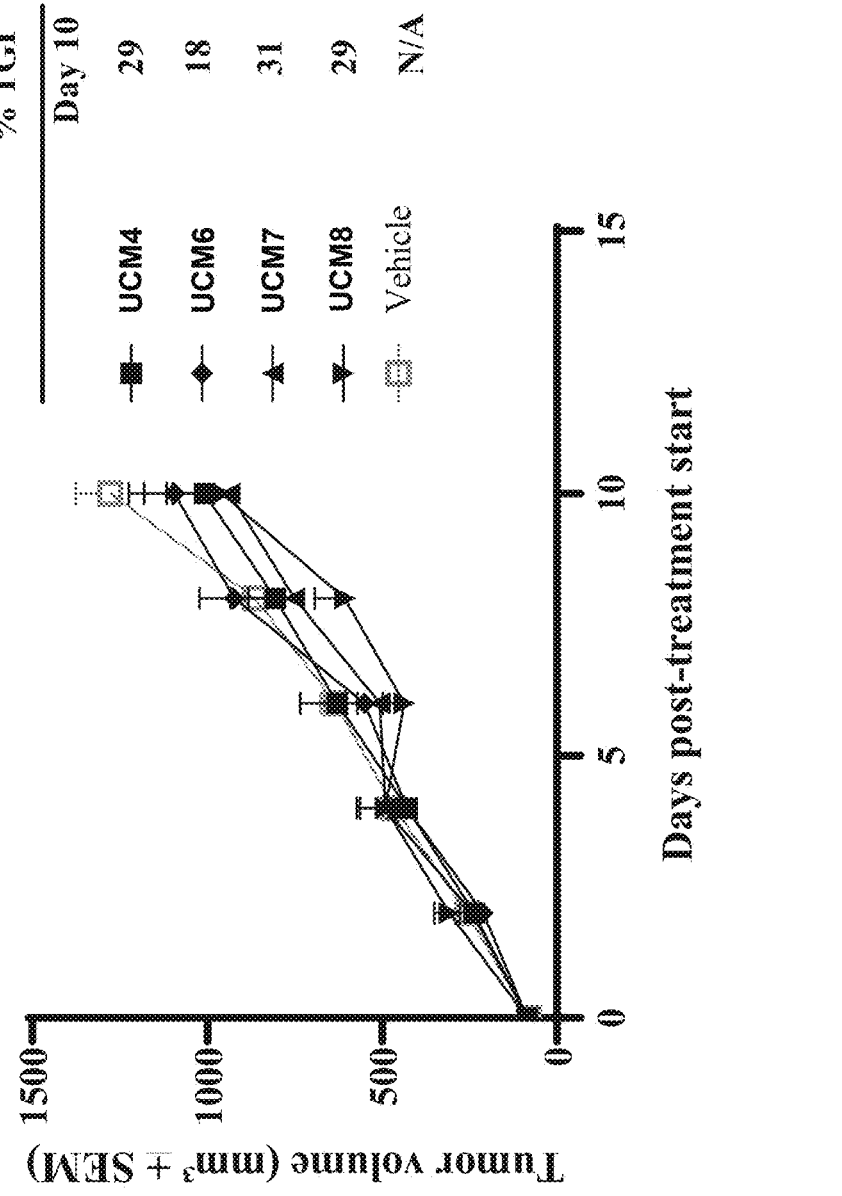
FIG. 5A is an exemplary graph illustrating changes in tumor volume over time after treatment with targeted IL-2 cytokines of the present invention (UCM4, UCM6, UCM7, and UCM8). % TGI represents tumor growth inhibition.
Figure 5B:
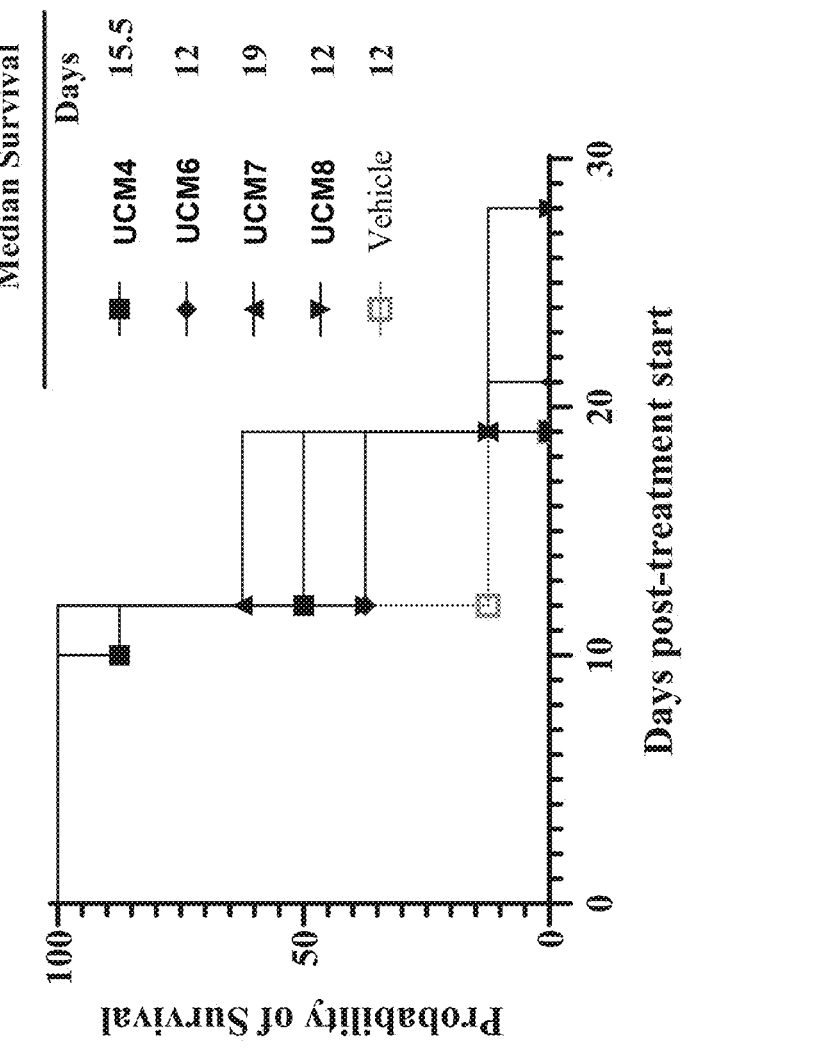
FIG. 5B is an exemplary graph illustrating overall survival following treatment with targeted IL-2 cytokines of the present invention (UCM4, UCM6, UCM7, and UCM8).

The results for are shown in FIG. 5A and FIG. 5B. Overall, the data shows that the masking moiety in the targeted IL-2 cytokine with an engineered cleavable Fc domain is effectively cleaved in vivo, activating the IL-2 activity. The activated targeted cytokine was effective in inhibiting tumor growth as compared to vehicle (FIG. 5A). Additionally, overall survival probability of the mice treated with UCM4 or UCM7 increased (FIG. 5B).

Example 5. IL-2 Cytokines in Masked Cytokine Constructs are Effectively Masked by VHH Masking Moieties and Activated by Tumor-Associated Protease Masked cytokines with a cleavable Fc domain were tested for in vitro protease cleavage by tumor-associated proteases. In this particular study, UCM12 was cleaved by MMP9. Recombinant human protease MMP-9 was activated by diluting to 0.22 mg/mL in MMP buffer (150 mM NaCl; 50 mM Tris, pH 7.5; 10 mM CaCl2) and incubating with equal volume of 1 mM 4-aminophenylmercuric acetate at 37° C.

for 24 hours. Subsequently, each sample was diluted to 1 uM in MMP buffer and two aliquots were prepared: 100 uL (cleaved) and 300 uL (non-cleaved). Pre-activated 25 ng MMP9 was added to the cleaved tube. The non-cleaved tube had the same volume of buffer added. Samples were incubated at 37° C. for 18 hours. Cleavage was confirmed by performing SDS-PAGE under reducing and denaturing conditions.

Figure 6A:
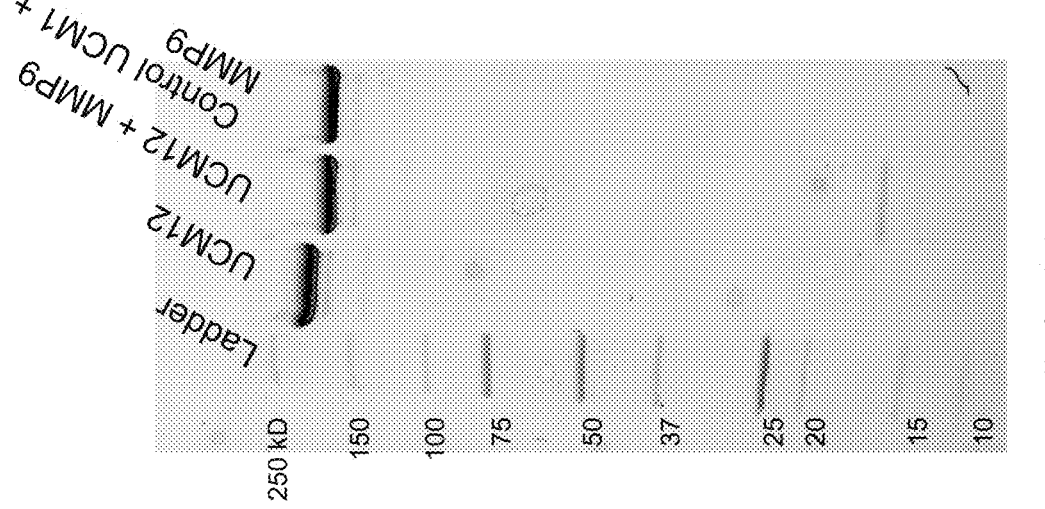
FIG. 6A is an exemplary SDS-PAGE image, showing the cleavage of masked cytokines UCM 12 by MMP9.

An SDS-PAGE image, shown in FIG. 6A, indicates that UCM12 is effectively cleaved by MMP9, resulting in the same control band as the control UCM1 (unmasked control).

In addition to cleavage by MMP9, the masked cytokines with a cleavable Fc domain were tested for in vitro protease cleavage by various other tumor-associated proteases. To measure the catalytic efficiency of UCM12 cleavage by human proteases, UCM12 was incubated with Matrix Metalloproteinase 1 (MMP1), MMP2, MMP8, MMP9 or cathepsin L. Aliquots were taken over the course of the reaction and analyzed by capillary electrophoresis-sodium dodecyl sulfate. The amount of UCM12 cleavage was determined using LabChip GX Reviewer software. The data from FIGS. 6C and 6D as well as Table 5 demonstrate that UCM12 is efficiently cleaved and activated by multiple proteases.

TABLE 5

| Catalytic Efficiency of UCM12 Cleavage by Tested Proteases | |
| --- | --- |
| Protease | $k_{cat}/K_m$ ($M^{-1}s^{-1}$) |
| MMP1 | $2.3 \times 10^2$ |
| MMP2 | $1.9 \times 10^3$ |
| MMP8 | $8.1 \times 10^2$ |
| MMP9 | $7.9 \times 10^3$ |
| Cathepsin L | $1.4 \times 10^4$ |

Next, the percentage of STAT5 phosphorylation was measured to determine the effectiveness of masking of IL-2 cytokines by the VHH masking moieties, and activation by tumor-associated cleavage.

Matrix Metalloproteinase-9 (MMP9) was activated overnight at 1.3 uM using 1 mM p-aminophenylmercuric acetate in MMP Buffer (50 mM Tris, 10 mM CaCl$_2$), 150 mM NaCl, pH 7.5). The next day, test articles (2 uM) were cleaved overnight at 37° C. in MMP buffer with shaking using 25 nM preactivated MMP9. Cleavage was confirmed using SDS page.

pSTAT5 activity (STAT5 phosphorylation) was measured on human peripheral blood mononuclear cells (PBMCs).

Briefly, 96-well flat-bottom plates were coated with 1 ug/mL anti-CD3 (clone: OKT3) in phosphate buffered saline (PBS) for 1 hr at 37° C. in an incubator. Meanwhile, cryopreserved hPBMCs were thawed in a 37° C. water-bath and then transferred to complete media (Roswell Park Memorial Institute 1640 medium [RPMI-1640], 10% fetal bovine serum [FBS], 50 U/mL penicillin, 50 µg/mL streptomycin, 2 mM L-glutamine, 1 uM each of non-essential amino acids (glycine, alanine, asparagine, aspartic acid, glutamic acid, proline, and serine), 10 mM HEPES (N-2-hydroxyethylpierazine-N-2-ethane sulfonic acid), 1 mM sodium pyruvate, 55 µM β mercaptoethanol, 10 µg/mL gentamycin). hPBMCs were then counted, centrifuged at 450 g ×4 min, supernatant was discarded, and cells were resuspended at 2×10$^6$cells/mL in complete media. CD3-coated 96 well plates were washed 3× with PBS. Anti-CD28 antibody (clone: CD28.2) was added to the hPBMCs at a final concentration of 1 ug/ml and 200 ul of the hPBMC cell suspension was added to each well in the CD3-coated 96 well plates. Plates were incubated at 37° C. for two days. Subsequently, hPBMCs were collected and counted. hPBMCs were washed twice with complete media then resuspended at $2\times10^6$/mL. hPBMCs were plated again in 96-well round bottom plates with 100 ul per well and rested overnight at 37° C.

The next day, serial dilutions of test articles were diluted to two-fold their final concentration in complete media. The plates were removed from the incubator and 50 ul was carefully removed from each well. An equal volume (50 ul) of construct was added to the 50 ul of cells and incubated at 37° C. After 12 minutes, paraformaldehyde was added directly to the cells to a final concentration of 2.7% and then incubated at 37° C. for 15 minutes.

Subsequently, cells were washed once with 200 ul of fluorescent activated cell sorting (FACS) buffer (1×PBS, 2% FBS). Cells were resuspended in 200 ul of Perm III Buffer (BD Biosciences) and incubated on ice for 30 minutes. Cells were washed three times with 200 ul FACS buffer and then resuspended in 100 µl of antibody mix in FACS buffer. Cells were incubated in the dark on ice for 30 min. An additional 150 ul of FACS buffer was added to each well and spun at 450g×4 min. The plates were washed once more with 200 ul FACS buffer. Stained hPBMCs were resuspended in 150 ul of FACS and run on a BD Fortessa cytometer.

Figure 6B:
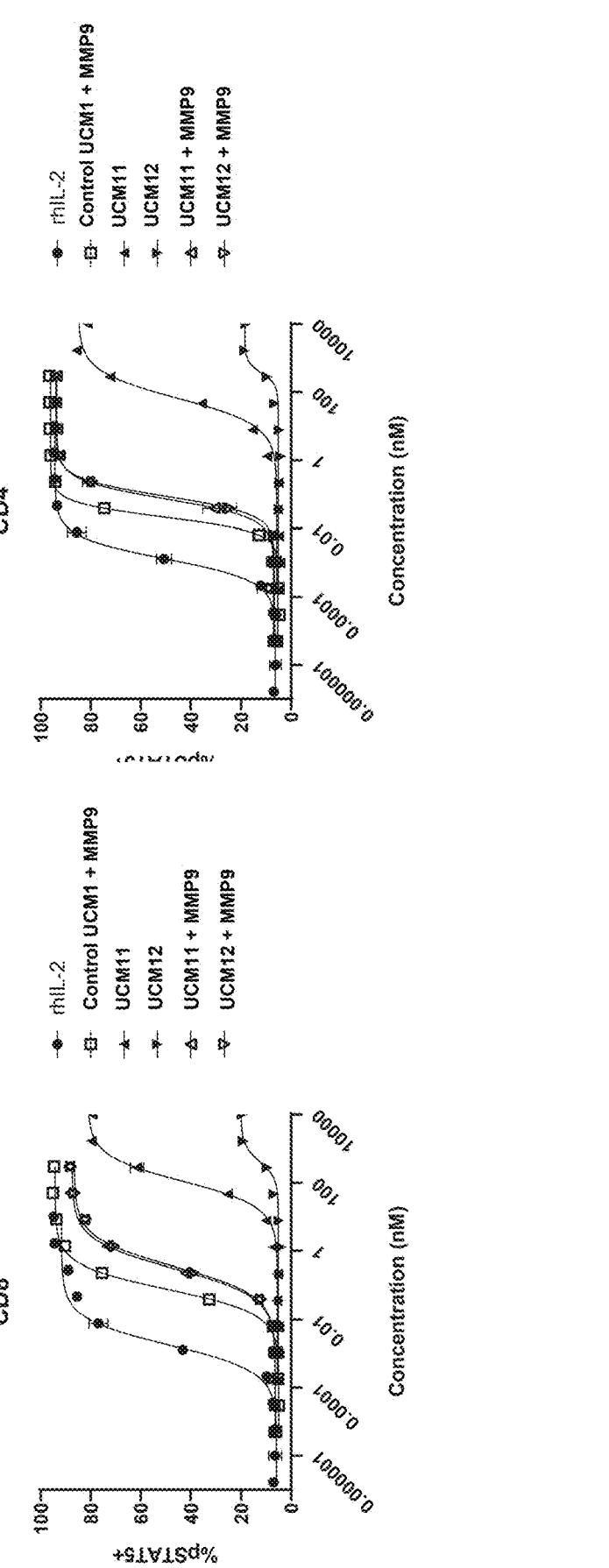
FIG. 6B is a series exemplary graphs illustrating percentage of STAT5 phosphorylation of UCM molecules with or without MMP9, illustrating restroation of IL-2 activity by proteolytic cleavage of the VHH masking moiety.
Figure 6C:
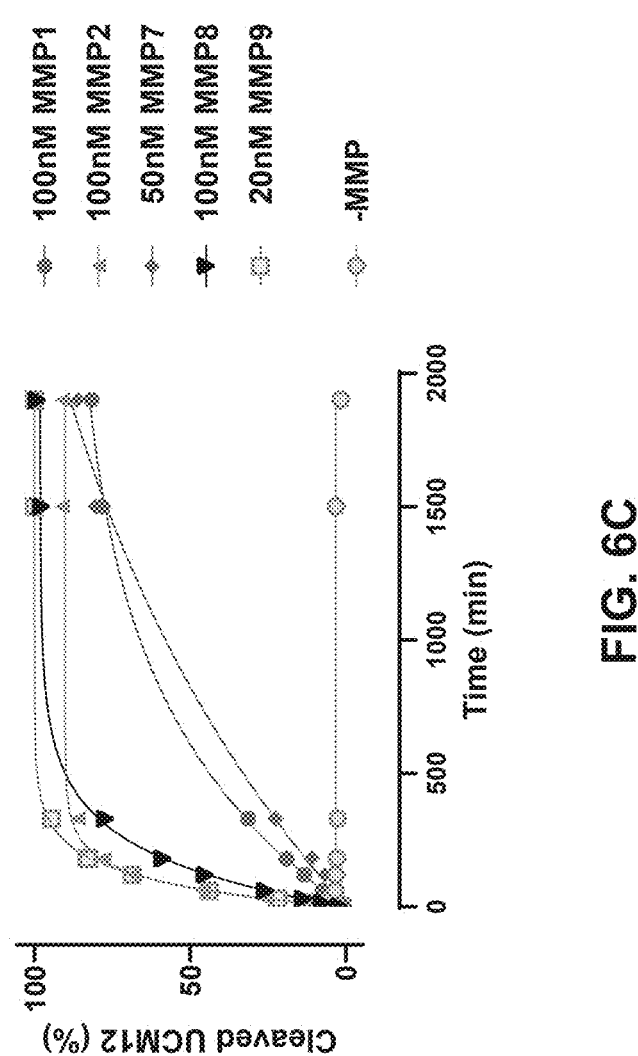
FIG. 6C shows cleavage of UCM12 by various proteases MMP1, MMP2, MMP7, MMP8, and MMP9.
Figure 6D:
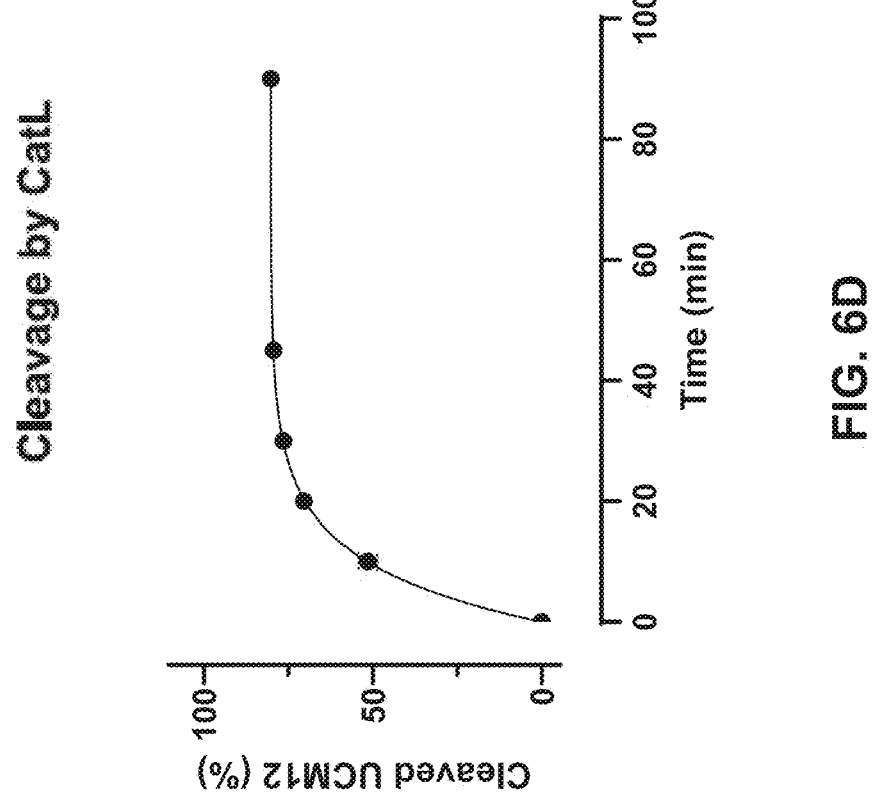
FIG. 6D shows cleavage of UCM12 by CatL.

Data presented in FIG. 6B illustrate that the UCM11 and UCM12 are effectively masked in the absence of cleavage; MMP9 cleaved UCM11 and UCM12 exhibit enhanced pSTAT5 activity. Table 2 also demonstrates that EC50 values for UCM11 and UCM12 decreased significantly (at least 300× fold) by addition of MMP9, demonstrating an increase in potency after proteolytic activation.

TABLE 2

EC values of Masked IL-2 Cytokines with or without MMP9

| | | Control UCM + | UCM11 | | UCM12 | |
|---|---|---|---|---|---|---|
| Sample | rhIL-2 | MMP9 | −MMP9 | +MMP9 | −MMP9 | +MMP9 |
| Donor 1 CD8 EC50 (nM) | 0.0018 | 0.077 | 111 | 0.31 | >10000 | 0.35 |
| Donor 1 CD4 EC50 (nM) | 0.0013 | 0.021 | 66 | 0.073 | >10000 | 0.088 |
| Donor 2 CD8 EC50 (nM) | 0.0021 | 0.059 | 106 | 0.23 | >10000 | 0.23 |
| Donor 2 CD4 EC50 (nM) | 0.0017 | 0.018 | 50 | 0.064 | >10000 | 0.069 |

Example 6. Validation of Effective Masking by VHH and Restoration of IL-2 Activity by Proteolytic Cleavage This example validates that masked IL-2 cytokines with a cleavable Fc domain are effectively masked by the VHH masking moieties and can be successfully cleaved by tumor-specific protease, restoring the potency of the IL-2 cytokine.

HEK Blue IL-2 cells (Invivogen) were grown as follows: Briefly, cells were passaged in growth medium (DMEM, 4.5 g/L glucose, 2 mM L-glutamine, 10% FBS, 50 U/mL penicillin, 50 µg/mL streptomycin, 100 µg/mL Normocin, 1× HEK-Blue CLR Selection, 1 µg/mL puromycin) until ~80% confluent. The cells were then spun down at 300g for 5 minutes and reconstituted with 10% DMS0, 20% Fetal Bovine Serum and 70% DMEM, 4.5 g/L glucose, 2 mM L-glutamine. They were frozen at −80° C. in a Corning CoolCell freezing container for 12 hours before placing in liquid nitrogen for long term storage to create a "thaw and use" bank. To perform the assay, frozen "thaw and use" HEK Blue IL-2 cells were thawed quickly in a 37° C. water bath before transferring to a 50 ml conical tube containing assay medium (DMEM, 4.5 g/L glucose, 2 mM L-glutamine, 10% FBS, 50 U/mL penicillin, 50 µg/mL streptomycin). The cells were spun at 300 g for 5 minutes then reconstituted at $0.3\times10^6$ viable cells per mL with assay media. The cells were plated at 50,000 cells per well in 96-well plate. 50 µL aliquots of serial dilutions of test articles in assay medium, from 1.2-100,000 pM final concentration for non-cleaved test articles and 0.1-8750 pM final concentration for cleaved test articles, were added to cells. The plate was incubated at 37° C., 5% CO2 for 24 hours.

After 24 hours, Quanti-Blue solution (Invivogen) was prepared according to manufacturer's recommendations. In a fresh 96-well plate, 20 µL of cell supernatant was added to 180 µL of Quanti-Blue solution. The plate was sealed, tapped gently to mix, and incubated for 2 hours at 37° C. before removing the cover and measuring absorbance at 625 nm.

Data analysis was performed in Graphpad Prism, version 10.1.2. Background (assay media) was subtracted from raw data to establish reference subtracted light units (RSLU) and these data were fit to a nonlinear regression equation: [Agonist] vs. response-Variable slope (four parameters). EC50 value of each construct was reported.

Figure 7:
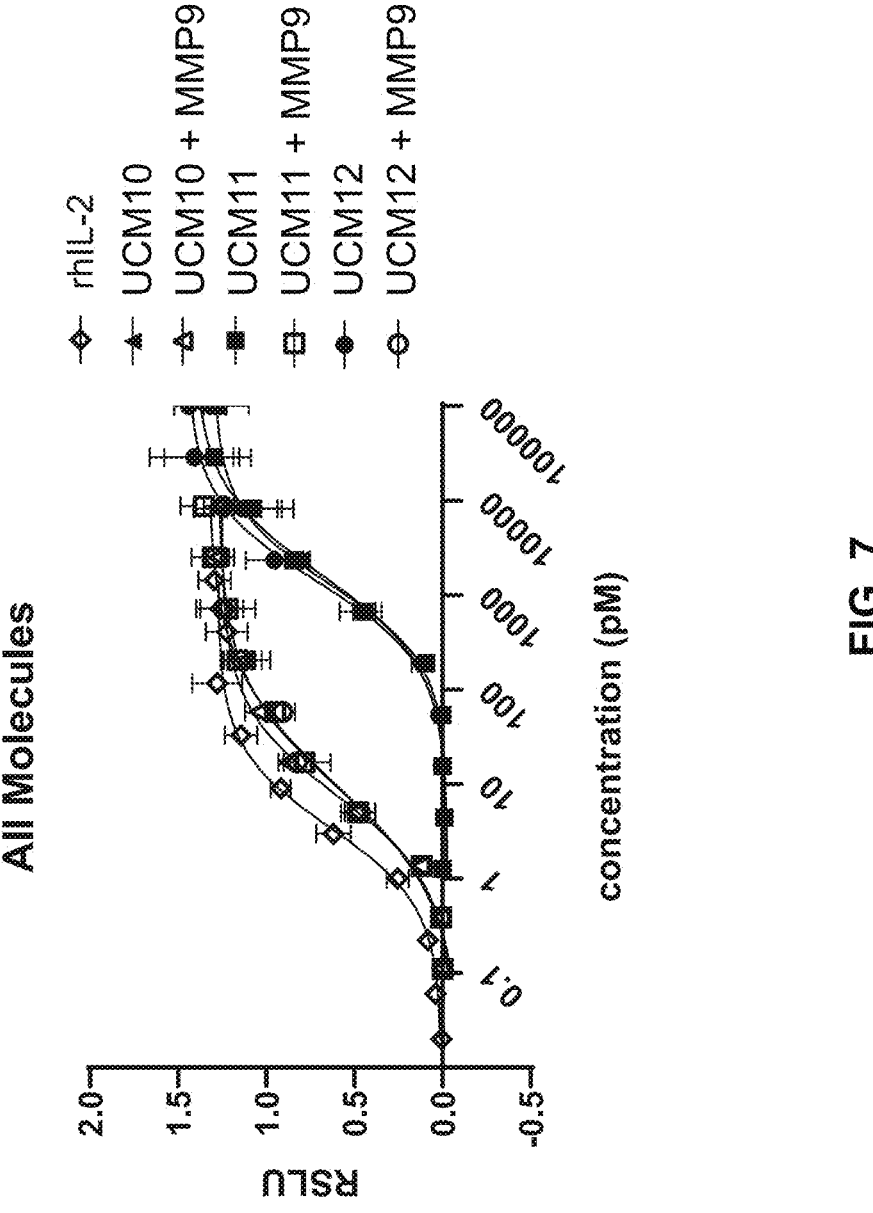
FIG. 7 is an exemplary graph illustrating reference subtracted light units (RSLU), indicative of IL-2 activity as tested with the HEK Blue IL-2 cells.

Data presented in FIG. 7 demonstrate that UCM10, UCM11 and UCM12 are effectively masked in the absence of cleavage; following cleavage by MMP9, UCM10, UCM11 and UCM12 exhibit similar activity to rhIL2 indicative of successful unmasking.

Example 7. Exemplary Masked IL-2 Cytokines Block PD-1/PD-LI Interaction

This example demonstrates that exemplary masked IL-2 cytokines maintain the ability to target PD-1 and block the PD-1/PD-L1 axis.

The ability to target PD-1 of exemplary masked IL-2 cytokines and a reference anti-PD1 antibody were tested using ELISA binding assay. ELISA plates were coated with recombinant human PD-1 before blocking and incubating with test articles over a concentration range of 30-0.0003 nM. Immobilized test articles were detected using a horse-radish peroxidase (HRP)-conjugated polyclonal anti-human fragment crystallizable antibody followed by colorimetric detection. The data demonstrates that the tested exemplary masked IL-2 cytokines and reference PD-1 antibody are equivalent binders of human PD-1.

Next, exemplary masked IL-2 cytokines and a reference anti-PD1 antibody with blocking activity for PD-1 were tested with the Promega PD-1/PD-L1 Blockade Bioassay. The bioassay was set up and run according to the manufacturer's protocol.

Briefly, the day before performing the assay, cell recovery medium supplied with the bioassay kit was prepared by adding the supplied FBS (90% Ham's F-12/10% FBS). A vial of PD-L1 aAPC/CHO-K1 cells was gently thawed in the 37° C. water bath for 3 minutes. The thawed vial of PD-L1 aAPC/CHO-K1 cells was added to pre-warmed recovery medium, and the cell solution was mixed by inversion 2 times. A volume of 100 µL of cell suspension was added to a tissue-culture treated 96-well, white, flat-bottom assay plate. The plates were covered and incubated overnight (37° C., 5% CO2).

On the following day, the assay plates containing the PD-L1 aAPC/CHO-K1 cells were removed from the incubator, and 95 µL of the recovery medium was removed from each of the wells. Serial dilutions of test articles, the exemplary masked IL-2 cytokines and reference antibody, were prepared in the provided assay buffer (99% RPMI 1640/1% FBS). 40 µL aliquots of the serial dilutions were added to the wells containing the PD-L1 aAPC/CHO-K1 cells with the final concentrations of the test articles ranging from 0.033-50 nM. Next, the PD-1 effector cells were prepared by thawing a vial of these cells in the 37° C. water bath for 3 minutes and adding the thawed effector cells to prewarmed assay buffer. The cell suspension was mixed by inversion 2 times before 40 µL of effector cell suspension was added to each of the wells. The assay plate was covered and incubated for 6 hours (37° C., 5% CO2).

After the 6-hour incubation, the assay plates were removed from the incubator and let to equilibrate to ambient temperature for 5-10 minutes. 80 µL of Bio-Glo reagent was added to each well, and the plates were incubated for 5 minutes at ambient temperature prior to measuring the luminescence.

Figure 8:
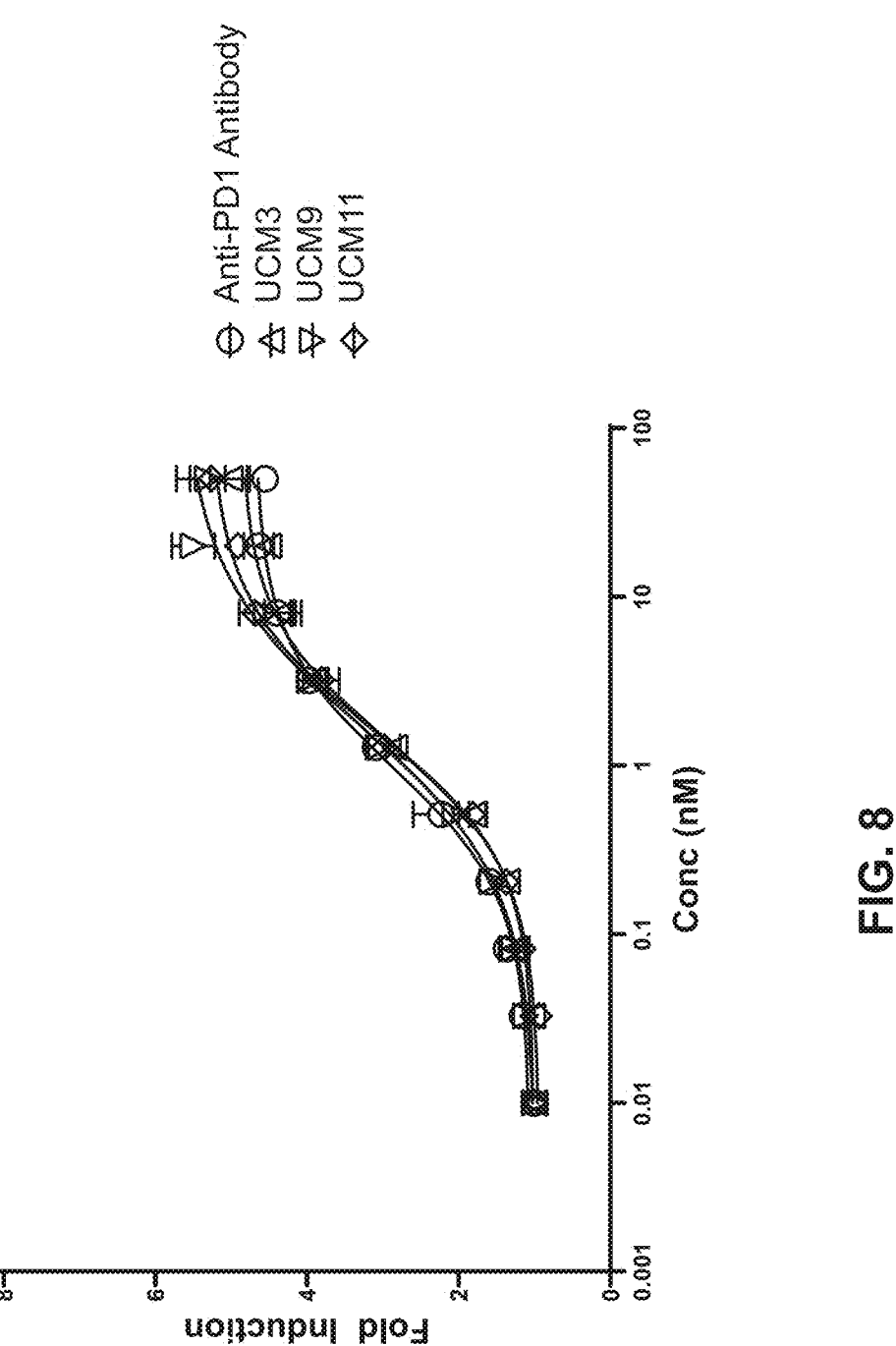
FIG. 8 is an exemplary graph showing the fold induction in TCR signaling for exemplary masked IL-2 cytokines in a PD-1/PD-L1 blockade bioassay.

The addition of the exemplary masked IL-2 cytokine in this assay serves to block the interaction between PD-L1, from the PD-L1 aAPC/CHO-K1, and PD-1, from the PD-1 effector cells. By blocking the interaction, the exemplary masked IL-2 cytokine releases the inhibitory signal, resulting in T-cell receptor (TCR) signaling and an increase in luminescence. The fold induction of luminescence for exemplary masked IL-2 cytokines in an exemplary experiment is shown in FIG. 8.

Exemplary masked IL-2 cytokines were tested using the Promega PD-1/PD-L1 blockade cell-based bioassay. As discussed above, the assay was set up and run according to the manufacturer's protocol with final concentrations of test articles (i.e., exemplary masked IL-2 cytokines and a reference anti-PD1 antibody) ranging from 0.033-50 nM. Data analysis was performed in GraphPad Prism. The fold induction was calculated by subtracting the luminescence of the background from the luminescence of the test article, and then dividing that by product of subtracting the background from a no antibody control (RLU [antibody-background]/ RLU [no antibody control-background]). The calculated EC50 value of each exemplary masked IL-2 cytokine is shown in Table 3. Data presented in Table 3 demonstrate that all exemplary masked IL2 cytokines tested demonstrate comparable ability to block the PD-1/PD-L1 axis as the reference anti-PD1 antibody.

TABLE 3

| EC50 Values for Exemplary Masked IL-2 Cytokines | |
| --- | --- |
| Test Article | EC$_{50}$ (nM) |
| Anti-PD1 Antibody | 0.98 |
| UCM1 | 0.93 |
| UCM2 | 0.84 |
| UCM3 | 1.42 |
| Control UCM2 | 0.59 |
| Control UCM1 | 0.70 |
| UCM4 | 1.28 |
| UCM5 | 1.15 |
| UCM6 | 1.20 |
| UCM7 | 1.36 |
| UCM8 | 1.09 |
| UCM9 | 1.76 |
| UCM11 | 1.60 |
| Control UCM3 | 0.78 |

Overall, this example shows that exemplary masked IL-2 cytokines have similar ability in blocking the PD-1/PD-L1 axis as a reference anti-PD1 antibody with known blocking activity.

Example 8. VHH Masking Moiety is Effective in Eliminating Binding to CD122

This example validates that an exemplary masked IL-2 cytokine, UCM12, is effectively masked by the VHH masking moiety. Surface plasmon resonance (SPR) measurement for the binding affinities of UCM12 to CD25 and CD122 were performed and compared to the binding affinities of unmasked controls, Control UCM1 and Control UCM2, and recombinant human IL-2 (rhIL-2; AcroBiosystems).

SPR measurements were performed at 25° C. by using a BIAcore T200 system with Biotin CAPture kit, series S (Cytiva). HBS-EP+buffer (150 mM NaCl; 10 mM HEPES; 3 mM EDTA and 0.05% (v/v) surfactant P20 pH 7.4) was used as running buffer. The chip was prepared following the vendor's recommendation. Briefly, the chip was rehydrated and subjected to surface conditioning, which are three one-minute injections of regeneration solution (6M guanidine-HCl; 0.25M NaOH). Then, three start-up cycles were run by injecting Biotin CAPture Reagent (Cytiva), ligand, analyte and regeneration solution.

At the beginning of each cycle, Biotin CAPture reagent was applied to the chip for 5 min. Biotinylated recombinant human CD25 or CD122 (AcroBiosystems) were used as ligands. Ligands were diluted into the running buffer to yield 0.04~2.0 ug/ml ligand and were immobilized on to flow channel 2 of the chip. Flow channel 1 was left blank to serve as the negative control. Serial three-fold dilutions of the test articles were performed in running buffer to yield 18.52 to 13,500 nM test article. Next, they were applied to flow over the chip surface for 2 min. The molecules were then allowed to dissociate for 5 min, followed by 2-min regeneration with regeneration solution after each cycle. To measure the binding affinities, steady-state affinity analysis was performed via BIACORE T200 Evaluation Software Version 3.2.1.

As shown in Table 4, exemplary masked IL-2 cytokine, UCM12, is effectively masked as it does not bind to CD122, unlike the unmasked controls. Furthermore, UCM12 binds to CD25 with 236-fold reduced affinity compared to rhIL-2.

TABLE 4

| Binding Affinity of Exemplary Masked IL-2 Cytokine UCM12 to human CD25 or CD122 | | |
| --- | --- | --- |
| Construct | CD25 K$_D$ (nM) | CD122 K$_D$ (nM) |
| rhIL-2 | 12.38 | 262.7 |
| Control UCM2 | 71.28 | 1857 |
| Control UCM1 | 2261 | 2224 |
| UCM12 | 2925 | No binding |

Example 9. Exemplary Masked IL-2 Cytokines Show Antibody-Like Pharmacokinetics This example demonstrates antibody-like pharmacokinetics from an exemplary masked IL-2 cytokine, UCM12, in a mouse model.

The nonclinical pharmacokinetics (PK) of exemplary masked IL-2 cytokine, UCM12 and unmasked UCM Control 1 were evaluated in human neonatal fragment crystallizable (FcRn) mice. Mice received a single dose of 1 mg/kg, 3 mg/kg or 10 mg/kg of UCM12 or equimolar doses of UCM Control 1 using intravenous (IV) infusion.

Animal bleeds were performed at 1 hours, 6 hours, 24 hours, 72 hours, 120 hours, 168 hours, 240 hours and 336 hours after dosing for PK analysis measurements. Whole blood (approximately 50 uL) was collected via submandibular bleed into a heparin-coated tube and inverted multiple times immediately. Plasma was separated by centrifugation for 10 minutes at 1,000 to 2,000×g at 4° C. After centrifugation, approximately 25 μL of the resulting supernatant (plasma) was immediately transferred into a designated tube and stored at −80° C. The plasma samples were maintained at 2 to 8° C. while handling.

UCM12 and UCM Control 1 plasma levels were measured using a Mesoscale Discovery (MSD) Assay with an anti-human Fc capture antibody and an anti-human Fc detection antibody. Pharmacokinetic parameters of total UCM12 and UCM Control 1 in plasma was determined using non-compartmental analysis (NCA) using WinNonlin v8.1 software.

Figure 9:
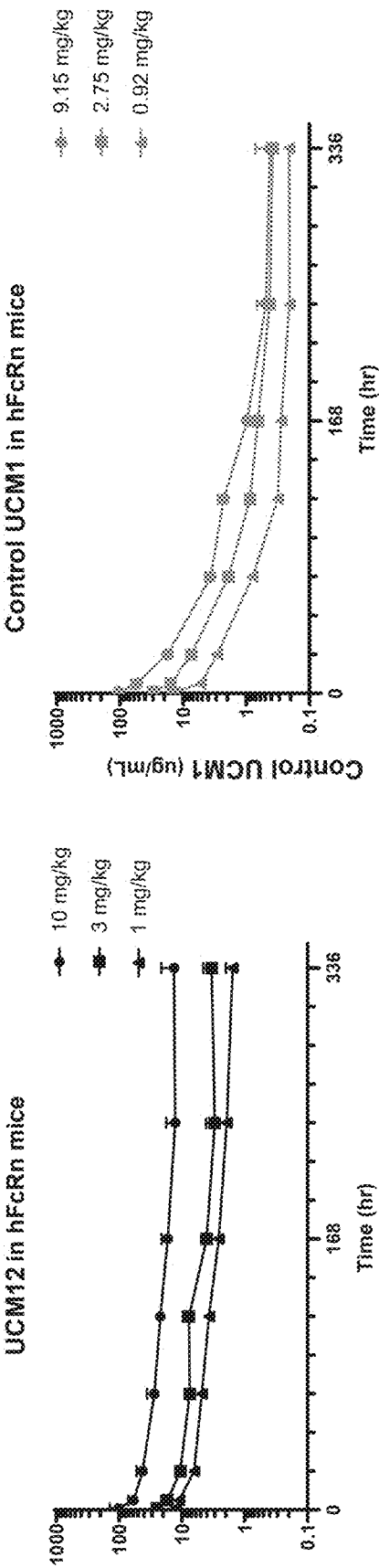
FIG. 9 shows the exemplary pharmacokinetics analysis of exemplary masked cytokine UCM12 in mice expressing human FcRn.

The plasma levels and PK parameters for UCM12 and Control UCM1 are shown in FIG. 9. These data demonstrate that UCM12 shows antibody-like PK in the hFcRn mouse model.

Example 10. Exemplary Masked IL-2 Cytokines Show Reduced Proliferation of PBMCs

This example demonstrates that exemplary masked IL-2 cytokines are effectively masked from stimulating proliferation of peripheral blood mononuclear cells (PBMCs).

Figure 10A:
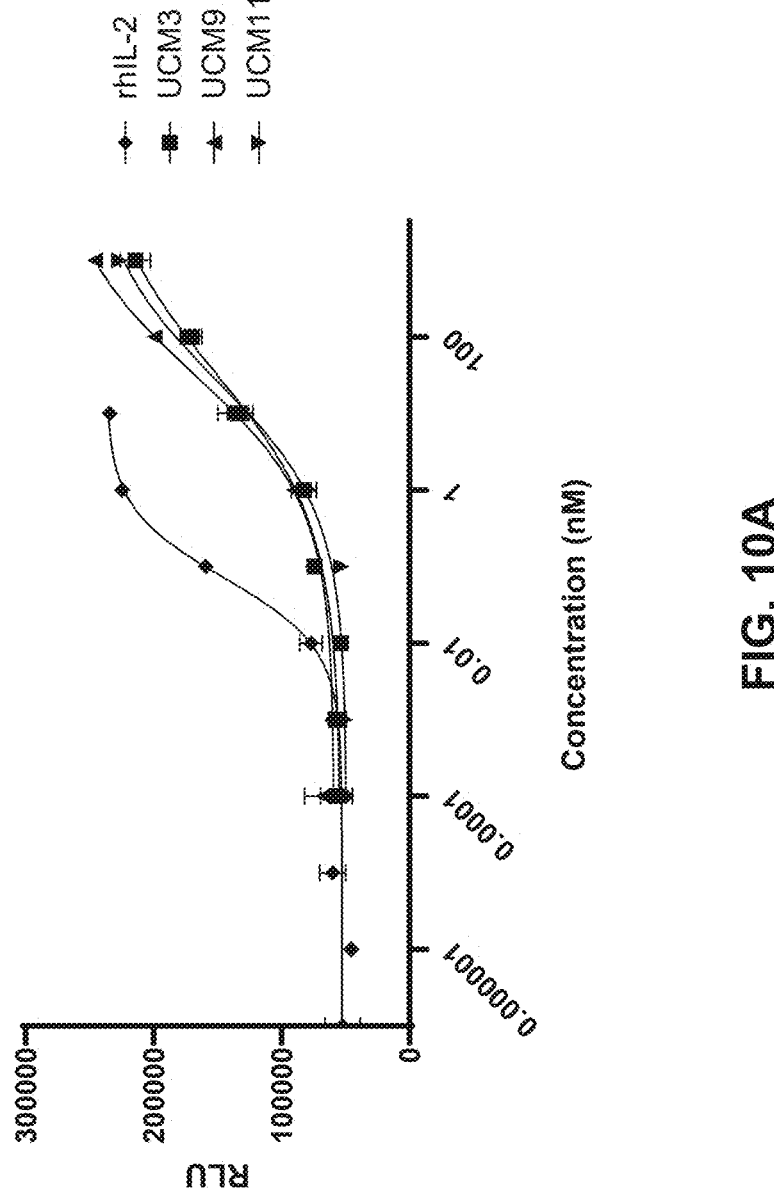
FIG. 10A shows the exemplary PBMCs proliferation of exemplary masked cytokines UCM3, UCM9 and UCM11.
Figure 10B:
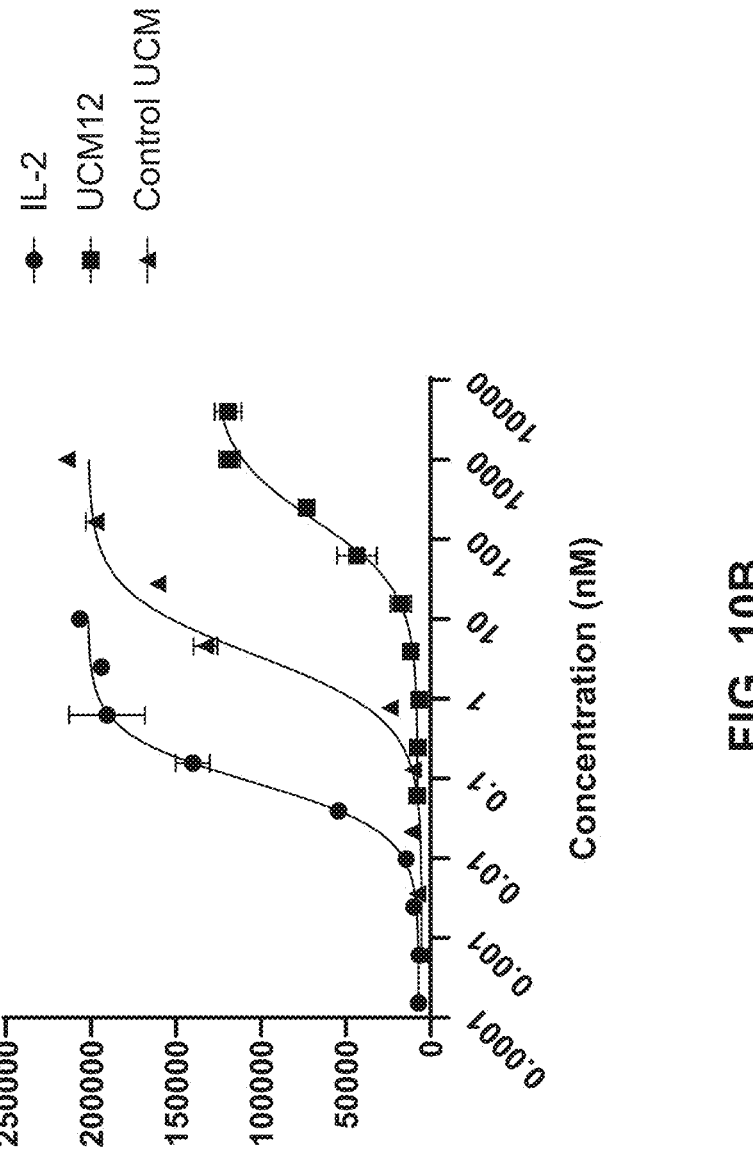
FIG. 10B shows reduced proliferation of PBMCs of the exemplary masked cytokine UCM12 relative to Control UCM1.

Human Peripheral blood mononuclear cells (PBMCs) were thawed and primed. Cells were then combined with test articles including exemplary masked IL-2 cytokines UCM3, UCM9, UCM11 and UCM12, recombinant human IL-2 as control and Control UCM1, at indicated concentrations (shown in FIGS. 10A and 10B). After 4-5 days of incubation, cells were harvested and proliferation was measured using Cell Titer Glo. Data presented demonstrate that UCM3, UCM9, UCM11 and UCM12 are less active than recombinant human IL-2 (FIGS. 10A and 10B). Data also demonstrate that UCM12 shows reduced proliferation of human PBMCs relative to unmasked control UCM1 (FIG. 10B).

EQUIVALENTS

Those skilled in the art will recognize or be able to ascertain using no more than routine experimentation, many equivalents to the specific embodiments of the invention described herein. The scope of the present invention is not intended to be limited to the above Description, but rather is as set forth in the following claims:

The invention claimed is:

1. A masked cytokine comprising:
a first polypeptide comprising an amino acid sequence of SEQ ID NO: 63,
a second polypeptide comprising an amino acid sequence of SEQ ID NO: 74, and
a third polypeptide comprising an amino acid sequence of SEQ ID NO: 50.

2. The masked cytokine of claim 1, further comprising a fourth polypeptide comprising an amino acid sequence of SEQ ID NO: 50.

3. The masked cytokine of claim 2, wherein the third polypeptide and the fourth polypeptide are identical.

4. A nucleic acid encoding the masked cytokine of claim 3.

5. A nucleic acid encoding the masked cytokine of claim 2.

6. A nucleic acid encoding the masked cytokine of claim 1.

* * * * *

```
                       SEQUENCE LISTING

Sequence total quantity: 75
SEQ ID NO: 1          moltype = AA  length = 4
FEATURE               Location/Qualifiers
source                1..4
                      mol_type = protein
                      organism = synthetic construct
SEQUENCE: 1
PLGL                                                          4

SEQ ID NO: 2          moltype = AA  length = 6
FEATURE               Location/Qualifiers
source                1..6
                      mol_type = protein
                      organism = synthetic construct
SEQUENCE: 2
SLPLGL                                                        6

SEQ ID NO: 3          moltype = AA  length = 6
FEATURE               Location/Qualifiers
source                1..6
                      mol_type = protein
                      organism = synthetic construct
SEQUENCE: 3
GGPLGL                                                        6

SEQ ID NO: 4          moltype =    length =
SEQUENCE: 4
000

SEQ ID NO: 5          moltype = AA  length = 8
FEATURE               Location/Qualifiers
source                1..8
                      mol_type = protein
                      organism = synthetic construct
SEQUENCE: 5
MPYDLYHP                                                      8

SEQ ID NO: 6          moltype = AA  length = 4
FEATURE               Location/Qualifiers
source                1..4
                      mol_type = protein
                      organism = synthetic construct
SEQUENCE: 6
```

```
APAG                                                                         4

SEQ ID NO: 7            moltype = AA  length = 10
FEATURE                Location/Qualifiers
source                 1..10
                       mol_type = protein
                       organism = synthetic construct
SEQUENCE: 7
APAGLIVPYN                                                                  10

SEQ ID NO: 8            moltype =   length =
SEQUENCE: 8
000

SEQ ID NO: 9            moltype = AA  length = 9
FEATURE                Location/Qualifiers
source                 1..9
                       mol_type = protein
                       organism = synthetic construct
SEQUENCE: 9
PANLVAPDP                                                                    9

SEQ ID NO: 10           moltype = AA  length = 133
FEATURE                Location/Qualifiers
source                 1..133
                       mol_type = protein
                       organism = synthetic construct
SEQUENCE: 10
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLT                                                      133

SEQ ID NO: 11           moltype = AA  length = 133
FEATURE                Location/Qualifiers
source                 1..133
                       mol_type = protein
                       organism = synthetic construct
SEQUENCE: 11
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFAQSIIS TLT                                                      133

SEQ ID NO: 12           moltype = AA  length = 133
FEATURE                Location/Qualifiers
source                 1..133
                       mol_type = protein
                       organism = synthetic construct
SEQUENCE: 12
APTSSSTKKT QLQLEHLLLD LQMILNGINN YKNPKLTAML TAKFAMPKKA TELKHLQCLE   60
EALKPLEEVL NLAQSKNFHL RPRDLISNIN VIVLELKGSE TTFMCEYADE TATIVEFLNR  120
WITFAQSIIS TLT                                                      133

SEQ ID NO: 13           moltype = AA  length = 133
FEATURE                Location/Qualifiers
source                 1..133
                       mol_type = protein
                       organism = synthetic construct
SEQUENCE: 13
APTSSSTKKT QLQLEHLLLD LQMILNGINN YKNPKLTRML TEKFYMPKKA TELKHLQCLE   60
EELKPLEEVL NLAQSKNFHL RPRDLISNIN VIVLELKGSE TTFMCEYADE TATIVEFLNR  120
WITFAQSIIS TLT                                                      133

SEQ ID NO: 14           moltype = AA  length = 10
FEATURE                Location/Qualifiers
source                 1..10
                       mol_type = protein
                       organism = synthetic construct
SEQUENCE: 14
GSIFSINVMG                                                                  10

SEQ ID NO: 15           moltype = AA  length = 16
FEATURE                Location/Qualifiers
source                 1..16
                       mol_type = protein
                       organism = synthetic construct
SEQUENCE: 15
AISSGGSTNY ADSVKG                                                           16

SEQ ID NO: 16           moltype = AA  length = 11
```

```
FEATURE            Location/Qualifiers
source             1..11
                   mol_type = protein
                   organism = synthetic construct
SEQUENCE: 16
ASSWYEDETD Y                                                         11

SEQ ID NO: 17      moltype = AA  length = 11
FEATURE            Location/Qualifiers
source             1..11
                   mol_type = protein
                   organism = synthetic construct
SEQUENCE: 17
ASSFYEDETD Y                                                         11

SEQ ID NO: 18      moltype =   length =
SEQUENCE: 18
000

SEQ ID NO: 19      moltype = AA  length = 119
FEATURE            Location/Qualifiers
source             1..119
                   mol_type = protein
                   organism = synthetic construct
SEQUENCE: 19
EVQLVESGGG LVQPGGSLRL SCAASGSIFS INVMGWYRQA PGKQRELVAA ISSGGSTNYA   60
DSVKGRFTIS RDNAKNTVYL QMNSLKPEDT AVYYCMYASS WYEDETDYWG QGTQVTVSS    119

SEQ ID NO: 20      moltype = AA  length = 119
FEATURE            Location/Qualifiers
source             1..119
                   mol_type = protein
                   organism = synthetic construct
SEQUENCE: 20
EVQLVESGGG LVQPGGSLRL SCAASGSIFS INVMGWYRQA PGKGRELVAA ISSGGSTNYA   60
DSVKGRFTIS RDNAKNTVYL QMNSLKPEDT AVYYCAYASS FYEDETDYWG QGTQVTVSS    119

SEQ ID NO: 21      moltype = AA  length = 122
FEATURE            Location/Qualifiers
source             1..122
                   mol_type = protein
                   organism = synthetic construct
SEQUENCE: 21
EVQLVESGGG LVQPGGSLRL SCAASGSIFS INVMGWYRQA PGKQRELVAA ISSGGSTNYA   60
DSVKGRFTIS RDNAKNTVYL QMNSLKPEDT AVYYCMYASS WYEDETDYWG QGTQVTVSSA   120
AA                                                                  122

SEQ ID NO: 22      moltype = AA  length = 122
FEATURE            Location/Qualifiers
source             1..122
                   mol_type = protein
                   organism = synthetic construct
SEQUENCE: 22
EVQLVESGGG LVQPGGSLRL SCAASGSIFS INVMGWYRQA PGKGRELVAA ISSGGSTNYA   60
DSVKGRFTIS RDNAKNTVYL QMNSLKPEDT AVYYCAYASS FYEDETDYWG QGTQVTVSSA   120
AA                                                                  122

SEQ ID NO: 23      moltype = AA  length = 227
FEATURE            Location/Qualifiers
source             1..227
                   mol_type = protein
                   organism = synthetic construct
SEQUENCE: 23
DKTHTCPPCP APELLGGPSV FLFPPKPKDT LMISRTPEVT CVVVDVSHED PEVKFNWYVD   60
GVEVHNAKTK PREEQYASTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKS LSLPLGL                227

SEQ ID NO: 24      moltype = AA  length = 227
FEATURE            Location/Qualifiers
source             1..227
                   mol_type = protein
                   organism = synthetic construct
SEQUENCE: 24
DKTHTCPPCP APELLGGPSV FLFPPKPKDT LMISRTPEVT CVVVDVSHED PEVKFNWYVD   60
GVEVHNAKTK PREEQYASTY RVVSVLTVLH QDWLNGKEYK CKVSNKALPA PIEKTISKAK   120
GQPREPQVCT LPPSRDELTK NQVSLSCAVK GFYPSDIAVE WESNGQPENN YKTTPPVLDS   180
DGSFFLVSKL TVDKSRWQQG NVFSCSVMHE ALHNHYTQKM PYDLYHP                227
```

```
SEQ ID NO: 25            moltype = AA  length = 227
FEATURE                  Location/Qualifiers
source                   1..227
                         mol_type = protein
                         organism = synthetic construct
SEQUENCE: 25
DKTHTCPPCP APELLGGPSV FLFPPKPKDT LMISRTPEVT CVVVDVSHED PEVKFNWYVD  60
GVEVHNAKTK PREEQYASTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTAPA GLIVPYN               227

SEQ ID NO: 26            moltype = AA  length = 226
FEATURE                  Location/Qualifiers
source                   1..226
                         mol_type = protein
                         organism = synthetic construct
SEQUENCE: 26
DKTHTCPPCP APELLGGPSV FLFPPKPKDT LMISRTPEVT CVVVDVSHED PEVKFNWYVD  60
GVEVHNAKTK PREEQYASTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTPAN LVAPDP                226

SEQ ID NO: 27            moltype = AA  length = 227
FEATURE                  Location/Qualifiers
source                   1..227
                         mol_type = protein
                         organism = synthetic construct
SEQUENCE: 27
DKTHTCPPCP APELLGGPSV FLFPPKPKDT LMISRTPEVT CVVVDVSHED PEVKFNWYVD  60
GVEVHNAKTK PREEQYASTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LGGPLGL               227

SEQ ID NO: 28            moltype = AA  length = 227
FEATURE                  Location/Qualifiers
source                   1..227
                         mol_type = protein
                         organism = synthetic construct
SEQUENCE: 28
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLVSKL TVDKSRWQQG NVFSCSVMHE ALHNHYTQKS LSLSPGK               227

SEQ ID NO: 29            moltype = AA  length = 226
FEATURE                  Location/Qualifiers
source                   1..226
                         mol_type = protein
                         organism = synthetic construct
SEQUENCE: 29
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPG                226

SEQ ID NO: 30            moltype = AA  length = 226
FEATURE                  Location/Qualifiers
source                   1..226
                         mol_type = protein
                         organism = synthetic construct
SEQUENCE: 30
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPG                226

SEQ ID NO: 31            moltype = AA  length = 226
FEATURE                  Location/Qualifiers
source                   1..226
                         mol_type = protein
                         organism = synthetic construct
SEQUENCE: 31
DKTHTCPPCP APELLGGPSV FLFPPKPKDT LMISRTPEVT CVVVDVSHED PEVKFNWYVD  60
GVEVHNAKTK PREEQYASTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPG                226

SEQ ID NO: 32            moltype = AA  length = 226
FEATURE                  Location/Qualifiers
```

```
source                   1..226
                         mol_type = protein
                         organism = synthetic construct
SEQUENCE: 32
DKTHTCPPCP APELLGGPSV FLFPPKPKDT LMISRTPEVT CVVVDVSHED PEVKFNWYVD  60
GVEVHNAKTK PREEQYASTY RVVSVLTVLH QDWLNGKEYK CKVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPG              226

SEQ ID NO: 33           moltype = AA  length = 226
FEATURE                 Location/Qualifiers
source                  1..226
                        mol_type = protein
                        organism = synthetic construct
SEQUENCE: 33
DKTHTCPPCP APELLGGPSV FLFPPKPKDT LMISRTPEVT CVVVDVSHED PEVKFNWYVD  60
GVEVHNAKTK PREEQYASTY RVVSVLTVLH QDWLNGKEYK CKVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNRFTQKS LSLSPG              226

SEQ ID NO: 34           moltype =   length =
SEQUENCE: 34
000

SEQ ID NO: 35           moltype =   length =
SEQUENCE: 35
000

SEQ ID NO: 36           moltype =   length =
SEQUENCE: 36
000

SEQ ID NO: 37           moltype =   length =
SEQUENCE: 37
000

SEQ ID NO: 38           moltype =   length =
SEQUENCE: 38
000

SEQ ID NO: 39           moltype =   length =
SEQUENCE: 39
000

SEQ ID NO: 40           moltype =   length =
SEQUENCE: 40
000

SEQ ID NO: 41           moltype = AA  length = 120
FEATURE                 Location/Qualifiers
source                  1..120
                        mol_type = protein
                        organism = synthetic construct
SEQUENCE: 41
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120

SEQ ID NO: 42           moltype = AA  length = 119
FEATURE                 Location/Qualifiers
source                  1..119
                        mol_type = protein
                        organism = synthetic construct
SEQUENCE: 42
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KTSENLYFQ   119

SEQ ID NO: 43           moltype = AA  length = 8
FEATURE                 Location/Qualifiers
source                  1..8
                        mol_type = protein
                        organism = synthetic construct
SEQUENCE: 43
GYTFTNYY                                                           8

SEQ ID NO: 44           moltype = AA  length = 8
FEATURE                 Location/Qualifiers
source                  1..8
                        mol_type = protein
                        organism = synthetic construct
```

```
SEQUENCE: 44
INPSNGGT                                                                   8

SEQ ID NO: 45          moltype = AA   length = 13
FEATURE                Location/Qualifiers
source                 1..13
                       mol_type = protein
                       organism = synthetic construct
SEQUENCE: 45
ARRDYRFDMG FDY                                                             13

SEQ ID NO: 46          moltype = AA   length = 10
FEATURE                Location/Qualifiers
source                 1..10
                       mol_type = protein
                       organism = synthetic construct
SEQUENCE: 46
KGVSTSGYSY                                                                 10

SEQ ID NO: 47          moltype =    length =
SEQUENCE: 47
000

SEQ ID NO: 48          moltype = AA   length = 9
FEATURE                Location/Qualifiers
source                 1..9
                       mol_type = protein
                       organism = synthetic construct
SEQUENCE: 48
QHSRDLPLT                                                                  9

SEQ ID NO: 49          moltype = AA   length = 223
FEATURE                Location/Qualifiers
source                 1..223
                       mol_type = protein
                       organism = synthetic construct
SEQUENCE: 49
QVQLVQSGVE VKKPGASVKV SCKASGYTFT NYYMYWVRQA PGQGLEWMGG INPSNGGTNF   60
NEKFKNRVTL TTDSSTTTAY MELKSLQFDD TAVYYCARRD YRFDMGFDYW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSC                    223

SEQ ID NO: 50          moltype = AA   length = 218
FEATURE                Location/Qualifiers
source                 1..218
                       mol_type = protein
                       organism = synthetic construct
SEQUENCE: 50
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                          218

SEQ ID NO: 51          moltype = AA   length = 113
FEATURE                Location/Qualifiers
source                 1..113
                       mol_type = protein
                       organism = synthetic construct
SEQUENCE: 51
QVQLVESGGG VVQPGRSLRL DCKASGITFS NSGMHWVRQA PGKGLEWVAV IWYDGSKRYY   60
ADSVKGRFTI SRDNSKNTLF LQMNSLRAED TAVYYCATND DYWGQGTLVT VSS          113

SEQ ID NO: 52          moltype = AA   length = 440
FEATURE                Location/Qualifiers
source                 1..440
                       mol_type = protein
                       organism = synthetic construct
SEQUENCE: 52
QVQLVESGGG VVQPGRSLRL DCKASGITFS NSGMHWVRQA PGKGLEWVAV IWYDGSKRYY   60
ADSVKGRFTI SRDNSKNTLF LQMNSLRAED TAVYYCATND DYWGQGTLVT VSSASTKGPS   120
VFPLAPCSRS TSESTAALGC LVKDYFPEPV TVSWNSGALT SGVHTFPAVL QSSGLYSLSS   180
VVTVPSSSLG TKTYTCNVDH KPSNTKVDKR VESKYGPPCP PCPAPEFLGG PSVFLFPPKP   240
KDTLMISRTP EVTCVVVDVS QEDPEVQFNW YVDGVEVHNA KTKPREEQFN STYRVVSVLT   300
VLHQDWLNGK EYKCKVSNKG LPSSIEKTIS KAKGQPREPQ VYTLPPSQEE MTKNQVSLTC   360
LVKGFYPSDI AVEWESNGQP ENNYKTTPPV LDSDGSFFLY SRLTVDKSRW QEGNVFSCSV   420
MHEALHNHYT QKSLSLSLGK                                               440

SEQ ID NO: 53          moltype = AA   length = 8
FEATURE                Location/Qualifiers
```

-continued

```
source                  1..8
                        mol_type = protein
                        organism = synthetic construct
SEQUENCE: 53
GITFSNSG                                                                        8

SEQ ID NO: 54           moltype = AA   length = 17
FEATURE                 Location/Qualifiers
source                  1..17
                        mol_type = protein
                        organism = synthetic construct
SEQUENCE: 54
VIWYDGSKRY YADSVKG                                                              17

SEQ ID NO: 55           moltype = AA   length = 6
FEATURE                 Location/Qualifiers
source                  1..6
                        mol_type = protein
                        organism = synthetic construct
SEQUENCE: 55
ATNDDY                                                                          6

SEQ ID NO: 56           moltype = AA   length = 107
FEATURE                 Location/Qualifiers
source                  1..107
                        mol_type = protein
                        organism = synthetic construct
SEQUENCE: 56
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ SSNWPRTFGQ GTKVEIK                 107

SEQ ID NO: 57           moltype = AA   length = 213
FEATURE                 Location/Qualifiers
source                  1..213
                        mol_type = protein
                        organism = synthetic construct
SEQUENCE: 57
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ SSNWPRTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGE                                213

SEQ ID NO: 58           moltype = AA   length = 6
FEATURE                 Location/Qualifiers
source                  1..6
                        mol_type = protein
                        organism = synthetic construct
SEQUENCE: 58
QSVSSY                                                                          6

SEQ ID NO: 59           moltype =    length =
SEQUENCE: 59
000

SEQ ID NO: 60           moltype = AA   length = 9
FEATURE                 Location/Qualifiers
source                  1..9
                        mol_type = protein
                        organism = synthetic construct
SEQUENCE: 60
QQSSNWPRT                                                                       9

SEQ ID NO: 61           moltype = AA   length = 5
FEATURE                 Location/Qualifiers
source                  1..5
                        mol_type = protein
                        organism = synthetic construct
SEQUENCE: 61
GGGGS                                                                           5

SEQ ID NO: 62           moltype = AA   length = 15
FEATURE                 Location/Qualifiers
source                  1..15
                        mol_type = protein
                        organism = synthetic construct
SEQUENCE: 62
GGGGSGGGGS GGGGS                                                                15

SEQ ID NO: 63           moltype = AA   length = 599
```

```
FEATURE                   Location/Qualifiers
source                    1..599
                          mol_type = protein
                          organism = synthetic construct
SEQUENCE: 63
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS 120
ASTKGPSVFP LAPSSKSTSG GTAALGCLVK DYFPEPVTVS WNSGALTSGV HTFPAVLQSS 180
GLYSLSSVVT VPSSSLGTQT YICNVNHKPS NTKVDKKVEP KSCDKTHTCP PCPAPELLGG 240
PSVFLFPPKP KDTLMISRTP EVTCVVVDVS HEDPEVKFNW YVDGVEVHNA KTKPREEQYA 300
STYRVVSVLT VLHQDWLNGK EYKCKVSNKA LPAPIEKTIS KAKGQPREPQ VYTLPPCRDE 360
LTKNQVSLWC LVKGFYPSDI AVEWESNGQP ENNYKTTPPV LDSDGSFFLY SKLTVDKSRW 420
QQGNVFSCSV MHEALHNRFT QKSLSLSPGG GSSPPGGGSS GGGSGPAPTS SSTKKTQLQL 480
EHLLLDLQMI LNGINNYKNP KLTRMLTEKF YMPKKATELK HLQCLEEELK PLEEVLNLAQ 540
SKNFHLRPRD LISNINVIVL ELKGSETTFM CEYADETATI VEFLNRWITF AQSIISTLT  599

SEQ ID NO: 64            moltype = AA  length = 599
FEATURE                   Location/Qualifiers
source                    1..599
                          mol_type = protein
                          organism = synthetic construct
SEQUENCE: 64
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS 120
ASTKGPSVFP LAPSSKSTSG GTAALGCLVK DYFPEPVTVS WNSGALTSGV HTFPAVLQSS 180
GLYSLSSVVT VPSSSLGTQT YICNVNHKPS NTKVDKKVEP KSCDKTHTCP PCPAPELLGG 240
PSVFLFPPKP KDTLMISRTP EVTCVVVDVS HEDPEVKFNW YVDGVEVHNA KTKPREEQYA 300
STYRVVSVLT VLHQDWLNGK EYKCKVSNKA LPAPIEKTIS KAKGQPREPQ VYTLPPCRDE 360
LTKNQVSLWC LVKGFYPSDI AVEWESNGQP ENNYKTTPPV LDSDGSFFLY SKLTVDKSRW 420
QQGNVFSCSV MHEALHNRFT QKSLSLSPGG GSSPPGGGSS GGGSGPAPTS SSTKKTQLQL 480
EHLLLDLQMI LNGINNYKNP KLTRMLTFKF YMPKKATELK HLQCLEEELK PLEEVLNLAQ 540
SKNFHLRPRD LISNINVIVL ELKGSETTFM CEYADETATI VEFLNRWITF AQSIISTLT  599

SEQ ID NO: 65            moltype = AA  length = 599
FEATURE                   Location/Qualifiers
source                    1..599
                          mol_type = protein
                          organism = synthetic construct
SEQUENCE: 65
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS 120
ASTKGPSVFP LAPSSKSTSG GTAALGCLVK DYFPEPVTVS WNSGALTSGV HTFPAVLQSS 180
GLYSLSSVVT VPSSSLGTQT YICNVNHKPS NTKVDKKVEP KSCDKTHTCP PCPAPELLGG 240
PSVFLFPPKP KDTLMISRTP EVTCVVVDVS HEDPEVKFNW YVDGVEVHNA KTKPREEQYA 300
STYRVVSVLT VLHQDWLNGK EYKCKVSNKA LPAPIEKTIS KAKGQPREPQ VYTLPPCRDE 360
LTKNQVSLWC LVKGFYPSDI AVEWESNGQP ENNYKTTPPV LDSDGSFFLY SKLTVDKSRW 420
QQGNVFSCSV MHEALHNRFT QKSLSLSPGG GSSPPGGGSS GGGSGPAPTS SSTKKTQLQL 480
EHLLLDLQMI LNGINNYKNP KLTAMLTAKF AMPKKATELK HLQCLEEALK PLEEVLNLAQ 540
SKNFHLRPRD LISNINVIVL ELKGSETTFM CEYADETATI VEFLNRWITF AQSIISTLT  599

SEQ ID NO: 66            moltype = AA  length = 587
FEATURE                   Location/Qualifiers
source                    1..587
                          mol_type = protein
                          organism = synthetic construct
SEQUENCE: 66
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS 120
ASTKGPSVFP LAPSSKSTSG GTAALGCLVK DYFPEPVTVS WNSGALTSGV HTFPAVLQSS 180
GLYSLSSVVT VPSSSLGTQT YICNVNHKPS NTKVDKKVEP KSCDKTHTCP PCPAPELLGG 240
PSVFLFPPKP KDTLMISRTP EVTCVVVDVS HEDPEVKFNW YVDGVEVHNA KTKPREEQYA 300
STYRVVSVLT VLHQDWLNGK EYKCKVSNKA LPAPIEKTIS KAKGQPREPQ VCTLPPSRDE 360
LTKNQVSLSC AVKGFYPSDI AVEWESNGQP ENNYKTTPPV LDSDGSFFLV SKLTVDKSRW 420
QQGNVFSCSV MHEALHNHYT QKSLSLPLGL GGSSGSGGSG GGGSGSGGEV QLVESGGGLV 480
QPGGSLRLSC AASGSIFSIN VMGWYRQAPG KQRELVAAIS SGGSTNYADS VKGRFTISRD 540
NAKNTVYLQM NSLKPEDTAV YYCMYASSWY EDETDYWGQG TQVTVSS     587

SEQ ID NO: 67            moltype = AA  length = 587
FEATURE                   Location/Qualifiers
source                    1..587
                          mol_type = protein
                          organism = synthetic construct
SEQUENCE: 67
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS 120
ASTKGPSVFP LAPSSKSTSG GTAALGCLVK DYFPEPVTVS WNSGALTSGV HTFPAVLQSS 180
GLYSLSSVVT VPSSSLGTQT YICNVNHKPS NTKVDKKVEP KSCDKTHTCP PCPAPELLGG 240
PSVFLFPPKP KDTLMISRTP EVTCVVVDVS HEDPEVKFNW YVDGVEVHNA KTKPREEQYA 300
STYRVVSVLT VLHQDWLNGK EYKCKVSNKA LPAPIEKTIS KAKGQPREPQ VCTLPPSRDE 360
```

```
LTKNQVSLSC AVKGFYPSDI AVEWESNGQP ENNYKTTPPV LDSDGSFFLV SKLTVDKSRW    420
QQGNVFSCSV MHEALHNHYT QKSLGGPLGL GGSSGSGGGS GGSGSGGGEV QLVESGGGLV    480
QPGGSLRLSC AASGSIFSIN VMGWYRQAPG KQRELVAAIS SGGSTNYADS VKGRFTISRD    540
NAKNTVYLQM NSLKPEDTAV YYCMYASSWY EDETDYWGQG TQVTVSS                  587

SEQ ID NO: 68              moltype = AA   length = 587
FEATURE                    Location/Qualifiers
source                     1..587
                           mol_type = protein
                           organism = synthetic construct
SEQUENCE: 68
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPELLGG    240
PSVFLFPPKP KDTLMISRTP EVTCVVVDVS HEDPEVKFNW YVDGVEVHNA KTKPREEQYA    300
STYRVVSVLT VLHQDWLNGK EYKCKVSNKA LPAPIEKTIS KAKGQPREPQ VCTLPPSRDE    360
LTKNQVSLSC AVKGFYPSDI AVEWESNGQP ENNYKTTPPV LDSDGSFFLV SKLTVDKSRW    420
QQGNVFSCSV MHEALHNHYT QKMPYDLYHP GGSSGSGGGS GGSGSGGGEV QLVESGGGLV    480
QPGGSLRLSC AASGSIFSIN VMGWYRQAPG KQRELVAAIS SGGSTNYADS VKGRFTISRD    540
NAKNTVYLQM NSLKPEDTAV YYCMYASSWY EDETDYWGQG TQVTVSS                  587

SEQ ID NO: 69              moltype = AA   length = 587
FEATURE                    Location/Qualifiers
source                     1..587
                           mol_type = protein
                           organism = synthetic construct
SEQUENCE: 69
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPELLGG    240
PSVFLFPPKP KDTLMISRTP EVTCVVVDVS HEDPEVKFNW YVDGVEVHNA KTKPREEQYA    300
STYRVVSVLT VLHQDWLNGK EYKCKVSNKA LPAPIEKTIS KAKGQPREPQ VCTLPPSRDE    360
LTKNQVSLSC AVKGFYPSDI AVEWESNGQP ENNYKTTPPV LDSDGSFFLV SKLTVDKSRW    420
QQGNVFSCSV MHEALHNHYT APAGLIVPYN GGSSGSGGGS GGSGSGGGEV QLVESGGGLV    480
QPGGSLRLSC AASGSIFSIN VMGWYRQAPG KQRELVAAIS SGGSTNYADS VKGRFTISRD    540
NAKNTVYLQM NSLKPEDTAV YYCMYASSWY EDETDYWGQG TQVTVSS                  587

SEQ ID NO: 70              moltype = AA   length = 587
FEATURE                    Location/Qualifiers
source                     1..587
                           mol_type = protein
                           organism = synthetic construct
SEQUENCE: 70
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPELLGG    240
PSVFLFPPKP KDTLMISRTP EVTCVVVDVS HEDPEVKFNW YVDGVEVHNA KTKPREEQYA    300
STYRVVSVLT VLHQDWLNGK EYKCKVSNKA LPAPIEKTIS KAKGQPREPQ VCTLPPSRDE    360
LTKNQVSLSC AVKGFYPSDI AVEWESNGQP ENNYKTTPPV LDSDGSFFLV SKLTVDKSRW    420
QQGNVFSCSV MHEALHNHYT PANLVAPDPG GGSSGSGGGS GGSGSGGGEV QLVESGGGLV    480
QPGGSLRLSC AASGSIFSIN VMGWYRQAPG KQRELVAAIS SGGSTNYADS VKGRFTISRD    540
NAKNTVYLQM NSLKPEDTAV YYCMYASSWY EDETDYWGQG TQVTVSS                  587

SEQ ID NO: 71              moltype = AA   length = 593
FEATURE                    Location/Qualifiers
source                     1..593
                           mol_type = protein
                           organism = synthetic construct
SEQUENCE: 71
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPELLGG    240
PSVFLFPPKP KDTLMISRTP EVTCVVVDVS HEDPEVKFNW YVDGVEVHNA KTKPREEQYA    300
STYRVVSVLT VLHQDWLNGK EYKCKVSNKA LPAPIEKTIS KAKGQPREPQ VCTLPPSRDE    360
LTKNQVSLSC AVKGFYPSDI AVEWESNGQP ENNYKTTPPV LDSDGSFFLV SKLTVDKSRW    420
QQGNVFSCSV MHEALHNHYT QKSLSLPLGL GGSSGSGGGS GGSGSGGGS GSGGEVQLVE    480
SGGGLVQPGG SLRLSCAASG SIFSINVMGW YRQAPGKQRE LVAAISSGGS TNYADSVKGR    540
FTISRDNAKN TVYLQMNSLK PEDTAVYYCM YASSWYEDET DYWGQGTQVT VSS          593

SEQ ID NO: 72              moltype = AA   length = 587
FEATURE                    Location/Qualifiers
source                     1..587
                           mol_type = protein
                           organism = synthetic construct
SEQUENCE: 72
```

```
QVQLVQSGVE VKKPGASVKV SCKASGYTFT NYYMYWVRQA PGQGLEWMGG INPSNGGTNF   60
NEKFKNRVTL TTDSSTTTAY MELKSLQFDD TAVYYCARRD YRFDMGFDYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYA  300
STYRVVSVLT VLHQDWLNGK EYKCKVSNKA LPAPIEKTIS KAKGQPREPQ VCTLPPSRDE  360
LTKNQVSLSC AVKGFYPSDI AVEWESNGQP ENNYKTTPPV LDSDGSFFLV SKLTVDKSRW  420
QQGNVFSCSV MHEALHNHYT QKSLSLPLGL GGSSGSGGSG GGSGSGGGEV QLVESGGGLV  480
QPGGSLRLSC AASGSIFSIN VMGWYRQAPG KGRELVAAIS SGGSTNYADS VKGRFTISRD  540
NAKNTVYLQM NSLKPEDTAV YYCAYASSYY EDETDYWGQG TQVTVSS               587

SEQ ID NO: 73           moltype = AA  length = 587
FEATURE                 Location/Qualifiers
source                  1..587
                        mol_type = protein
                        organism = synthetic construct
SEQUENCE: 73
QVQLVQSGVE VKKPGASVKV SCKASGYTFT NYYMYWVRQA PGQGLEWMGG INPSNGGTNF   60
NEKFKNRVTL TTDSSTTTAY MELKSLQFDD TAVYYCARRD YRFDMGFDYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYA  300
STYRVVSVLT VLHQDWLNGK EYKCKVSNKA LPAPIEKTIS KAKGQPREPQ VCTLPPSRDE  360
LTKNQVSLSC AVKGFYPSDI AVEWESNGQP ENNYKTTPPV LDSDGSFFLV SKLTVDKSRW  420
QQGNVFSCSV MHEALHNHYT QKSLGGPLGL GGSSGSGGSG GGSGSGGGEV QLVESGGGLV  480
QPGGSLRLSC AASGSIFSIN VMGWYRQAPG KGRELVAAIS SGGSTNYADS VKGRFTISRD  540
NAKNTVYLQM NSLKPEDTAV YYCAYASSYY EDETDYWGQG TQVTVSS               587

SEQ ID NO: 74           moltype = AA  length = 590
FEATURE                 Location/Qualifiers
source                  1..590
                        mol_type = protein
                        organism = synthetic construct
SEQUENCE: 74
QVQLVQSGVE VKKPGASVKV SCKASGYTFT NYYMYWVRQA PGQGLEWMGG INPSNGGTNF   60
NEKFKNRVTL TTDSSTTTAY MELKSLQFDD TAVYYCARRD YRFDMGFDYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYA  300
STYRVVSVLT VLHQDWLNGK EYKCKVSNKA LPAPIEKTIS KAKGQPREPQ VCTLPPSRDE  360
LTKNQVSLSC AVKGFYPSDI AVEWESNGQP ENNYKTTPPV LDSDGSFFLV SKLTVDKSRW  420
QQGNVFSCSV MHEALHNHYT QKSLGGPLGL GGSSGSGGSG GGSGSGGGEV QLVESGGGLV  480
QPGGSLRLSC AASGSIFSIN VMGWYRQAPG KQRELVAAIS SGGSTNYADS VKGRFTISRD  540
NAKNTVYLQM NSLKPEDTAV YYCMYASSWY EDETDYWGQG TQVTVSSAAA           590

SEQ ID NO: 75           moltype = AA  length = 449
FEATURE                 Location/Qualifiers
source                  1..449
                        mol_type = protein
                        organism = synthetic construct
SEQUENCE: 75
QVQLVQSGVE VKKPGASVKV SCKASGYTFT NYYMYWVRQA PGQGLEWMGG INPSNGGTNF   60
NEKFKNRVTL TTDSSTTTAY MELKSLQFDD TAVYYCARRD YRFDMGFDYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYA  300
STYRVVSVLT VLHQDWLNGK EYKCKVSNKA LPAPIEKTIS KAKGQPREPQ VCTLPPSRDE  360
LTKNQVSLSC AVKGFYPSDI AVEWESNGQP ENNYKTTPPV LDSDGSFFLV SKLTVDKSRW  420
QQGNVFSCSV MHEALHNHYT QKSLSLSPG                                  449
```